(12) United States Patent
Zhang

(10) Patent No.: US 11,034,686 B2
(45) Date of Patent: Jun. 15, 2021

(54) AMINOPYRIDINE DERIVATIVES AS TAM FAMILY KINASE INHIBITORS

(71) Applicant: SignalChem Lifesciences Corporation, Richmond (CA)

(72) Inventor: Zaihui Zhang, Richmond (CA)

(73) Assignee: SignalChem Lifesciences Corporation, Richmond (CA)

( * ) Notice: Subject to any disclaimer, the term of this patent is extended or adjusted under 35 U.S.C. 154(b) by 0 days.

(21) Appl. No.: 16/899,494

(22) Filed: Jun. 11, 2020

(65) Prior Publication Data

US 2020/0299288 A1 Sep. 24, 2020

Related U.S. Application Data

(62) Division of application No. 16/254,208, filed on Jan. 22, 2019, now Pat. No. 10,723,725, which is a division of application No. 15/039,609, filed as application No. PCT/US2014/067709 on Nov. 26, 2014, now Pat. No. 10,233,176.

(60) Provisional application No. 61/909,830, filed on Nov. 27, 2013, provisional application No. 61/909,828, filed on Nov. 27, 2013.

(51) Int. Cl.
C07D 413/14 (2006.01)

(52) U.S. Cl.
CPC ................... *C07D 413/14* (2013.01)

(58) Field of Classification Search
CPC .................................................. C07D 413/14
See application file for complete search history.

(56) References Cited

U.S. PATENT DOCUMENTS

| 2009/0197862 A1 | 8/2009 | Steinig et al. |
| 2010/0075965 A1 | 3/2010 | Ni et al. |
| 2011/0003859 A1 | 1/2011 | Ahrendt |
| 2012/0295902 A1 | 11/2012 | Jonczyk et al. |

FOREIGN PATENT DOCUMENTS

| EP | 1 900 727 A1 | 3/2008 |
| JP | 2009-530233 A | 8/2009 |
| JP | 2011-511005 A | 4/2011 |
| JP | 2011-513332 A | 4/2011 |
| JP | 2011-527684 A | 11/2011 |
| JP | 2013-518832 A | 5/2013 |
| JP | 2016-504374 A | 2/2016 |
| WO | 2010/005876 A2 | 1/2010 |
| WO | 2010/005879 A1 | 1/2010 |
| WO | 2012/087938 A1 | 6/2012 |
| WO | 2014/106612 A1 | 7/2014 |

OTHER PUBLICATIONS

Balant et al. *Burger's Medicinal Chemistry and Drug Discovery*, 5th Ed., John Wiley & Sons, Inc., Hoboken, NJ, 1996, pp. 949-982.
Banker et al., *Modern Pharmaceutics*, 3d ed., Revised and Expanded, Marcel Dekker, Inc., New York, 1996, 451 and 596.
Bundgaard, Design of Prodrugs Elsevier science Publishers B.V. (Biomedical Division), Amsterdam, The Netherlands, 1985, Chapter 1, *Design of prodrugs: Bioreversible derivatives for various functional groups and chemical entities*, 3 pages.
English Translation of Office Action, dated Sep. 26, 2019, for Mexican Application No. MX/a/2016/006815, 3 pages.
Ettmayer et al., "Lessons Learned from Marketed and Investigational Prodrugs," *J. Med. Chem.* 47(10):2393-2404, 2004.
Hulikal, *Deutium Labeled Compounds in Drug Discovery Process*, Abstract, 2010, 1 page.
International Search Report and Written Opinion, dated May 26, 2015, for International Application No. PCT/US2014/067709, 10 pages.
Japanese Office Action, dated Jul. 3, 2018, for Japanese Application No. 2016-534735, 10 pages (With English Translation).
Jordan, "Tamoxifen: A Most Unlikely Pioneering Medicine," *Nature Reviews* 2:205-213, 2003.
Office Action, dated Jun. 15, 2018, for European Application No. 14 819 178.6, 5 pages.
Office Action, dated Jun. 25, 2019, for Indian Application No. 201617019865, 6 pages. (w/ English Translation).
Pimlott, "Radiotracer Development in Psychiatry," *Nucl. Med. Commun.* 26(3):183-8, 2005. (Abstract).
Silverman, *The Organic Chemistry of Drug Design and Drug Action*, Academic Press, Inc., San Diego, CA, 1992, Chapter 8, "Prodrugs and Drug Delivery Systems," pp. 352-400.
Stella, "Prodrugs as Therapeutics," *Expert Opin. Ther. Patents* 14(3):277-280, 2004.
Testa, "Prodrug research: futile or fertile?" *Biochemical Pharmacology* 68:2097-2106, 2004.
Traoré et al., "New aminopyrimidine derivatives as inhibitors of the TAM family," *European Journal of Medicinal Chemistry* 70:789-801, 2013.

*Primary Examiner* — Patricia L Morris
(74) *Attorney, Agent, or Firm* — Seed IP Law Group LLP

(57) ABSTRACT

Provided herein are aminopyridine derivatives and pharmaceutical compositions that are useful as TAM family kinase inhibitors.

4 Claims, No Drawings

AMINOPYRIDINE DERIVATIVES AS TAM FAMILY KINASE INHIBITORS

CROSS-REFERENCE TO RELATED APPLICATIONS

This application is a divisional application of U.S. application Ser. No. 16/254,208, filed Jan. 22, 2019 (now allowed), which is a divisional application of U.S. application Ser. No. 15/039,609, filed May 26, 2016, issued as U.S. Pat. No. 10,233,176, which is a 371 national phase application of International Application No. PCT/US2014/067709, filed Nov. 26, 2014, which claims the benefit under 35 U.S.C. § 119(e) of U.S. Provisional Patent Application No. 61/909,828, filed Nov. 27, 2013, and U.S. Provisional Patent Application No. 61/909,830, filed Nov. 27, 2013, which applications are incorporated herein by reference in their entirety.

BACKGROUND

Technical Field

The present disclosure provides compounds that inhibit protein kinases Tyro3, Axl and Mer (TAM family kinases), prodrugs of the compounds, intermediates and methods of synthesizing the compounds and/or prodrugs, pharmaceutical compositions comprising the compounds and/or prodrugs and methods of using the compounds and/or prodrugs in a variety of contexts, including, for example, in the treatment and/or prevention of various diseases that are responsive to TAM family kinase inhibition and/or that are mediated, at least in part, by abnormal TAM family kinase activity.

Description of the Related Art

The receptor tyrosine kinases (RTKs) are transmembrane proteins and function as sensors for extracellular ligands, which transduce signals from extracellular medium to the cytoplasm. Their activation leads to the recruitment, phosphorylation, and activation of the downstream signaling pathways, which ultimately regulate cellular functions such as proliferation, growth, differentiation or motility. Abnormal overexpression levels and/or enhanced activities of RTKs have been associated to a variety of human cancers, leading to a strong interest in the development of inhibitors against these human cancers. Tyro-3, Axl, and Mer constitute the TAM family of RTKs characterized by a conserved sequence within the kinase domain and adhesion molecule like extracellular domains. With varying degree of specificity and affinity, TAM kinases can be activated by the vitamin K-dependent ligand Gas6 and/or Protein S. Strong evidence supports their association with both cancer (gain-in-function) and autoimmunity (loss-of-function). TAM kinase signaling has been implicated in a myriad of cellular responses, many of which are the hallmarks of cancer, including proliferation, survival, migration, invasion and angiogenesis. In addition, TAM plays pivotal roles innate immunity through inhibiting inflammation in macrophages and dendritic cells and promoting the phagocytosis of apoptotic cells. While the oncogenic activity of TAM kinases appears to be mediated via PI3K/AKT pathway, the JAK-STAT pathway is critical for their roles in immune responses. Overexpression of TAM kinases has been observed in over 20 human cancers. The level of their expression was shown to correlate with shorter progression-free and overall survival and their up-regulation has been linked to cancer resistance to cytotoxic drugs and targeted therapies.

While broadly expressed in various human tumor cell lines, Tyro3, Axl, and Mer exhibit their respective tissue-specific expression patterns. Tyro-3 is highly expressed in the nervous system whereas, Axl is expressed ubiquitously. Higher level of Mer is often found in hematopoietic lineages such as monocytes/macrophages, dendritic cells, NK cells, NKT cells, megakaryocytes, and platelets.

Compared to Axl and Mer, Tyro3 is the least studied kinase of the TAM family. Implication of Tyro3 in tumorigenesis was only recently substantiated by recent studies, which revealed Tyro3 is a potential oncogene in melanoma that is linked to poorer outcome of patients suffering from melanoma regardless the BRAF or NRAS status by conferring survival advantage to melanoma cells. It was also identified as one of kinases significantly up-regulated in lung cancer by a phosphoproteomic screen. High level of Tyro3 expression has also been correlated with thyroid cancer.

As the founding member of the TAM kinase family, Axl was discovered as a transforming gene in chronic myelogenous leukemia (CIVIL). Axl overexpression has since been reported in a wide range of human malignancies and is associated with invasiveness and metastasis in lung, prostate, breast and pancreatic cancer. Axl is also an important regulator of breast cancer metastasis and EMT. Activation of the Axl kinase confers resistance to EGFR targeted therapy in lung cancer. Upregulation of Axl has been implicated as a mechanism of resistance to imatinib in CML and gastrointestinal stromal tumors and to lapatinib in breast cancer. Axl expression has also been associated with chemoresistance in AML, NSCLC and ovarian cancer.

Mer is overexpressed/over-activated in a wide variety of cancers and has been established as a therapeutic target in hematopoietic malignancies and solid tumors including leukemia, non-small cell lung cancer, glioblastoma, melanoma, prostate cancer, breast cancer, colon cancer, gastric cancer, pituitary adenomas, and rhabdomyosarcomas. Oncogenic potential of Mer is mediated through the activation of several canonical oncogenic signaling pathways including the mitogen-activated protein kinase and phosphoinositide 3-kinase pathways, as well as regulation of signal transducer and activator of transcription family members, migration-associated proteins including the focal adhesion kinase and myosin light chain 2, and prosurvival proteins such as survivin and Bcl-2. In neoplastic cells, these signaling events result in functional phenotypes such as decreased apoptosis, increased migration, chemoresistance, increased colony formation, and increased tumor formation in murine models. Conversely, Mer inhibition by genetic or pharmacologic means can reverse these pro-oncogenic phenotypes.

To date, the following literature reports described small molecule inhibitors of Tyro3, Axl and/or Mer: Zhang et al., *J. Med. Chem.,* 2014, 57, 7031-7041; Rho et al., *Cancer Res.,* 2014, 74, 253-262; Traoré et al., *Euro. J. Med. Chem.,* 2013, 70, 789-801; Zhang et al., *J. Med. Chem.,* 2013, 56, 9683-9692; Zhang et al., *J. Med. Chem.,* 2013, 56, 9693-9700; Liu et al., *Euro. J. Med. Chem.,* 2013, 65, 83-93; Powell et al., *Bioorg. Med. Chem. Lett.,* 2013, 23, 1051-1055; Powell et al., *Bioorg. Med. Chem. Lett.,* 2013, 23, 1046-1050; Suarez et al., *Euro. J. Med. Chem.,* 2013, 61, 2-25; M. F. Burbridge et al., *Mol. Cancer Ther.,* 2013, 12, 1749-1762; Powell et al., *Bioorg. Med. Chem. Lett.* 2012, 22, 190-193; Liu et al., *ACS Med. Chem. Lett.,* 2012, 3, 129-134; Mollard et al., *ACS Med. Chem. Lett.,* 2011, 2, 907-912; Holland et al., *Cancer Res.,* 2010, 70(4), 1544-1554; Ono et al., poster number MEDI-393, 244$^{th}$ ACS National Meeting & Exposition, Philadelphia, Pa., Aug. 19-23, 2012; Zhang et al., poster number MEDI-56, 244th ACS National Meeting & Exposition, Philadelphia, Pa., Aug. 19-23, 2012; Yang et al., poster number MEDI-265, 242nd ACS National Meeting & Exposition, Denver, Colo., Aug. 28-Sep. 1, 2011; Zhang et al., poster number MEDI-62, 242nd ACS National Meeting & Exposition, Denver, Colo., Aug. 28-Sep. 1, 2011; Wang et al., poster number MEDI-18, 242nd ACS National Meeting & Exposition, Denver, Colo., Aug. 28-Sep. 1, 2011; Huang et al., *J. Stru. Biol.* 2009, 165, 88-96. Axl inhibitors have also been disclosed in US2008188455A1; WO2007030680A2; WO2008045978A1; WO2008080134A2; WO2008083353A1; WO2008083354A1; WO2008083356A1; WO2008083357A1; WO2008083367A2; WO2008128072A2; WO2009007390A2; WO2009024825A1; WO2009047514A1; WO2009053737A2; WO2009054864A1; WO2009127417A1; WO2010005876A2; WO2010005879A1; WO2010083465A1; WO2010090764A1; WO2011045084A1; WO2011138751A2; WO2012028332A1; WO2012135800A1; WO2013074633A1; WO2013115280A1; WO2013162061A1.

SUMMARY

The present disclosure provides 2-aminopyridine derivatives that are capable of inhibiting the activity of TAM family kinases. Methods of using such derivatives to inhibit the activity of TAM family kinases and pharmaceutical compositions comprising such derivatives are also disclosed.

One embodiment provides compounds of formula (I):

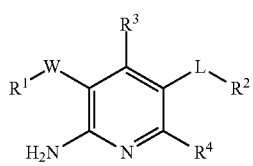

Formula (I)

wherein:
W is

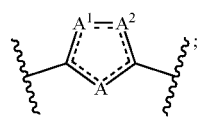

each A, $A^1$ and $A^2$ is the same or different and independently —N═, —$CR^5$═, or —O—;

L is heteroaryl, heterocyclyl, —N($R^6$)—, —O—, —C(O)—, —C(O)O—, —S(O)$_t$— where t is 0, 1, or 2, —CON($R^6$)—, —N($R^6$)CO—, —SO$_2$N($R^6$)—, or —N($R^6$)CON($R^6$)—, provided that when L is heteroaryl, L is not pyridinyl, pyrazinyl or thienyl;

$R^1$ is alkyl, cycloalkyl, cycloalkylalkyl, haloalkyl, aryl, aralkyl, heterocyclyl, heterocyclylalkyl, heteroaryl, or heteroarylalkyl;

$R^2$ is hydrogen, heterocyclyl, heterocyclylalkyl, cycloalkyl, alkyl, aralkyl, cycloalkylalkyl, heteroaryl, heteroarylalkyl, or aryl;

each $R^3$ and $R^4$ is the same or different and independently hydrogen, alkyl, aralkyl, alkenyl, aralkenyl, alkynyl, aralkynyl, cycloalkyl, cycloalkylalkyl, halo, or haloalkyl;

$R^5$, at each occurrence, is hydrogen, alkyl, aralkyl, cycloalkyl, cycloalkylalkyl, halo, or haloalkyl;

$R^6$ is hydrogen, alkyl, cycloalkyl, cycloalkylalkyl, or haloalkyl, a stereoisomer, enantiomer or tautomer thereof, an isotopically enriched derivative thereof, a pharmaceutically acceptable salt thereof, a pharmaceutical composition thereof or a prodrug thereof.

Of the compounds of Formula (I), an embodiment provides compound of Formula (IA):

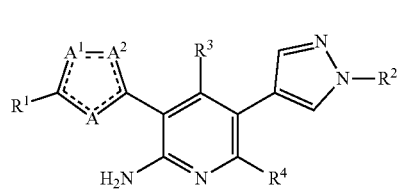

Formula (IA)

wherein,
A, $A^1$, $A^2$, $R^3$, and $R^4$ are as defined above.

Of the compounds of Formula (IA), an embodiment provides compounds of Formula (IA1):

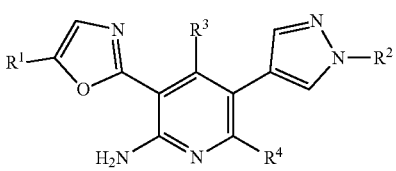

Formula (IA1)

wherein:
$R^1$, $R^2$, $R^3$, and $R^4$ are as defined above.

Of the compounds of Formula (IA), another embodiment provides compounds of Formula (IA2):

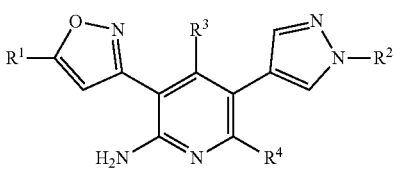

Formula (IA2)

wherein, $R^1$, $R^2$, $R^3$, and $R^4$ are as defined above.

Of the compounds of Formula (IA), another embodiment provides compounds of Formula (IA3):

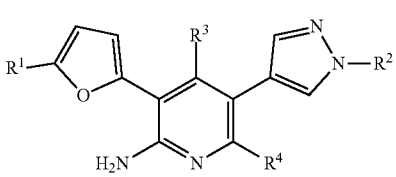

Formula (IA3)

wherein, $R^1$, $R^2$, $R^3$, and $R^4$ are as defined above.

Of the compounds of Formula (IA), another embodiment provides compounds of Formula (IA4):

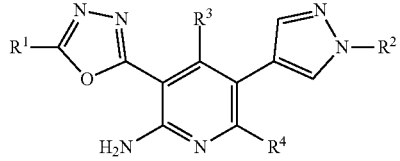

Formula (IA4)

wherein, $R^1$, $R^2$, $R^3$, and $R^4$ are as defined above.

Of the compounds of Formula (IA), another embodiment provides compounds of Formula (IA5):

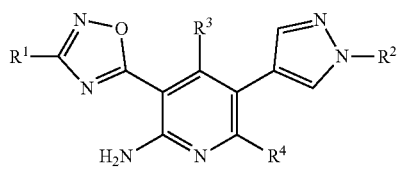

Formula (IA5)

wherein, $R^1$, $R^2$, $R^3$, and $R^4$ are as defined above.

Of the compounds of Formula (IA), another embodiment provides compounds of Formula (IA6):

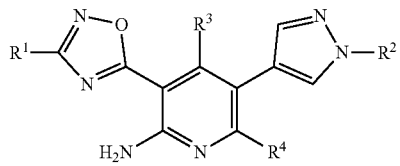

Formula (IA6)

wherein, $R^1$, $R^2$, $R^3$, and $R^4$ are as defined above.

Of the compounds of Formula (IA), another embodiment provides compounds of Formula (IA7):

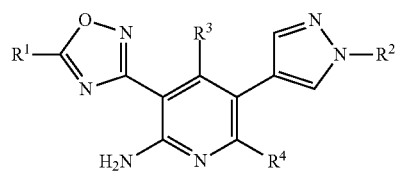

Formula (IA7)

wherein, $R^1$, $R^2$, $R^3$, and $R^4$ are as defined above.

Of the compounds of Formula (I), an embodiment provides compound of Formula (IB):

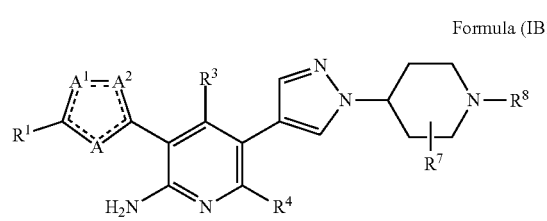

Formula (IB)

wherein,
A, $A^1$, $A^2$, $R^1$, $R^3$, $R^4$, and $R^5$ are as defined above,
L is heteroaryl or heterocycle;
$R^7$ is hydrogen, alkyl, alkoxy, or halo;
X is —O—, —$NR^8$—, or —$C(R^9)_2$—;
$R^8$ is hydrogen, alkyl, or —$C(O)R^{10}$—;
each $R^9$ is independently hydrogen, alkyl, alkoxy, or halo; and
$R^{10}$ is alkyl, cycloalkyl, aryl, alkoxy, or aralkyl.

Of the compounds of Formula (IB), an embodiment provides compound of Formula (IB1):

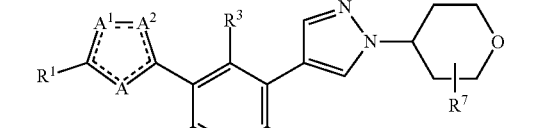

Formula (IB1)

wherein,
A, $A^1$, $A^2$, $R^1$, $R^3$, $R^4$, $R^7$, and $R^8$ are as defined above.

Of the compounds of Formula (IB), an embodiment provides compound of Formula (IB2):

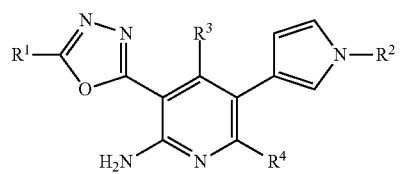

Formula (IB2)

wherein,
A, $A^1$, $A^2$, $R^1$, $R^3$, $R^4$, and $R^7$ are as defined above.

Of the compounds of Formula (IB), an embodiment provides compound of Formula (IB3):

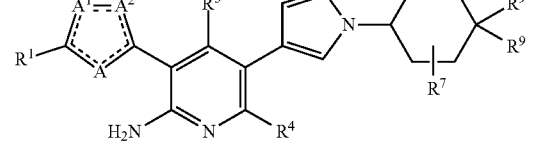

Formula (IB3)

wherein,
A, $A^1$, $A^2$, $R^3$, $R^4$, $R^7$, and $R^9$ are as defined above.

Yet another embodiment provides a pharmaceutical composition of a compound of any one of Formula (I), (IA), or (IB), or any one of the substructures as represented by Formula (IA1), (IA2), (IA3), (IA4), (IA5), (IA6), (IA7), (IB1), (IB2), or (IB3), or any one the specific compounds disclosed herein.

Yet another embodiment provides a method of treating leukemia and lymphoma comprising administering to a subject in need thereof a pharmaceutically effective amount of a compound of Formula (I), (IA), or (IB), or any one of the substructures as represented by Formula (IA1), (IA2), (IA3), (IA4), (IA5), (IA6), (IA7), (IB1), (IB2), or (IB3) or a pharmaceutical composition comprising the same.

Yet another embodiment provides a method of treating endometriosis comprising administering to a subject in need thereof a pharmaceutically effective amount of a compound of a compound of Formula (I), (IA), or (IB), or any one of the substructures as represented by Formula (IA1), (IA2), (IA3), (IA4), (IA5), (IA6), (IA7), (IB1), (IB2), or (IB3) or a pharmaceutical composition comprising the same.

Yet another embodiment provides a method of treating restenosis comprising administering to a subject in need thereof a pharmaceutically effective amount of a compound of a compound of Formula (I), (IA), or (IB), or any one of the substructures as represented by Formula (IA1), (IA2), (IA3), (IA4), (IA5), (IA6), (IA7), (IB1), (IB2), or (IB3) or a pharmaceutical composition comprising the same.

Yet another embodiment provides a method of treating atherosclerosis/thrombosis comprising administering to a subject in need thereof a pharmaceutically effective amount of a compound of a compound of Formula (I), (IA), or (IB), or any one of the substructures as represented by Formula (IA1), (IA2), (IA3), (IA4), (IA5), (IA6), (IA7), (IB1), (IB2), or (IB3) or a pharmaceutical composition comprising the same.

Yet another embodiment provides a method of treating psoriasis comprising administering to a subject in need thereof a pharmaceutically effective amount of a compound of Formula (I), (IA), or (IB), or any one of the substructures as represented by Formula (IA1), (IA2), (IA3), (IA4), (IA5), (IA6), (IA7), (IB1), (IB2), or (IB3) or a pharmaceutical composition comprising the same.

Yet another embodiment provides a method of treating age-related macular degeneration or diabetic retinopathy comprising administering to a subject in need thereof a pharmaceutically effective amount of a compound of Formula (I), (IA), or (IB), or any one of the substructures as represented by Formula (IA1), (IA2), (IA3), (IA4), (IA5), (IA6), (IA7), (IB1), (IB2), or (IB3) or a pharmaceutical composition comprising the same.

Yet another embodiment provides a method of treating retinopathy of prematurity comprising administering to a subject in need thereof a pharmaceutically effective amount of a compound of Formula (I), (IA), or (IB), or any one of the substructures as represented by Formula (IA1), (IA2), (IA3), (IA4), (IA5), (IA6), (IA7), (IB1), (IB2), or (IB3) or a pharmaceutical composition comprising the same.

Yet another embodiment provides a method of treating renal transplant rejection comprising administering to a subject in need thereof a pharmaceutically effective amount of a compound of Formula (I), (IA), or (IB), or any one of the substructures as represented by Formula (IA1), (IA2), (IA3), (IA4), (IA5), (IA6), (IA7), (IB1), (IB2), or (IB3) or a pharmaceutical composition comprising the same.

Yet another embodiment provides a method of treating rheumatoid arthritis comprising administering to a subject in need thereof a pharmaceutically effective amount of a compound of Formula (I), (IA), or (IB), or any one of the substructures as represented by Formula (IA1), (IA2), (IA3), (IA4), (IA5), (IA6), (IA7), (IB1), (IB2), or (IB3) or a pharmaceutical composition comprising the same.

Yet another embodiment provides a method of treating osteoarthritis comprising administering to a subject in need thereof a pharmaceutically effective amount of a compound of a compound of Formula (I), (IA), or (IB), or any one of the substructures as represented by Formula (IA1), (IA2), (IA3), (IA4), (IA5), (IA6), (IA7), (IB1), (IB2), or (IB3) or a pharmaceutical composition comprising the same.

Yet another embodiment provides a method of treating osteoporosis comprising administering to a subject in need thereof a pharmaceutically effective amount of a compound of Formula (I), (IA), or (IB), or any one of the substructures as represented by Formula (IA1), (IA2), (IA3), (IA4), (IA5), (IA6), (IA7), (IB1), (IB2), or (IB3) or a pharmaceutical composition comprising the same.

Yet another embodiment provides a method of treating cataracts comprising administering to a subject in need thereof a pharmaceutically effective amount of a compound of a compound of Formula (I), (IA), or (IB), or any one of the substructures as represented by Formula (IA1), (IA2), (IA3), (IA4), (IA5), (IA6), (IA7), (IB1), (IB2), or (IB3) or a pharmaceutical composition comprising the same.

Yet another embodiment provides a method of preventing/treating tumor metastasis or treating metastasized tumors comprising administering to a subject in need thereof a pharmaceutically effective amount of a compound of a compound of Formula (I), (IA), or (IB), or any one of the substructures as represented by Formula (IA1), (IA2), (IA3), (IA4), (IA5), (IA6), (IA7), (IB1), (IB2), or (IB3) or a pharmaceutical composition comprising the same.

DETAILED DESCRIPTION

Definitions

Certain chemical groups named herein are preceded by a shorthand notation indicating the total number of carbon atoms that are to be found in the indicated chemical group. For example; $C_7$-$C_{12}$alkyl describes an alkyl group, as defined below, having a total of 7 to 12 carbon atoms, and $C_4$-$C_{12}$cycloalkylalkyl describes a cycloalkylalkyl group, as defined below, having a total of 4 to 12 carbon atoms. The total number of carbons in the shorthand notation does not include carbons that may exist in substituents of the group described.

Accordingly, as used in the specification and appended claims, unless specified to the contrary, the following terms have the meaning indicated:

"Amino" refers to the —$NH_2$ radical.

"Methoxy" refers to the —$OCH_3$ radical.

"Cyano" refers to the —CN radical.

"Nitro" refers to the —$NO_2$ radical.

"Trifluoromethyl" refers to the —$CF_3$ radical.

"Oxo" refers to the =O.

"Thioxo" refers to the =S.

"Acyl" refers to —$C(O)R^{14}$ radical, wherein $R^{14}$ is hydrogen, alkyl, haloalkyl, cycloalkyl, cycloalkylalkyl, aryl, aralkyl, heterocyclyl, heterocyclylalkyl, heteroaryl or heteroarylalkyl;

"Alkyl" refers to a straight or branched hydrocarbon chain radical, when unsubstituted, consisting solely of carbon and hydrogen atoms, containing no unsaturation, having from one to twelve carbon atoms, preferably one to eight carbon atoms or one to six carbon atoms, and which is attached to the rest of the molecule by a single bond, e.g., methyl, ethyl, n-propyl, 1-methylethyl (iso-propyl), n-butyl, n-pentyl, 1,1-dimethylethyl (t-butyl), and the like. Unless stated otherwise specifically in the specification, an alkyl group may be optionally substituted by one or more substituents, as defined herein. "Alkenyl" refers to a straight or branched hydrocarbon chain radical group, when unsubstituted, consisting solely of carbon and hydrogen atoms, containing at least one double bond, having from two to twelve carbon atoms, preferably one to eight carbon atoms and which is attached to the rest of the molecule by a single bond, e.g., ethenyl, prop-1-enyl, but-1-enyl, pent-1-enyl, penta-1,4-dienyl, and the like. Unless stated otherwise specifically in the specification, an alkenyl group may be optionally substituted by one of or more substituents, as defined herein.

"Alkynyl" refers to a straight or branched hydrocarbon chain radical group, when unsubstituted, consisting solely of carbon and hydrogen atoms, containing at least one triple bond, optionally containing at least one double bond, having from two to twelve carbon atoms, preferably one to eight carbon atoms and which is attached to the rest of the molecule by a single bond, for example, ethynyl, propynyl, butynyl, pentynyl, hexynyl, and the like. Unless stated otherwise specifically in the specification, an alkynyl group may be optionally substituted by one or more substituents, as defined herein. "Alkylene" and "alkylene chain" refer to a straight or branched divalent hydrocarbon chain, linking the rest of the molecule to a radical group, consisting solely of carbon and hydrogen, containing no unsaturation and having from one to twelve carbon atoms, preferably having from one to eight carbons, e.g., methylene, ethylene, propylene, n-butylene, and the like. The alkylene chain may be attached to the rest of the molecule and to the radical group through one carbon within the chain or through any two carbons within the chain.

"Alkenylene" and "alkenylene chain" refer to a straight or branched divalent hydrocarbon chain linking the rest of the molecule to a radical group, consisting solely of carbon and hydrogen, containing at least one double bond and having from two to twelve carbon atoms, e.g., ethenylene, propenylene, n-butenylene, and the like. The alkenylene chain is attached to the rest of the molecule through a single bond and to the radical group through a double bond or a single bond. The points of attachment of the alkenylene chain to the rest of the molecule and to the radical group can be through one carbon or any two carbons within the chain.

"Alkoxy" refers to a radical of the formula —$OR_a$ where $R_a$ is an alkyl radical as defined above. The alkyl part of the alkoxy radical may be optionally substituted as defined above for an alkyl radical.

"Aryl" refers to aromatic monocyclic or multi-cyclic hydrocarbon ring system, when unsubstituted, consisting only of hydrogen and carbon and containing from 6 to 19 carbon atoms, preferably 6 to 10 carbon atoms, where the ring system may be partially or fully saturated. Aryl groups include, but are not limited to groups such as fluorenyl, phenyl and naphthyl. Unless stated otherwise specifically in the specification, the term "aryl" or the prefix "ar-" (such as in "aralkyl") is meant to include aryl radicals optionally substituted by one or more substituents, as defined herein. "Aralkyl" refers to a radical of the formula —$R_aR_b$ where $R_a$ is an alkyl radical as defined above and $R_b$ is one or more aryl radicals as defined above, e.g., benzyl, diphenylmethyl and the like. The aryl part of the aralkyl radical may be optionally substituted as described above for an aryl group. The alkyl part of the aralkyl radical may be optionally substituted as defined above for an alkyl group.

"Aralkenyl" refers to a radical of the formula —$R_cR_b$ where $R_c$ is an alkenyl radical as defined above and $R_b$ is one or more aryl radicals as defined above, which may be optionally substituted as described above. The aryl part of the aralkenyl radical may be optionally substituted as described above for an aryl group. The alkenyl part of the aralkenyl radical may be optionally substituted as defined above for an alkenyl group.

"Aralkynyl" refers to a radical of the formula —$R_dR_b$ where $R_d$ is an alkynyl radical as defined above and $R_b$ is one or more aryl radicals as defined above. The aryl part of the aralkynyl radical may be optionally substituted as described above for an aryl group. The alkynyl part of the aralkynyl radical may be optionally substituted as defined above for an alkynyl group.

"Cycloalkyl" refers to a stable non-aromatic monocyclic or bicyclic hydrocarbon radical, when unsubstituted, consisting solely of carbon and hydrogen atoms, having from three to fifteen carbon atoms, preferably having from three to twelve carbon atoms, and which is saturated or unsaturated and attached to the rest of the molecule by a single bond, e.g., cyclopropyl, cyclobutyl, cyclopentyl, cyclohexyl, decalinyl and the like. Unless otherwise stated specifically in the specification, the term "cycloalkyl" is meant to include cycloalkyl radicals which are optionally substituted by one or more substituents, as defined herein. "Cycloalkylalkyl" refers to a radical of the formula —$R_aR_d$ where $R_a$ is an alkyl radical as defined above and $R_d$ is a cycloalkyl radical as defined above. The cycloalkyl part of the cycloalkyl radical may be optionally substituted as defined above for a cycloalkyl radical. The alkyl part of the cycloalkyl radical may be optionally substituted as defined above for an alkyl radical.

"Halo" refers to bromo, chloro, fluoro or iodo.

"Haloalkyl" refers to an alkyl radical, as defined above, that is substituted by one or more halo radicals, as defined above. One or more carbons of the alkyl radical may be substituted by the one or more halo radicals. Examples of haloalkyl include, trifluoromethyl, difluoromethyl, trichloromethyl, 2,2,2-trifluoroethyl, 1-fluoromethyl-2-fluoroethyl, 3-bromo-2-fluoro-propyl, 1-bromomethyl-2-bromoethyl, and the like. The alkyl part of the haloalkyl radical may be optionally substituted as defined above for an alkyl group.

"Haloalkenyl" refers to an alkenyl radical, as defined above, that is substituted by one or more halo radicals, as defined above, e.g., 2-bromoethenyl, 3-bromoprop-1-enyl, and the like. The alkenyl part of the haloalkenyl radical may be optionally substituted as defined above for an alkyl group.

"Heterocyclyl" refers to a stable 3- to 18-membered non-aromatic ring radical including, as ring atoms, at least one carbon atom and from one to five heteroatoms selected from the group consisting of nitrogen, oxygen and sulfur. For purposes of this disclosure, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; and the nitrogen atom may be optionally quaternized; and the heterocyclyl radical may be partially or fully saturated. Examples of such heterocyclyl radicals include, but are not limited to, dioxolanyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, the term "heterocyclyl" is meant to include heterocyclyl radicals as defined above which are optionally substituted by one or more substituents, as defined herein.

When the heterocyclyl is a substituent of another moiety, the heterocyclyl is monovalent, which means that the heterocyclyl is connected to the other moiety by a single ring atom. An example of a monovalent heterocyclyl can be found in the radical of heterocyclylalkyl, in which a heterocyclyl group is a substituent of an alkyl group. When heterocyclyl is a linker moiety (L) of Formula (I), the heterocyclyl is a divalent radical. In this occurrence, the heterocyclyl (as L) is linked, by two of its ring atoms, to the 2-aminopyridine moiety and $R^2$ of Formula (I). An example of a divalent heterocyclyl is 1,4-piperidinyl, shown below:

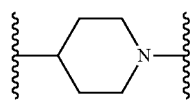

"Heterocyclylalkyl" refers to a radical of the formula —$R_aR_e$ where $R_a$ is an alkyl radical as defined above and $R_e$ is a heterocyclyl radical as defined above, and if the heterocyclyl is a nitrogen-containing heterocyclyl, the heterocyclyl may be attached to the alkyl radical at the nitrogen atom. The alkyl part of the heterocyclylalkyl radical may be optionally substituted as defined above for an alkyl group. The heterocyclyl part of the heterocyclylalkyl radical may be optionally substituted as defined above for a heterocyclyl group.

"Heteroaryl" refers to a 5- to 18-membered aromatic ring radical including, as ring atoms, at least one carbon atom and from one to five heteroatoms selected from the group consisting of nitrogen, oxygen and sulfur. For purposes of this disclosure, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; and the nitrogen atom may be optionally quaternized. Examples include, but are not limited to, azepinyl, acridinyl, benzimidazolyl, benzthiazolyl, benzindolyl, benzothiadiazolyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, furanyl, furanonyl, isothiazolyl, imidazolyl, indolyl, indazolyl, isoindolyl, indolinyl, isoindolinyl, indolizinyl, isoxazolyl, naphthyridinyl, oxadiazolyl, 2-oxoazepinyl, oxazolyl, oxiranyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, thiazolyl, thiadiazolyl, triazolyl, tetrazolyl, triazinyl, and thiophenyl. Unless stated otherwise specifically in the specification, the term "heteroaryl" is meant to include heteroaryl radicals as defined above which are optionally substituted by one or more substituents, as defined herein. Heteroaryl, as defined herein, may be monovalent or divalent. When heteroaryl is a substituent of another moiety, the heteroaryl is monovalent, which means that the heteroaryl is connected to the other moiety by a single ring atom. An example of a monovalent heteroaryl can be found in the radical of heteroarylalkyl, in which an alkyl group is substituted with a heteroaryl group. When heteroaryl is a linker moiety (L) of Formula (I), the heteroaryl is a divalent radical. In this occurrence, the heteroaryl (as L) is linked, by two of its ring atoms, to the 2-aminopyridine moiety and $R^2$ of Formula (I). An example of a divalent heteroaryl is 1H-pyrazol-4-yl, shown below:

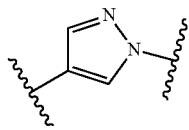 [SMILES: *c1cnn(*)c1]

"Heteroarylalkyl" refers to a radical of the formula —$R_aR_f$ where $R_a$ is an alkyl radical as defined above and $R_f$ is a heteroaryl radical as defined above. The heteroaryl part of the heteroarylalkyl radical may be optionally substituted as defined above for a heteroaryl group. The alkyl part of the heteroarylalkyl radical may be optionally substituted as defined above for an alkyl group.

"Heteroarylalkenyl" refers to a radical of the formula —$R_cR_g$ where $R_c$ is an alkenyl radical as defined above and $R_g$ is a heteroaryl radical as defined above. The heteroaryl part of the heteroarylalkenyl radical may be optionally substituted as defined above for a heteroaryl group. The alkenyl part of the heteroarylalkenyl radical may be optionally substituted as defined above for an alkenyl group.

"N-heteroaryl" is a subset of heteroaryl, and refers to a heteroaryl having at least one nitrogen ring atom. Heteroaryl is otherwise as defined as herein. Examples of N-heteroaryls include, without limitation, benzimidazolyl, benzindolyl, benzotriazolyl, benzo[4,6]imidazo[1,2-a]pyridinyl, carbazolyl, cinnolinyl, imidazolyl, indolyl, indazolyl, isoindolyl, indolinyl, isoindolinyl, indolizinyl, isoxazolyl, naphthyridinyl, oxadiazolyl, 2-oxoazepinyl, oxazolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, thiazolyl, thiadiazolyl, triazolyl, tetrazolyl, and triazinyl.

"N-heterocyclyl" is a subset of heterocyclyl, and refers to a heterocyclyl having at least one nitrogen ring atom. Heterocyclyl is otherwise as defined as herein. Examples of N-heterocyclyls include, without limitation, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, thiazolidinyl, thiomorpholinyl, thiamorpholinyl, 1-oxo-thiomorpholinyl, and 1,1-dioxo-thiomorpholinyl.

"Substituent" refers to a radical (a single non-hydrogen atom or a functional group) that is or can be bonded to another molecule. An substituent is therefore any one of the following radicals: alkyl, alkenyl, amino, halo, haloalkyl, haloalkenyl, cyano, oxo, thioxo, nitro, aryl, aralkyl, cycloalkyl, cycloalkylalkyl, heterocyclyl, heterocyclylalkyl, heteroaryl, heteroarylalkyl, —$OR^{14}$, —$OC(O)R^{14}$, —$N(R^{14})_2$, —$C(O)R^{14}$, —$C(O)OR^{14}$, —$C(O)N(R^{14})_2$, —$N(R^{14})C(O)OR^{16}$, —$N(R^{14})C(O)R^{16}$, —$N(R^{14})(S(O)_tR^{16})$ (where t is 1 to 2), —$S(O)_tOR^{16}$ (where t is 1 to 2), —$S(O)_tR^{16}$ (where t is 0 to 2), and —$S(O)_tN(R^{14})_2$ (where t is 1 to 2) where each $R^{14}$ is independently hydrogen, alkyl, haloalkyl, cycloalkyl, cycloalkylalkyl, aryl (optionally substituted with one or more halo groups), aralkyl, heterocyclyl, heterocyclylalkyl, heteroaryl or heteroarylalkyl; and each $R^{16}$ is alkyl, haloalkyl, cycloalkyl, cycloalkylalkyl, aryl, aralkyl, heterocyclyl, heterocyclylalkyl, heteroaryl or heteroarylalkyl, and where each of the above substituents is unsubstituted unless otherwise indicated.

"Prodrugs" refers to a compound that may be converted under physiological conditions or by solvolysis to a biologically active compound of Formula (I) or any one of the substructures. Thus, the term "prodrug" refers to a metabolic precursor of a compound of Formula (I) or any one of the substructures, that is pharmaceutically acceptable; the latter is also referred to as a "parent compound." A prodrug may be inactive when administered to a subject in need thereof, but is converted in vivo to an active compound, i.e., the parent compound. Prodrugs are typically rapidly transformed in vivo to yield the parent compound, for example, by hydrolysis in blood. The prodrug compound often offers advantages of solubility, tissue compatibility or delayed release in a mammalian organism (see, Bundgard, H., Design of Prodrugs (1985), pp. 7-9, 21-24, Elsevier, Amsterdam).

A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein.

The term "prodrug" is also meant to include any covalently bonded carriers which release the active compound of the disclosure in vivo when such prodrug is administered to a mammalian subject. Prodrugs of a compound of the disclosure may be prepared by modifying functional groups present in the compound of Formula (I) or any one of the substructures in such a way that the modifications are cleaved, either in routine manipulation or in vivo, to the parent compound. Prodrugs include compounds of the disclosure wherein a hydroxy, amino or mercapto group is bonded to any group that, when the prodrug disclosure is administered to a mammalian subject, cleaves to restore the free hydroxy, free amino or free mercapto group, respectively. Examples of prodrugs include, but are not limited to, acetate, formate and benzoate, and phosphate derivatives of alcohol or amine functional groups in the compounds of Formula (I), (IA), (IB) or any one of the substructures.

"Stable compound" and "stable structure" are meant to indicate a compound that is sufficiently robust to survive isolation to a useful degree of purity from a reaction mixture, and formulation into an efficacious therapeutic agent.

"Mammal" or "mammalian subject" includes humans and domestic animals, such as cats, dogs, swine, cattle, sheep, goats, horses, rabbits, and the like.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable acid addition salt" refers to those salts which retain the biological effectiveness and properties of the free bases, which are not biologically or otherwise undesirable, and which are formed with inorganic acids such as, but not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Often crystallizations produce a solvate of the compound of the disclosure. As used herein, the term "solvate" refers to an aggregate that comprises one or more molecules of a compound of the disclosure with one or more molecules of solvent. The solvent may be water, in which case the solvate may be a hydrate. Alternatively, the solvent may be an organic solvent. Thus, the compounds of the present disclosure may exist as a hydrate, including a monohydrate, dihydrate, hemihydrate, sesquihydrate, trihydrate, tetrahydrate and the like, as well as the corresponding solvated forms. The compound of the disclosure may be true solvates, while in other cases, the compound of the disclosure may merely retain adventitious water or be a mixture of water plus some adventitious solvent.

A "pharmaceutical composition" refers to a formulation of a compound of the disclosure and a medium generally accepted in the art for the delivery of the biologically active compound to mammals, e.g., humans. Such a medium includes all pharmaceutically acceptable carriers, diluents or excipients therefor.

"Therapeutically effective amount" refers to that amount of a compound of the disclosure which, when administered to a mammal, preferably a human, is sufficient to effect treatment, as defined below, of a disease or condition in the mammal, preferably a human. The amount of a compound of the disclosure which constitutes a "therapeutically effective amount" will vary depending on the compound, the condition and its severity, and the age of the mammal to be treated, but can be determined routinely by one of ordinary skill in the art having regard to his own knowledge and to this disclosure.

"Treating" or "treatment" as used herein covers the treatment of the disease or condition of interest in a mammal, preferably a human, having the disease or disorder of interest, and includes:

(i) preventing the disease or condition from occurring in a mammal, in particular, when such mammal is predisposed to the condition but has not yet been diagnosed as having it;

(ii) inhibiting the disease or condition, i.e., arresting its development; or (iii) relieving the disease or condition, i.e., causing regression of the disease or condition.

As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

The compounds of the disclosure, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)-for amino acids. The present disclosure is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, such as HPLC using a chiral column. When the compounds described herein contain olefinic double bonds or other centers of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present disclosure contemplates various stereoisomers and mixtures thereof and includes "enantiomers", which refers to two stereoisomers whose molecules are non-superimposeable mirror images of one another.

A "tautomer" refers to a proton shift from one atom of a molecule to another atom of the same molecule. The present disclosure includes tautomers of any said compounds.

An "isotopically enriched derivative" refers to a compound wherein one or more atoms are replaced by atoms having the same atomic number but an atomic mass or mass number different from the atomic mass or mass number usually found in nature. Examples of isotopes suitable for inclusion in the compounds of the disclosure comprises isotopes of hydrogen, such as $^2H$ and $^3H$, carbon, such as $^{11}C$, $^{13}C$ and $^{14}C$, chlorine, such as $^{38}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{31}P$, $^{32}P$ and $^{33}P$, and sulphur, such as $^{35}S$. Substitution with heavier isotopes such as deuterium, i.e. $^2H$, may afford certain therapeutic advantages resulting from greater metabolic stability, for example, increased in vivo half-life or reduced dosage requirements and hence may be preferred in some circumstances. Isotopically-enriched compounds of the disclosure can generally be prepared by conventional techniques known to those skilled in the art or by processes analogous to those described in the accompanying Examples and Preparations Sections using an appropriate isotopically-enriched reagent in place of the non-enriched reagent previously employed.

Where a bond is shown as a dashed line ( - - - ), it is understood that the location allows for the possibility of a double bond. For example, the structure of the linker W is shown as:

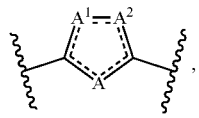

in which each dash bond may, but not necessarily, indicate the presence of a double bond. For instance, when A is —NH═, A is connected to the two adjacent carbon atoms by a single bond and a double bond, respectively. On the other hand, if A is defined as —O—, A is connected to the two adjacent carbon atoms by single bonds, respectively. The location and number of the double bonds in a given ring structure of W should satisfy the valence requirement, as would be recognized by a skilled person in the art.

The chemical naming protocol and structure diagrams used herein employ and rely the chemical naming features as utilized by Chemdraw version 12.0.2.1076 (available from Cambridgesoft Corp., Cambridge, Mass.). For complex chemical names employed herein, a substituent group is named before the group to which it attaches. For example, cyclopropylethyl comprises an ethyl backbone with cyclopropyl substituent. In chemical structure diagrams, all bonds are identified, except for some carbon atoms which are assumed to be bonded to sufficient hydrogen atoms to complete the valency.

For example, a compound of formula (I), as set forth above in the Summary of this disclosure, where W is a divalent oxazolyl moiety connected to the 2-aminopyridine moiety and the $R^1$ group at 2 and 5 positions:

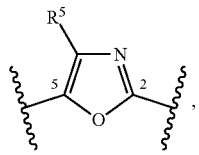

L is 1H-pyrazol-4-yl, $R^1$ is 4-chlorophenyl, $R^2$ is 1-(piperidin-4-yl), $R^3$, $R^4$ and $R^5$ are each hydrogen, i.e., a compound of the following formula:

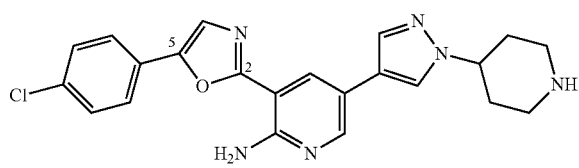 [SMILES: Nc1ncc(-c2cnn(C3CCNCC3)c2)cc1-c1ncc(-c2ccc(Cl)cc2)o1]

is named herein as: 3-(5-(4-chlorophenyl)oxazol-2-yl)-5-(1-(piperidin-4-yl)-1H-pyrazol-4-yl)pyridin-2-amine.

It should be note that there are two possible ways for W to connect with the 2-aminopyridine moiety and the $R^1$ group, namely, the oxazolyl may be connected at its 2 position to the 2-aminopyridine moiety, as shown above; or the oxazolyl may be connected at its 5 position to the 2-aminopyridine moiety. Thus, the following compound is also encompassed by Formula (I), when L is 1H-pyrazol-4-yl, $R^1$ is 4-chlorophenyl, $R^2$ is 1-(piperidin-4-yl), and $R^3$, $R^4$ and $R^5$ are hydrogens:

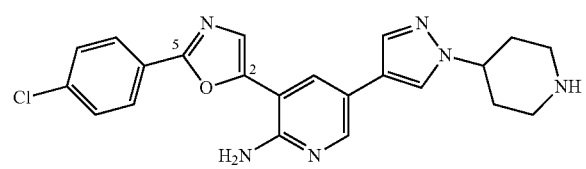 [SMILES: Nc1ncc(-c2cnn(C3CCNCC3)c2)cc1-c1cnc(-c2ccc(Cl)cc2)o1]

Similarly, the linker L, which is a divalent radical, may also have two possible ways to connect the 2-aminopyridine and the $R^2$ group. For instance, when L is an amido linker, i.e., —CON($R^6$)—, a compound of Formula (I) may have the carbonyl portion directly connected to the 2-aminopyridine moiety. Another compound of Formula (I) may have the carbonyl portion directly connected to the $R^2$ group.

As another example, a compound of formula (I), as set forth above in the Summary of this disclosure, where W is a divalent 1,3,4-oxadiazolyl moiety connected to the 2-aminopyridine moiety and the $R^1$ group at 2 and 5 positions:

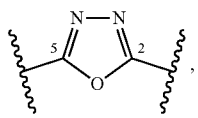

L is 1H-pyrazol-4-yl, $R^1$ is 2,6-dichlorophenyl, $R^2$ is 1-(piperidin-4-yl), $R^3$ and $R^4$ are each hydrogen, i.e., a compound of the following formula:

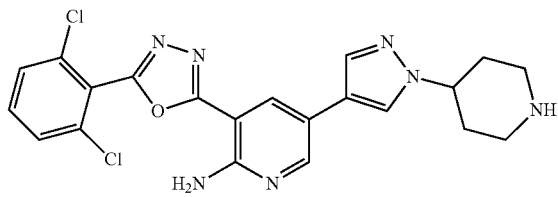 [SMILES: Nc1ncc(-c2cnn(C3CCNCC3)c2)cc1-c1nnc(-c2c(Cl)cccc2Cl)o1]

is named herein as: 3-(5-(2,6-dichlorophenyl)-1,3,4-oxadiazol-2-yl)-5-(1-(piperidin-4-yl)-1H-pyrazol-4-yl)pyridin-2-amine.

Embodiments

Provided herein are aminopyridine derivatives useful as TAM family kinase inhibitors. One embodiment provides a compound of formula (I):

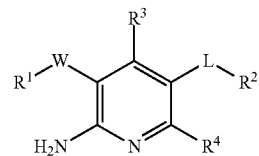

Formula (I)

wherein:
W is

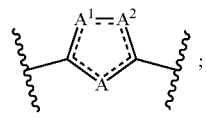

;

each A, $A^1$ and $A^2$ is the same or different and independently —N═, —$CR^5$═, or —O—;

L is a heteroaryl, heterocyclyl, —N($R^6$)—, —O—, —C(O)—, —C(O)O—, —S(O)$_t$— where t is 0, 1, or 2, —CON($R^6$)—, —N($R^6$)CO—, —SO$_2$N($R^6$)—, or —N($R^6$)CON($R^6$)—; provided that when L is heteroaryl, L is not pyridinyl, pyrazinyl or thienyl;

$R^1$ is alkyl, cycloalkyl, cycloalkylalkyl, haloalkyl, aryl, aralkyl, heterocyclyl, heterocyclylalkyl, heteroaryl, or heteroarylalkyl;

$R^2$ is hydrogen, heterocyclyl, heterocyclylalkyl, cycloalkyl, alkyl, aralkyl, cycloalkylalkyl, heteroaryl, heteroarylalkyl, or aryl;

each $R^3$ and $R^4$ is the same or different and independently selected from hydrogen, alkyl, aralkyl, alkenyl, aralkenyl, alkynyl, aralkynyl, cycloalkyl, cycloalkylalkyl, halo, and haloalkyl;

$R^5$, at each occurrence, is hydrogen, alkyl, aralkyl, cycloalkyl, cycloalkylalkyl, halo, or haloalkyl;

$R^6$ is hydrogen, alkyl, cycloalkyl, cycloalkylalkyl, or haloalkyl, a stereoisomer, enantiomer or tautomer thereof, an isotopically enriched derivative thereof, a pharmaceutically acceptable salt thereof, a pharmaceutical composition thereof or a prodrug thereof.

In a further embodiment, L is heteroaryl.

In yet another embodiment, L is N-heteroaryl.

In yet another embodiment, L is divalent pyrrozolyl moiety. In a specific embodiment, L is 1H-pyrazol-4-yl, and the compound of Formula (I) is represented by Formula (IA):

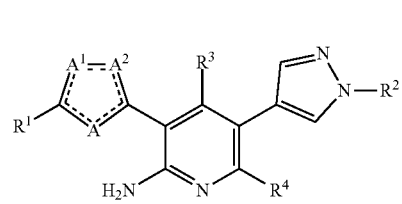

Formula (IA)

wherein,
A, $A^1$, $A^2$, $R^1$, $R^3$, and $R^4$ are as defined above.

Of the compounds of Formula (IA), an embodiment provides compounds of Formula (IA1):

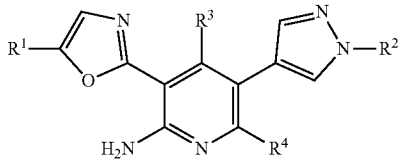

Formula (IA1)

wherein:
R¹, R², R³, and R⁴ are as defined above.

In more specific embodiments of Formula (IA1), R¹ is aryl, heteroaryl, cycloalkyl or heterocyclyl.

In a more specific embodiment of Formula (IA1), R¹ is aryl. More specifically, R¹ is a phenyl or substituted phenyl.

In other embodiments of Formula (IA1), R² is aryl, heteroaryl, cycloalkyl or heterocyclyl.

In a more specific embodiment of Formula (IA1), R² is heterocyclyl.

In more specific embodiments of Formula (IA1), R² is N-heterocyclyl.

More specifically, R² is piperidinyl or substituted piperidinyl.

In other more specific embodiments of Formula (IA1), R² is tetrahydropyranyl.

In another more specific embodiment of Formula (IA1), R² is cyclohexyl.

In certain specific embodiments of Formula (IA1), each of R³ and R⁴ is hydrogen, R¹ is aryl, R² is heterocyclyl.

In certain specific embodiments of Formula (IA1), each of R³ and R⁴ is hydrogen, R¹ is phenyl or substituted phenyl, R² is heterocyclyl.

In certain specific embodiments of Formula (IA1), each of R³ and R⁴ is hydrogen, R¹ is phenyl or substituted phenyl, R² is piperidinyl or substituted piperidinyl.

In certain specific embodiments, each of R³ and R⁴ is hydrogen, R¹ is phenyl (including phenyl substituted with one or more halo), and R² is heterocyclyl. In more specific embodiments, R² is a 1-piperidin-4-yl (including 1-piperidin-4-yl substituted at the 1-position with alkyl or acyl).

In various specific embodiments, the compound of Formula (IA1) is:
tert-butyl-4-(4-(6-amino-5-(5-phenyloxazol-2-yl)pyridin-3-yl)-1H-pyrazol-1-yl)piperidine-1-carboxylate;
3-(5-phenyloxazol-2-yl)-5-(1-(piperidin-4-yl)-1H-pyrazol-4-yl)pyridin-2-amine;
tert-butyl 4-(4-(6-amino-5-(5-(4-chlorophenyl)oxazol-2-yl)pyridin-3-yl)-1H-pyrazol-1-yl)piperidine-1-carboxylate;
3-(5-(4-chlorophenyl)oxazol-2-yl)-5-(1-(piperidin-4-yl)-1H-pyrazol-4-yl)pyridin-2-amine;
1-(4-(4-(6-amino-5-(5-(4-chlorophenyl)oxazol-2-yl)pyridin-3-yl)-1H-pyrazol-1-yl)piperidin-1-yl)ethanone;
(4-(4-(6-amino-5-(5-(4-chlorophenyl)oxazol-2-yl)pyridin-3-yl)-1H-pyrazol-1-yl)piperidin-1-yl)(cyclopropyl)methanone;
3-(5-(3-chlorophenyl)oxazol-2-yl)-5-(1-(piperidin-4-yl)-1H-pyrazol-4-yl)pyridin-2-amine;
1-(4-(4-(6-amino-5-(5-(3-chlorophenyl)oxazol-2-yl)pyridin-3-yl)-1H-pyrazol-1-yl)piperidin-1-yl)ethanone;
3-(5-(3-chlorophenyl)oxazol-2-yl)-5-(1-(1-methylpiperidin-4-yl)-1H-pyrazol-4-yl)pyridin-2-amine;
(4-(4-(6-amino-5-(5-(3-chlorophenyl)oxazol-2-yl)pyridin-3-yl)-1H-pyrazol-1-yl)piperidin-1-yl)(cyclopropyl)methanone;
(4-(4-(6-amino-5-(5-(3-chlorophenyl)oxazol-2-yl)pyridin-3-yl)-1H-pyrazol-1-yl)piperidin-1-yl)(phenyl)methanone;
1-(4-(4-(6-amino-5-(5-(3-chlorophenyl)oxazol-2-yl)pyridin-3-yl)-1H-pyrazol-1-yl)piperidin-1-yl)-2-phenylethanone;
(4-(4-(6-amino-5-(5-(4-chlorophenyl)oxazol-2-yl)pyridin-3-yl)-1H-pyrazol-1-yl)piperidin-1-yl)(phenyl)methanone;
1-(4-(4-(6-amino-5-(5-(4-chlorophenyl)oxazol-2-yl)pyridin-3-yl)-1H-pyrazol-1-yl)piperidin-1-yl)-2-phenylethanone;
3-(5-(4-chlorophenyl)oxazol-2-yl)-5-(1-(1-methylpiperidin-4-yl)-1H-pyrazol-4-yl)pyridin-2-amine;
1-(4-(4-(6-amino-5-(5-(3-chlorophenyl)oxazol-2-yl)pyridin-3-yl)-1H-pyrazol-1-yl)piperidin-1-yl)-2,2-dimethylpropan-1-one;
(4-(4-(6-amino-5-(5-(3-chlorophenyl)oxazol-2-yl)pyridin-3-yl)-1H-pyrazol-1-yl)piperidin-1-yl)(4-fluorophenyl)methanone; or
5-(1-(1-ethylpiperidin-4-yl)-1H-pyrazol-4-yl)-3-(5-phenyloxazol-2-yl)pyridin-2-amine.

In other more specific embodiments of Formula (IA1), each of R³ and R⁴ is hydrogen, R¹ is phenyl or substituted phenyl, R² is tetrahydropyranyl.

In various specific embodiments, the compound of Formula (IA1) is:
3-(5-phenyloxazol-2-yl)-5-(1-(tetrahydro-2pyran-4-yl)-1H-pyrazol-4-yl)pyridin-2-amine; or
3-(5-(4-chlorophenyl)oxazol-2-yl)-5-(1-(tetrahydro-2pyran-4-yl)-1H-pyrazol-4-yl)pyridin-2-amine.

In other more specific embodiments of Formula (IA1), each of R³ and R⁴ is hydrogen, R¹ is phenyl or substituted phenyl, R² is cyclohexyl.

In various specific embodiments, the compound of Formula (IA1) is:
3-(5-(3-chlorophenyl)oxazol-2-yl)-5-(1-cyclohexyl-1H-pyrazol-4-yl)pyridin-2-amine;
3-(5-(4-chlorophenyl)oxazol-2-yl)-5-(1-cyclohexyl-1H-pyrazol-4-yl)pyridin-2-amine; or
5-(1-cyclohexyl-1H-pyrazol-4-yl)-3-(5-phenyloxazol-2-yl)pyridin-2-amine.

In other embodiments, each of R³ and R⁴ is hydrogen, R¹ is heteroaryl (e.g., pyridinyl), and R² is heterocyclyl.

In more specific embodiments, the compound is 5-(1-(piperidin-4-yl)-1H-pyrazol-4-yl)-3-(5-(pyridin-3-yl)oxazol-2-yl)pyridin-2-amine.

Of the compounds of Formula (IA), another embodiment provides compounds of Formula (IA2):

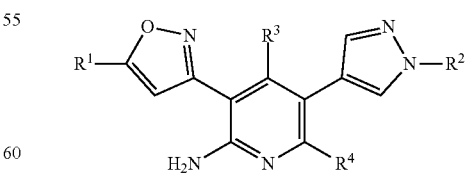

Formula (IA2)

wherein, R¹, R², R³, and R⁴ are as defined above.

In more specific embodiments of Formula (IA2), R¹ is aryl, heteroaryl, cycloalkyl or heterocyclyl. More specifically, R¹ is aryl. More specifically, R¹ is a phenyl or substituted phenyl.

In other embodiments of Formula (IA2), $R^2$ is aryl, heteroaryl, cycloalkyl or heterocyclyl. More specifically, $R^2$ is heterocyclyl. More specifically, $R^2$ is N-heterocyclyl.

In certain specific embodiments of Formula (IA2), each of $R^3$ and $R^4$ is hydrogen, $R^1$ is phenyl or substituted phenyl, $R^2$ is piperidinyl or substituted piperidinyl, tetrahydropyranyl or cyclohexyl.

In various specific embodiments, the compound of Formula (IA2) is:
5-(1-cyclohexyl-1H-pyrazol-4-yl)-3-(5-phenylisoxazol-3-yl)pyridin-2-amine;
3-(5-phenylisoxazol-3-yl)-5-(1-(tetrahydro-2H-pyran-4-yl)-1H-pyrazol-4-yl)pyridin-2-amine;
3-(5-phenylisoxazol-3-yl)-5-(1-(piperidin-4-yl)-1H-pyrazol-4-yl)pyridin-2-amine; or
5-(1-(1-methylpiperidin-4-yl)-1H-pyrazol-4-yl)-3-(5-phenylisoxazol-3-yl)pyridin-2-amine.

Of the compounds of Formula (IA), another embodiment provides compounds of Formula (IA3):

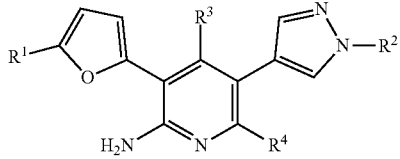

Formula (IA3)

wherein, $R^1$, $R^2$, $R^3$, and $R^4$ are as defined above.

In more specific embodiments of Formula (IA3), $R^1$ is aryl, heteroaryl, cycloalkyl or heterocyclyl. More specifically, $R^1$ is aryl. More specifically, $R^1$ is a phenyl or substituted phenyl.

In other embodiments of Formula (IA3), $R^2$ is aryl, heteroaryl, cycloalkyl or heterocyclyl. More specifically, $R^2$ is heterocyclyl. More specifically, $R^2$ is N-heterocyclyl.

In certain specific embodiments of Formula (IA3), each of $R^3$ and $R^4$ is hydrogen, $R^1$ is phenyl or substituted phenyl, $R^2$ is piperidinyl or substituted piperidinyl, tetrahydropyranyl or cyclohexyl.

In various specific embodiments, the compound of Formula (IA3) is:
3-(5-phenylfuran-2-yl)-5-(1-(piperidin-4-yl)-1H-pyrazol-4-yl)pyridin-2-amine;
5-(1-(1-methylpiperidin-4-yl)-1H-pyrazol-4-yl)-3-(5-phenylfuran-2-yl)pyridin-2-amine;
5-(1-cyclohexyl-1H-pyrazol-4-yl)-3-(5-phenylfuran-2-yl)pyridin-2-amine; or
3-(5-phenylfuran-2-yl)-5-(1-(tetrahydro-2H-pyran-4-yl)-1H-pyrazol-4-yl)pyridin-2-amine.

Of the compounds of Formula (IA), another embodiment provides compounds of Formula (IA4):

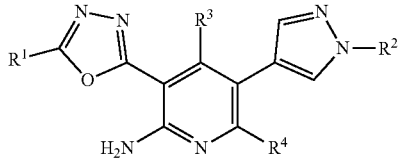

Formula (IA4)

wherein, $R^1$, $R^2$, $R^3$, and $R^4$ are as defined above.

In more specific embodiments of Formula (IA4), $R^1$ is aryl, heteroaryl, cycloalkyl, heterocyclyl, aralkyl, or cycloalkylalkyl.

In a more specific embodiment of Formula (IA4), $R^1$ is aryl. More specifically, $R^1$ is a phenyl or substituted phenyl.

In another more specific embodiment of Formula (IA4), $R^1$ is heteroaryl. More specifically, $R^1$ is a pyridinyl, substituted pyridinyl, pyrazinyl, substituted pyrazinyl, thiazolyl, substituted thiazolyl.

In further specific embodiment of Formula (IA4), $R^1$ is aralkyl. More specifically, $R^1$ is benzyl.

In further specific embodiment of Formula (IA4), $R^1$ is cycloalkylalkyl. More specifically, $R^1$ is cycloalkylalkyl.

In any of the above embodiments of Formula (IA4), $R^2$ is hydrogen, aryl, heteroaryl, cycloalkyl or heterocyclyl.

In a more specific embodiment of Formula (IA4), $R^2$ is heterocyclyl. More specifically, $R^2$ is N-heterocyclyl.

In more specific embodiments of Formula (IA4), $R^2$ is piperidinyl or substituted piperidinyl.

In other more specific embodiments of Formula (IA4), $R^2$ is tetrahydropyranyl.

In other more specific embodiments of Formula (IA4), $R^2$ is hydrogen.

In certain specific embodiments of Formula (IA4), each of $R^3$ and $R^4$ is hydrogen, $R^1$ is aryl, $R^2$ is heterocyclyl, including N-heterocyclyl.

In certain specific embodiments of Formula (IA4), each of $R^3$ and $R^4$ is hydrogen, $R^1$ is phenyl or phenyl substituted with one or more halo or alkyl, $R^2$ is piperidinyl or substituted piperidinyl.

In various specific embodiments, a compound of Formula (IA4) is:
tert-butyl 4-(4-(6-amino-5-(5-phenyl-1,3,4-oxadiazol-2-yl)pyridin-3-yl)-1H-pyrazol-1-yl)piperidine-1-carboxylate;
3-(5-phenyl-1,3,4-oxadiazol-2-yl)-5-(1-(piperidin-4-yl)-1H-pyrazol-4-yl)pyridin-2-amine;
3-(5-(2,6-dichloro-3-fluorophenyl)-1,3,4-oxadiazol-2-yl)-5-(1-(piperidin-4-yl)-1H-pyrazol-4-yl)pyridin-2-amine;
3-(5-(4-(tert-butyl)phenyl)-1,3,4-oxadiazol-2-yl)-5-(1-(piperidin-4-yl)-1H-pyrazol-4-yl)pyridin-2-amine;
tert-butyl 4-(4-(6-amino-5-(5-(4-(tert-butyl)phenyl)-1,3,4-oxadiazol-2-yl)pyridin-3-yl)-1H-pyrazol-1-yl)piperidine-1-carboxylate;
3-(5-(2,5-difluorophenyl)-1,3,4-oxadiazol-2-yl)-5-(1-(piperidin-4-yl)-1H-pyrazol-4-yl)pyridin-2-amine;
3-(5-(2,6-dichlorophenyl)-1,3,4-oxadiazol-2-yl)-5-(1-(piperidin-4-yl)-1H-pyrazol-4-yl)pyridin-2-amine;
tert-butyl 4-(4-(6-amino-5-(5-(2,6-dichlorophenyl)-1,3,4-oxadiazol-2-yl)pyridin-3-yl)-1H-pyrazol-1-yl)piperidine-1-carboxylate;
3-(5-(4-fluorophenyl)-1,3,4-oxadiazol-2-yl)-5-(1-(piperidin-4-yl)-1H-pyrazol-4-yl)pyridin-2-amine;
tert-butyl 4-(4-(6-amino-5-(5-(4-fluorophenyl)-1,3,4-oxadiazol-2-yl)pyridin-3-yl)-1H-pyrazol-1-yl)piperidine-1-carboxylate;
1-(4-(4-(6-amino-5-(5-(2,6-dichlorophenyl)-1,3,4-oxadiazol-2-yl)pyridin-3-yl)-1H-pyrazol-1-yl)piperidin-1-yl)ethanone;
3-(5-(2,6-dichlorophenyl)-1,3,4-oxadiazol-2-yl)-5-(1-(1-methylpiperidin-4-yl)-1H-pyrazol-4-yl)pyridin-2-amine;
1-(4-(4-(6-amino-5-(5-(2,6-dichlorophenyl)-1,3,4-oxadiazol-2-yl)pyridin-3-yl)-1H-pyrazol-1-yl)piperidin-1-yl)-4-methylpentan-1-one;
(4-(4-(6-amino-5-(5-(2,6-dichlorophenyl)-1,3,4-oxadiazol-2-yl)pyridin-3-yl)-1H-pyrazol-1-yl)piperidin-1-yl)(cyclopropyl)methanone;
(4-(4-(6-amino-5-(5-(2,6-dichlorophenyl)-1,3,4-oxadiazol-2-yl)pyridin-3-yl)-1H-pyrazol-1-yl)piperidin-1-yl)(phenyl)methanone;

1-(4-(4-(6-amino-5-(5-(2,6-dichlorophenyl)-1,3,4-oxadi-azol-2-yl)pyridin-3-yl)-1H-pyrazol-1-yl)piperidin-1-yl)-2-phenylethanone;

3-(5-(2,6-dichlorophenyl)-1,3,4-oxadiazol-2-yl)-5-(1-(1-ethylpiperidin-4-yl)-1H-pyrazol-4-yl)pyridin-2-amine; or 3-(5-(2,6-dichlorophenyl)-1,3,4-oxadiazol-2-yl)-5-(1-(1-dodecylpiperidin-4-yl)-1H-pyrazol-4-yl)pyridin-2-amine.

In other more specific embodiments of Formula (IA4), each of $R^3$ and $R^4$ is hydrogen, $R^1$ is heteroaryl or substituted heteroaryl, $R^2$ is piperidinyl or substituted piperidinyl.

In various specific embodiments, the compound of Formula (IA4) is:

tert-butyl 4-(4-(6-amino-5-(5-(pyrazin-2-yl)-1,3,4-oxadiazol-2-yl)pyridin-3-yl)-1H-pyrazol-1-yl)piperidine-1-carboxylate;

tert-butyl 4-(4-(6-amino-5-(5-(pyridin-2-yl)-1,3,4-oxadiazol-2-yl)pyridin-3-yl)-1H-pyrazol-1-yl)piperidine-1-carboxylate;

5-(1-(piperidin-4-yl)-1H-pyrazol-4-yl)-3-(5-(pyrazin-2-yl)-1,3,4-oxadiazol-2-yl)pyridin-2-amine;

5-(1-(piperidin-4-yl)-1H-pyrazol-4-yl)-3-(5-(pyridin-2-yl)-1,3,4-oxadiazol-2-yl)pyridin-2-amine;

tert-butyl 4-(4-(6-amino-5-(5-(thiazol-2-yl)-1,3,4-oxadiazol-2-yl)pyridin-3-yl)-1H-pyrazol-1-yl)piperidine-1-carboxylate;

5-(1-(piperidin-4-yl)-1H-pyrazol-4-yl)-3-(5-(thiazol-2-yl)-1,3,4-oxadiazol-2-yl)pyridin-2-amine;

5-(1-(piperidin-4-yl)-1H-pyrazol-4-yl)-3-(5-(pyridin-3-yl)-1,3,4-oxadiazol-2-yl)pyridin-2-amine;

tert-butyl 4-(4-(6-amino-5-(5-(pyridin-3-yl)-1,3,4-oxadiazol-2-yl)pyridin-3-yl)-1H-pyrazol-1-yl)piperidine-1-carboxylate;

tert-butyl 4-(4-(6-amino-5-(5-(4-(trifluoromethyl)-thiazol-2-yl)-1,3,4-oxadiazol-2-yl)pyridin-3-yl)-1H-pyrazol-1-yl)piperidine-1-carboxylate; or 5-(1-(piperidin-4-yl)-1H-pyrazol-4-yl)-3-(5-(4-(trifluoromethyl)thiazol-2-yl)-1,3,4-oxadiazol-2-yl)pyridin-2-amine.

In other more specific embodiments of Formula (IA4), each of $R^3$ and $R^4$ is hydrogen, $R^1$ is cycloalkylalkyl or aralkyl, $R^2$ is piperidinyl or substituted piperidinyl.

In various specific embodiments, the compound of Formula (IA4) is:

tert-butyl 4-(4-(6-amino-5-(5-(cyclopropylmethyl)-1,3,4-oxadiazol-2-yl)pyridin-3-yl)-1H-pyrazol-1-yl)piperidine-1-carboxylate;

3-(5-(cyclopropylmethyl)-1,3,4-oxadiazol-2-yl)-5-(1-(piperidin-4-yl)-1H-pyrazol-4-yl)pyridin-2-amine;

tert-butyl 4-(4-(6-amino-5-(5-benzyl-1,3,4-oxadiazol-2-yl)pyridin-3-yl)-1H-pyrazol-1-yl)piperidine-1-carboxylate; or 3-(5-benzyl-1,3,4-oxadiazol-2-yl)-5-(1-(piperidin-4-yl)-1H-pyrazol-4-yl)pyridin-2-amine.

In other more specific embodiments of Formula (IA4), each of $R^3$ and $R^4$ is hydrogen, $R^1$ is aryl or more specifically phenyl or substituted phenyl, $R^2$ is hydrogen.

In various specific embodiments, the compound of Formula (IA4) is:

3-(5-(2,6-dichlorophenyl)-1,3,4-oxadiazol-2-yl)-5-(1H-pyrazol-4-yl)pyridin-2-amine;

3-(5-phenyl-1,3,4-oxadiazol-2-yl)-5-(1H-pyrazol-4-yl)pyridin-2-amine;

3-(5-(4-(tert-butyl)phenyl)-1,3,4-oxadiazol-2-yl)-5-(1H-pyrazol-4-yl)pyridin-2-amine;

3-(5-(2,5-difluorophenyl)-1,3,4-oxadiazol-2-yl)-5-(1H-pyrazol-4-yl)pyridin-2-amine; or 3-(5-(4-fluorophenyl)-1,3,4-oxadiazol-2-yl)-5-(1H-pyrazol-4-yl)pyridin-2-amine.

In other more specific embodiments of Formula (IA4), each of $R^3$ and $R^4$ is hydrogen, $R^1$ is aryl or more specifically, phenyl or substituted phenyl, $R^2$ is cycloalkyl.

In a specific embodiment, the compound of Formula (IA4) is:

5-(1-cyclohexyl-1H-pyrazol-4-yl)-3-(5-(2,6-dichlorophenyl)-1,3,4-oxadiazol-2-yl)pyridin-2-amine;

5-(1-cyclohexyl-1H-pyrazol-4-yl)-3-(5-phenyl-1,3,4-oxadiazol-2-yl)pyridin-2-amine.

In yet other more specific embodiments of Formula (IA4), each of $R^3$ and $R^4$ is hydrogen, $R^1$ is aryl or more specifically, phenyl or substituted phenyl, $R^2$ is tetrahydropyranyl.

In a specific embodiment, the compound of Formula (IA4) is:

3-(5-(2,6-dichlorophenyl)-1,3,4-oxadiazol-2-yl)-5-(1-(tetrahydro-2H-pyran-4-yl)-1H-pyrazol-4-yl)pyridin-2-amine; or 3-(5-phenyl-1,3,4-oxadiazol-2-yl)-5-(1-(tetrahydro-2H-pyran-4-yl)-1H-pyrazol-4-yl)pyridin-2-amine.

Of the compounds of Formula (IA), another embodiment provides compounds of Formula (IA5):

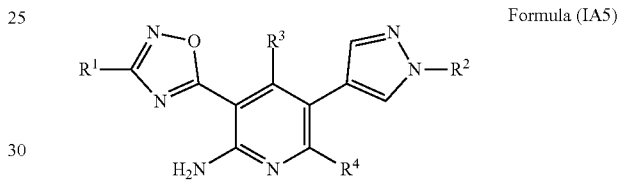

Formula (IA5)

In a more specific embodiment of Formula (IA5), $R^1$ is aryl. More specifically, $R^1$ is a phenyl or substituted phenyl.

In a more specific embodiment of Formula (IA5), $R^2$ is heterocyclyl. More specifically, $R^2$ is N-heterocyclyl.

In more specific embodiments of Formula (IA5), $R^2$ is piperidinyl, substituted piperidinyl, tetrahydropyranyl or cyclohexyl.

In other more specific embodiments of Formula (IA5), $R^2$ is hydrogen.

In certain specific embodiments of Formula (IA5), each of $R^3$ and $R^4$ is hydrogen, $R^1$ is aryl, $R^2$ is heterocyclyl, including N-heterocyclyl.

In yet other more specific embodiments of Formula (IA5), each of $R^3$ and $R^4$ is hydrogen, $R^1$ is aryl or more specifically, phenyl or substituted phenyl, $R^2$ is hydrogen, piperidinyl, substituted piperidinyl, tetrahydropyranyl or cyclohexyl.

In yet other more specific embodiments of Formula (IA5), each of $R^3$ and $R^4$ is hydrogen, $R^1$ is aryl or more specifically, phenyl or substituted phenyl, $R^2$ is piperidinyl, substituted piperidinyl.

In a specific embodiment, the compound of Formula (IA5) is:

3-(3-phenyl-1,2,4-oxadiazol-5-yl)-5-(1-(piperidin-4-yl)-1H-pyrazol-4-yl)pyridin-2-amine;

1-(4-(4-(6-amino-5-(3-phenyl-1,2,4-oxadiazol-5-yl)pyridin-3-yl)-1H-pyrazol-1-yl)piperidin-1-yl)ethanone;

(4-(4-(6-amino-5-(3-phenyl-1,2,4-oxadiazol-5-yl)pyridin-3-yl)-1H-pyrazol-1-yl)piperidin-1-yl)(cyclopropyl)methanone;

5-(1-(1-methylpiperidin-4-yl)-1H-pyrazol-4-yl)-3-(3-phenyl-1,2,4-oxadiazol-5-yl)pyridin-2-amine;

(4-(4-(6-amino-5-(3-phenyl-1,2,4-oxadiazol-5-yl)pyridin-3-yl)-1H-pyrazol-1-yl)piperidin-1-yl)(phenyl)methanone;

1-(4-(4-(6-amino-5-(3-phenyl-1,2,4-oxadiazol-5-yl)pyridin-3-yl)-1H-pyrazol-1-yl)piperidin-1-yl)-2-phenylethanone;

3-(3-(2,6-dichlorophenyl)-1,2,4-oxadiazol-5-yl)-5-(1-(piperidin-4-yl)-1H-pyrazol-4-yl)pyridin-2-amine;

3-(3-(2,6-dichlorophenyl)-1,2,4-oxadiazol-5-yl)-5-(1-(1-methylpiperidin-4-yl)-1H-pyrazol-4-yl)pyridin-2-amine;

3-(3-(2,6-dichlorophenyl)-1,2,4-oxadiazol-5-yl)-5-(1-(1-ethylpiperidin-4-yl)-1H-pyrazol-4-yl)pyridin-2-amine;

5-(1-(1-ethylpiperidin-4-yl)-1H-pyrazol-4-yl)-3-(3-phenyl-1,2,4-oxadiazol-5-yl)pyridin-2-amine; or 3-(3-(2,6-dichlorophenyl)-1,2,4-oxadiazol-5-yl)-5-(1-(1-dodecylpiperidin-4-yl)-1H-pyrazol-4-yl)pyridin-2-amine.

In yet other more specific embodiments of Formula (IA5), each of $R^3$ and $R^4$ is hydrogen, $R^1$ is aryl or more specifically, phenyl or substituted phenyl, $R^2$ is hydrogen, tetrahydropyranyl or cyclohexyl.

In a specific embodiment, the compound of Formula (IA5) is:

5-(1-cyclohexyl-1H-pyrazol-4-yl)-3-(3-phenyl-1,2,4-oxadiazol-5-yl)pyridin-2-amine;

5-(1-cyclohexyl-1H-pyrazol-4-yl)-3-(3-(2,6-dichlorophenyl)-1,2,4-oxadiazol-5-yl)pyridin-2-amine;

3-(3-phenyl-1,2,4-oxadiazol-5-yl)-5-(1-(tetrahydro-2H-pyran-4-yl)-1H-pyrazol-4-yl)pyridin-2-amine;

3-(3-(2,6-dichlorophenyl)-1,2,4-oxadiazol-5-yl)-5-(1-(tetrahydro-2H-pyran-4-yl)-1H-pyrazol-4-yl)pyridin-2-amine; or 3-(3-phenyl-1,2,4-oxadiazol-5-yl)-5-(1H-pyrazol-4-yl)pyridin-2-amine.

Of the compounds of Formula (IA), another embodiment provides compounds of Formula (IA6):

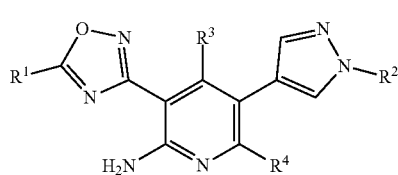

Formula (IA6)

wherein, $R^1$, $R^2$, $R^3$, and $R^4$ are as defined above.

In a more specific embodiment of Formula (IA6), $R^1$ is aryl. More specifically, $R^1$ is a phenyl or substituted phenyl.

In a more specific embodiment of Formula (IA6), $R^2$ is heterocyclyl. More specifically, $R^2$ is N-heterocyclyl.

In more specific embodiments of Formula (IA6), $R^2$ is piperidinyl or substituted piperidinyl, tetrahydropyranyl or cyclohexyl.

In other more specific embodiments of Formula (IA6), $R^2$ is hydrogen.

In certain specific embodiments of Formula (IA6), each of $R^3$ and $R^4$ is hydrogen, $R^1$ is aryl, $R^2$ is heterocyclyl, including N-heterocyclyl.

In yet other more specific embodiments of Formula (IA6), each of $R^3$ and $R^4$ is hydrogen, $R^1$ is aryl or more specifically, phenyl or substituted phenyl, $R^2$ is hydrogen, piperidinyl, substituted piperidinyl, tetrahydropyranyl or cyclohexyl.

In a specific embodiment, the compound of Formula (IA6) is:

5-(1-cyclohexyl-1H-pyrazol-4-yl)-3-(5-phenyl-1,2,4-oxadiazol-3-yl)pyridin-2-amine;

3-(5-phenyl-1,2,4-oxadiazol-3-yl)-5-(1-(tetrahydro-2H-pyran-4-yl)-1H-pyrazol-4-yl)pyridin-2-amine;

3-(5-phenyl-1,2,4-oxadiazol-3-yl)-5-(1-(piperidin-4-yl)-1H-pyrazol-4-yl)pyridin-2-amine;

5-(1-(1-methylpiperidin-4-yl)-1H-pyrazol-4-yl)-3-(5-phenyl-1,2,4-oxadiazol-3-yl)pyridin-2-amine;

3-(5-(2,5-dichlorophenyl)-1,2,4-oxadiazol-3-yl)-5-(1-(piperidin-4-yl)-1H-pyrazol-4-yl)pyridin-2-amine;

3-(5-phenyl-1,2,4-oxadiazol-3-yl)-5-(1H-pyrazol-4-yl)pyridin-2-amine.

Of the compounds of Formula (IA), another embodiment provides compounds of Formula (IA7):

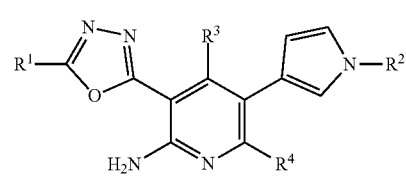

Formula (IA7)

wherein, $R^1$, $R^2$, $R^3$, and $R^4$ are as defined above. In a more specific embodiment of Formula (IA7), $R^1$ is aryl. More specifically, $R^1$ is a phenyl or substituted phenyl.

In a more specific embodiment of Formula (IA7), $R^2$ is heterocyclyl. More specifically, $R^2$ is piperidinyl or substituted piperidinyl.

In a specific embodiment, the compound of Formula (IA7) is:

3-(5-(2,6-dichlorophenyl)-1,3,4-oxadiazol-2-yl)-5-(1-(piperidin-4-yl)-1H-pyrrol-3-yl)pyridin-2-amine.

Of the compounds of Formula (I), an embodiment provides compound of Formula (IB):

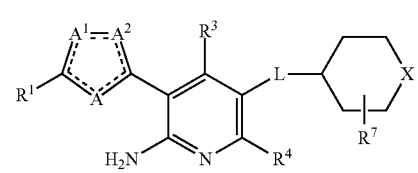

Formula (IB)

wherein,

A, $A^1$, $A^2$, $R^1$, $R^3$, $R^4$, and $R^5$ are as defined above,

L is heteroaryl or heterocycle;

$R^7$ is hydrogen, alkyl, alkoxy, or halo;

X is —O—, —$NR^8$—, or —$C(R^9)_2$—;

$R^8$ is hydrogen, alkyl, or —$C(O)R^{10}$—;

each $R^9$ is independently hydrogen, alkyl, alkoxy, or halo; and $R^{10}$ is alkyl, cycloalkyl, aryl, alkoxy, or aralkyl.

Of the compounds of Formula (IB), an embodiment provides compound of Formula (IB1):

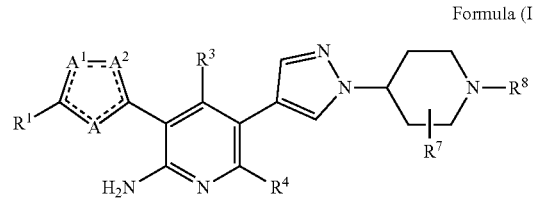

Formula (IB1)

wherein, each A, $A^1$ and $A^2$ is the same or different and independently —N=, —$CR^5$=, or —O—;

$R^1$ is aryl, heteroaryl, cycloalkyl, heterocyclyl, aralkyl, or cycloalkylalkyl;

each of $R^3$, $R^4$ and $R^7$ is hydrogen, $R^8$ is hydrogen, alkyl, or —C(O)$R^{10}$—; and $R^{10}$ is alkyl, cycloalkyl, aryl, alkoxy, or aralkyl.

In a more specific embodiment of Formula (IB1), $R^1$ is aryl. More specifically, $R^1$ is a phenyl or substituted phenyl.

In another more specific embodiment of Formula (IB1), $R^1$ is heteroaryl. More specifically, $R^1$ is a pyridinyl, substituted pyridinyl, pyrazinyl, substituted pyrazinyl, thiazolyl, substituted thiazolyl.

In further specific embodiment of Formula (IB1), $R^1$ is aralkyl. More specifically, $R^1$ is benzyl.

In further specific embodiment of Formula (IB1), $R^1$ is cycloalkylalkyl. More specifically, $R^1$ is cyclopropylalkyl.

Of the compounds of Formula (IB), an embodiment provides compound of Formula (IB2):

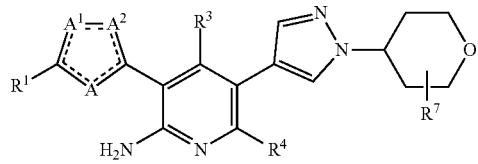

Formula (IB2)

wherein, each A, $A^1$ and $A^2$ is the same or different and independently —N=, —$CR^5$=, or —O—;

$R^1$ is aryl, heteroaryl, cycloalkyl, or heterocyclyl; and each of $R^3$, $R^4$ and $R^7$ is hydrogen.

In a more specific embodiment of Formula (IB2), $R^1$ is aryl. More specifically, $R^1$ is a phenyl or substituted phenyl.

Of the compounds of Formula (IB), an embodiment provides compound of Formula (IB3):

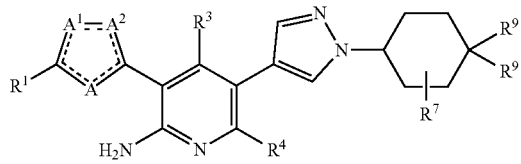

Formula (IB3)

wherein, each A, $A^1$ and $A^2$ is the same or different and independently —N=, —$CR^5$=, or —O—;

$R^1$ is aryl, heteroaryl, cycloalkyl, or heterocyclyl; and each of $R^3$, $R^4$, $R^7$ and $R^9$ is hydrogen;

In a more specific embodiment of Formula (IB3), $R^1$ is aryl. More specifically, $R^1$ is a phenyl or substituted phenyl.

Utility and Testing of the Compounds of the Disclosure

The present disclosure relates to compounds, pharmaceutical compositions and methods of using the compounds and pharmaceutical compositions for the treatment and/or prevention of diseases and conditions mediated by the kinase activity of Tyro3, Axl or Mer individually or by any combination of them, preferably diseases and conditions related to characterized by angiogenesis and/or cell proliferation and migration, and especially a disease and condition related to cancer, inflammatory diseases, autoimmune diseases, neurodisorders, and the like, by administering an effective amount of a compound of the disclosure.

The compounds of the disclosure modulate, preferably inhibit, the activity of human Tyro3, Axl or Mer individually or by any combination of them.

The general value of the compounds of the disclosure in modulating, especially inhibiting, the activity of Tyro3, Axl or Mer individually or by any combination of them can be determined using the assay described below in Example 21.

The compounds of the instant disclosure are inhibitors of Tyro3, Axl or Mer individually or inhibitors of any combination of them and are useful for treating diseases and disorders in humans and other organisms, including all those human diseases and disorders which are the result of abnormal kinase activity of Tyro3, Axl or Mer individually or any combination of them or which may be ameliorated by modulation of the kinase activity of Tyro3, Axl or Mer individually or any combination of them.

As defined herein, a disease or condition mediated by the abnormal kinase activity of Tyro3, Axl or Mer individually or any combination of them is defined as any disease or condition in which the activity of Tyro3, Axl or Mer individually or any combination of them is elevated and/or where inhibition of the activity of Tyro3, Axl or Mer individually or any combination of them can be demonstrated to bring about symptomatic improvements for the individual so treated. As defined herein, a disease or condition mediated by the abnormal activity of Tyro3, Axl or Mer individually or any combination of them includes, but is not limited to, a disease or condition which is, or is related to cancer, inflammatory diseases, autoimmune diseases, and neurodisorders. For purposes of this disclosure, Diseases and conditions which are alleviated by the modulation of the activity of Tyro3, Axl or Mer individually or any combination of them include, but are not limited to, solid tumors, including, but not limited to, breast, renal, endometrial, ovarian, thyroid, and non-small cell lung carcinoma, melanoma, prostate carcinoma, sarcoma, gastric cancer and uveal melanoma; liquid tumors, including but not limited to, leukemias particularly myeloid leukemias and lymphomas; endometriosis, vascular disease/injury including, but not limited to, restenosis, atherosclerosis and thrombosis, psoriasis; visual impairment due to macular degeneration; diabetic retinopathy and retinopathy of prematurity; kidney disease including, but not limited to, glomerulonephritis, diabetic nephropathy and renal transplant rejection, rheumatoid arthritis; osteoarthritis, osteoporosis and cataracts.

In addition to the foregoing, the compounds of the disclosure are useful in treating diseases and conditions which are affected by the following biological processes: Invasion, migration, metastasis, or drug resistance as manifested in cancer; stem cell biology as manifested in cancer; invasion, migration, adhesion, or angiogenesis as manifested in endometriosis; vascular remodeling as manifested in cardiovascular disease, hypertension or vascular injury; bone homeostatasis as manifested in osteoporosis or osteoarthritis; viral infection as manifested, for example, in ebola virus infection; or differentiation as manifested in obesity. The compounds of the disclosure may also be used to modulate inflammatory processes by treating sepsis, acting as vaccine adjuvants, and/or potentiating the immune response in immuno-compromised patients.

The following animal models provide guidance to one of ordinary skill in the art in testing the compounds of the disclosure for their use in treating the disease or condition indicated.

The compounds of the disclosure may be used or tested for their use in treating leukemias and lymphomas by, respectively, administering a pharmaceutically effective amount or testing the compounds in the xenograft in SCID mouse model using human cancer cell lines which express Tyro3 or Axl or Mer or co-expressing any combination of these three kinases including, but not limited to, A549, K562, HeLa, MDA-MB-231, SK—OV-3, OVCAR-8, DU145, H1299, ACHN, A498 and Caki-1.

The compounds of the disclosure may be tested for their use in treating leukemias in the xenograft in SCID or nu/nu mouse model using human AML and CML leukemia cell lines.

The compounds of the disclosure may be used or tested for their use in treating endometriosis by, respectively, administering a pharmaceutically effective amount to a subject in need thereof or using the syngenic mouse model of endometriosis (see Somigliana, E. et al., "Endometrial ability to implant in ectopic sites can be prevented by interleukin-12 in a murine model of endometriosis", Hum. Reprod. 1999, 14(12), 2944-2950). The compounds may also be tested for their use in treating endometriosis by using the rat model of endometriosis (see Lebovic, D. I. et al., "Peroxisome proliferator-activated receptor-gamma induces regression of endometrial explants in a rat model of endometriosis", Fertil. Steril., 2004, 82 Suppl 3, 1008-1013).

The compounds of the disclosure may be used or tested for their use in treating restenosis by, respectively, by administering a pharmaceutically effective amount to a subject in need thereof or using the balloon-injured rate carotid artery model (see Kim, D. W. et al., "Novel oral formulation of paclitaxel inhibits neointimal hyperplasia in a rat carotid artery injury model", Circulation, 2004, 109 (12), 1558-1563). The compounds of the disclosure may also be tested for their use in treating restenosis by using the percutaneous transluminal coronary angioplasty in apoE deficient mouse model (see von der Thusen, J. H. et al., "Adenoviral transfer of endothelial nitric oxide synthase attenuates lesion formation in a novel murine model of postangioplasty restenosis", Arterioscler. Thromb. Vasc. Biol., 2004, 24(2), 357-362).

The compounds of the disclosure may be used or tested for their use in treating atherosclerosis/thrombosis, respectively, by administering a pharmaceutically effective amount to a subject in need thereof or in the ApoE deficient mouse model (see Nakashima, Y. et al., "ApoE-deficient mice develop lesions of all phases of atherosclerosis throughout the arterial tree", Arterioscler. Thromb., 1994, 14(1), 133-140).

The compounds of the disclosure may also be used or tested for their use in treating thrombosis, respectively, by administering a pharmaceutically effective amount to a subject in need thereof or using the collagen-epinephrine-induced pulmonary thromboembolism model and the stasis induced venous thrombosis model (see Angelillo-Scherrer A. et al., "Role of Gas6 receptors in platelet signaling during thrombus stabilization and implications for antithrombotic therapy", J. Clin. Invest., 2005, 115, 237-246).

The compounds of the disclosure may be used or tested for their use in treating psoriasis by, respectively, by administering a pharmaceutically effective amount to a subject in need thereof or using the SCID mouse model or the human skin model of psoriasis (see Nickoloff, B. J. et al., "Severe combined immunodeficiency mouse and human psoriatic skin chimeras. Validation of a new animal model", Am. J. Pathol., 1995, 146(3), 580-588).

The compounds of the disclosure may be used or tested for their use in treating age-related macular degeneration or diabetic retinopathy by, respectively, administering a pharmaceutically effective amount to a subject in need thereof or using the rat corneal angiogenesis model (see Sarayba M A, Li L, Tungsiripat T, Liu N H, Sweet P M, Patel A J, Osann K E, Chittiboyina A, Benson S C, Pershadsingh H A, Chuck R S. Inhibition of corneal neovascularization by a peroxisome proliferator-activated receptor-gamma ligand. Exp. Eye. Res., 2005, 80(3), 435-442) or the laser-induced mouse choroidal neovasculation model (see Bora, P. S., et al., "Immunotherapy for choroidal neovascularization in a laser-induced mouse model simulating exudative (wet) macular degeneration", Proc. Natl. Acad. Sci. U.S.A, 2003, 100(5), 2679-2684).

The compounds of the disclosure may be used or tested for their use in treating retinopathy of prematurity, respectively, by administering a pharmaceutically effective amount to a subject in need thereof or in the mouse retinopathy of prematurity model (see Smith, L. E. et al., "Oxygen-induced retinopathy in the mouse", Invest. Ophthalmol. Vis. Sci., 1994, 35(1), 101-111). The compounds of the disclosure may be tested for their use in treating glomerulonephritis or diabetic nephropathy in the rat anti-Thyl.1-induced experimental mesengial proliferative glomerulonephritis model (see Smith, L. E. et al. cited above).

The compounds of the disclosure may be used or tested for their use in treating renal transplant rejection, respectively, by administering a pharmaceutically effective amount to a subject in need thereof or by using a rat model of chronic renal transplant rejection (see Yin, J. L. et al., "Expression of growth arrest-specific gene 6 and its receptors in a rat model of chronic renal transplant rejection", Transplantation, 2002, 73(4), 657-660).

The compounds of the disclosure may be used or tested for their use in treating rheumatoid arthritis by, respectively, administering a pharmaceutically effective amount to a subject in need thereof or using the CAIA mouse model (see Phadke, K. et al., "Evaluation of the effects of various anti-arthritic drugs on type II collagen-induced mouse arthritis model", Immunopharmacology, 1985, 10(1), 51-60).

The compounds of the disclosure may be used or tested for their use in treating osteoarthritis by, respectively, administering a pharmaceutically effective amount to a subject in need thereof or using the STR/ORT mouse model (see Brewster, M. et al., "Ro 32-3555, an orally active collagenase selective inhibitor, prevents structural damage in the STR/ORT mouse model of osteoarthritis", Arthritis. Rheum., 1998, 41(9), 1639-1644).

The compounds of the disclosure may be used or tested for their use in treating osteoporosis by, respectively, administering a pharmaceutically effective amount to a subject in need thereof or using the ovariectomized rat model (see Wronski, T J. et al., "Endocrine and pharmacological suppressors of bone turnover protect against osteopenia in ovariectomized rats", Endocrinology, 1989, 125(2), 810-816) or the ovariectomized mouse model (see Alexander, J. M. et al., "Human parathyroid hormone 1-34 reverses bone loss in ovariectomized mice", J Bone Miner Res., 2001, 16(9), 1665-1673; Fujioka, M. et al., "Equol, a metabolite of daidzein, inhibits bone loss in ovariectomized mice", J. Nut., 2004, 134(10), 2623-2627).

The compounds of the disclosure may be used or tested for their use in treating cataracts by, respectively, administering a pharmaceutically effective amount to a subject in need thereof or using the $H_2O_2$-induced model (see Kadoya, K. et al., "Role of calpain in hydrogen peroxide induced cataract", Curr. Eye Res., 1993, 12(4), 341-346) or the Emory mouse model (see Sheets, N. L. et al., "Cataract- and lens-specific up-regulation of ARK receptor tyrosine kinase in Emory mouse cataract", Invest. Ophthalmol. Vis. Sci., 2002, 43(6), 1870-1875).

Typically, a successful inhibitory therapeutic agent of the activity of Tyro3, Axl or Mer individually or any combination of them will meet some or all of the following criteria. Oral availability should be at or above 20% Animal model efficacy is less than about 20 mg/Kg, 2 mg/Kg, 1 mg/Kg, or 0.5 mg/Kg and the target human dose is between 10 and 250 mg/70 Kg, although doses outside of this range may be acceptable. ("mg/Kg" means milligrams of compound per kilogram of body mass of the subject to whom it is being administered). The required dosage should preferably be no more than about once or twice a day or at meal times. The therapeutic index (or ratio of toxic dose to therapeutic dose) should be greater than 10. The $IC_{50}$ ("Inhibitory Concentration-50%") is a measure of the amount of compound required to achieve 50% inhibition of the kinase activity, over a specific time period, in a kinase activity assay. Any process for measuring the kinase activity of Tyro3, Axl or Mer, preferably human Tyro3, Axl or Mer, may be utilized to assay the activity of the compounds useful in the methods of the disclosure in inhibiting said Tyro3, Axl or Mer activity. Compounds of the disclosure demonstrate an $IC_{50}$ in a 15 to 60 minute recombinant human kinase assay of preferably less than 10 mM, less than 5 µM, less than 2.5 µM, less than 1 µM. less than 750 nM, less than 500 nM, less than 250 nM, less than 100 nM, less than 50 nM, and most preferably less than 20 nM. Compounds of the disclosure may show reversible inhibition (i.e. competitive inhibition) or irreversible inhibition and preferably do not inhibit other protein kinases.

The identification of compounds of the disclosure as Tyro3, Axl or Mer inhibitors was readily accomplished using the recombinant human Tyro3, Axl and Mer proteins and employing the $^{33}$P-radiolabeled phosphate transfer assay for which the procedure is known to someone skilled in the art or as described in Example 18. When tested in this assay, compounds of the disclosure had greater than 50% inhibitory activity at 10 µM concentration of the test compound, preferably greater than 60% inhibitory activity at 10 µM concentration of the test compound, more preferably greater than 70% inhibitory activity at 10 µM concentration of the test compound, and even more preferably greater than 80% inhibitory activity at 10 µM concentration of the test compound, and the most preferably greater than 90% inhibitory activity at 10 µM concentration of the test compound, thereby demonstrating that the compounds of the disclosure are potent inhibitors of the kinase activity of Tyro3, Axl and Mer.

These results provide the basis for analysis of the structure-activity relationship (SAR) between test compounds and the kinase activity of Tyro3, Axl and Mer. Certain groups tend to provide more potent inhibitory compounds. SAR analysis is one of the tools those skilled in the art may employ to identify preferred embodiments of the compounds of the disclosure for use as therapeutic agents. Other methods of testing the compounds disclosed herein are also readily available to those skilled in the art. Thus, in addition, the determination of the ability of a compound to inhibit Tyro3, Axl and Mer activity may be accomplished in vivo. In one such embodiment this is accomplished by administering said chemical agent to an animal afflicted with a certain tumor graft model and subsequently detecting a change in tumor growth rate in said animal thereby identifying a therapeutic agent useful in treating the said tumors. In such embodiment, the animal may be a human, such as a human patient afflicted with such a disorder and in need of treatment of said disorder.

In specific embodiments of such in vivo processes, said change in Tyro3, Axl or Mer activity in said animal is a decrease in activity, preferably wherein said Tyro3, Axl or Mer inhibiting agent does not substantially inhibit the biological activity of other kinases.

The compounds of the disclosure can be used in combination with other therapeutic agents. Examples of alkylating agents that can be carried out in combination with include, but not limited to, fluorouracil (5-FU) alone or in further combination with leukovorin; other pyrimidine analogs such as UFT, capecitabine, gemcitabine and cytarabine, the alkyl sulfonates, e.g., busulfan (used in the treatment of chronic granulocytic leukemia), improsulfan and piposulfan; aziridines, e.g., benzodepa, carboquone, meturedepa and uredepa; ethyleneimines and methylmelamines, e.g., altretamine, triethylenemelamine, triethylenephosphoramide, triethylenethiophosphoramide and trimethylolmelamine; and the nitrogen mustards, e.g., chlorambucil (used in the treatment of chronic lymphocytic leukemia, primary macroglobulinemia and non-Hodgkin's lymphoma), cyclophosphamide (used in the treatment of Hodgkin's disease, multiple myeloma, neuroblastoma, breast cancer, ovarian cancer, lung cancer, Wilm's tumor and rhabdomyosarcoma), estramustine, ifosfamide, novembrichin, prednimustine and uracil mustard (used in the treatment of primary thrombocytosis, non-Hodgkin's lymphoma, Hodgkin's disease and ovarian cancer); and triazines, e.g., dacarbazine (used in the treatment of soft tissue sarcoma).

Examples of antimetabolite chemotherapeutic agents that can be carried out in combination with include, but not limited to, folic acid analogs, e.g., methotrexate (used in the treatment of acute lymphocytic leukemia, choriocarcinoma, mycosis fungiodes, breast cancer, head and neck cancer and osteogenic sarcoma) and pteropterin; and the purine analogs such as mercaptopurine and thioguanine which find use in the treatment of acute granulocytic, acute lymphocytic and chronic granulocytic leukemias. Examples of natural product-based chemotherapeutic agents that can be carried out in combination with include, but not limited to, the vinca alkaloids, e.g., vinblastine (used in the treatment of breast and testicular cancer), vincristine and vindesine; the epipodophyllotoxins, e.g., etoposide and teniposide, both of which are useful in the treatment of testicular cancer and Kaposi's sarcoma; the antibiotic chemotherapeutic agents, e.g., daunorubicin, doxorubicin, epirubicin, mitomycin (used to treat stomach, cervix, colon, breast, bladder and pancreatic cancer), dactinomycin, temozolomide, plicamycin, bleomycin (used in the treatment of skin, esophagus and genitourinary tract cancer); and the enzymatic chemotherapeutic agents such as L-asparaginase.

Examples of other signal transduction inhibiting agents that can be carried out in combination with include, but not limited to, gefitinib, erlotinib, sorafenib, herceptin, imatinib, dasatinib, sunitinib, nilotinib, lapatinib, pazopanib, vandetanib, vemurafenib, crizotinib, ruxolitinib, axitinib, bosutinib, regorafenib, tofacitinib, cabozantinib, ponatinib, dabrafenib, trametinib, and afatinib.

Other agents can be used in combination with the compound of the disclosure include, but not limited to, COX-II inhibitors, such as, but not limited to, Vioxx, Celebrex (celecoxib), valdecoxib, paracoxib, rofecoxib; matrix metalloproteinase inhibitors, such as, but not limited to, AG-3340, RO 32-3555, and RS 13-0830.

Pharmaceutical Compositions of the Disclosure and Administration

The present disclosure also relates to pharmaceutical composition containing the compounds of Formula (I), (IA), (IB) or substructures thereof disclosed herein. In one embodiment, the present disclosure relates to a composition comprising compounds of Formula (I), (IA), (IB) or substructures thereof in a pharmaceutically acceptable carrier and in an amount effective to modulate the activity of Tyro3, Axl and Mer individually or in any combination of them or to treat diseases related to angiogenesis and/or cell proliferation and migration, and especially cancer, inflammatory diseases, autoimmune diseases, neurodisorders and the like when administered to an animal, preferably a mammal, most preferably a human patient. In an embodiment of such composition, the patient has hyperproliferative disease, and especially cancer, inflammatory diseases, autoimmune diseases, neurodisorders and the like, before administration of said compound of the disclosure and the compound of the disclosure is present in an amount effective to reduce said lipid level.

The pharmaceutical compositions useful herein also contain a pharmaceutically acceptable carrier, including any suitable diluent or excipient, which includes any pharmaceutical agent that does not itself induce the production of antibodies harmful to the individual receiving the composition, and which may be administered without undue toxicity. Pharmaceutically acceptable carriers include, but are not limited to, liquids, such as water, saline, glycerol and ethanol, and the like. A thorough discussion of pharmaceutically acceptable carriers, diluents, and other excipients is presented in REMINGTON'S PHARMACEUTICAL SCIENCES (Mack Pub. Co., N.J. current edition).

Those skilled in the art are also familiar with determining administration methods (oral, intravenous, inhalation, subcutaneous, etc.), dosage forms, suitable pharmaceutical excipients and other matters relevant to the delivery of the compounds to a subject in need thereof.

In an alternative use of the disclosure, the compounds of the disclosure can be used in in vitro or in vivo studies as exemplary agents for comparative purposes to find other compounds also useful in treatment of, or protection from, the various diseases disclosed herein.

Administration of the compounds of the disclosure, or their pharmaceutically acceptable salts, in pure form or in an appropriate pharmaceutical composition, can be carried out via any of the accepted modes of administration of agents for serving similar utilities. The pharmaceutical compositions of the disclosure can be prepared by combining a compound of the disclosure with an appropriate pharmaceutically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. Typical routes of administering such pharmaceutical compositions include, without limitation, oral, topical, transdermal, inhalation, parenteral, sublingual, buccal, rectal, vaginal, and intranasal. The term parenteral as used herein includes subcutaneous injections, intravenous, intramuscular, intrasternal injection or infusion techniques. Pharmaceutical compositions of the disclosure are formulated so as to allow the active ingredients contained therein to be bioavailable upon administration of the composition to a patient. Compositions that will be administered to a subject or patient take the form of one or more dosage units, where for example, a tablet may be a single dosage unit, and a container of a compound of the disclosure in aerosol form may hold a plurality of dosage units. Actual methods of preparing such dosage forms are known, or will be apparent, to those skilled in this art; for example, see Remington: The Science and Practice of Pharmacy, 20th Edition (Philadelphia College of Pharmacy and Science, 2000). The composition to be administered will, in any event, contain a therapeutically effective amount of a compound of the disclosure, or a pharmaceutically acceptable salt thereof, for treatment of a disease or condition of interest in accordance with the teachings of this disclosure.

A pharmaceutical composition of the disclosure may be in the form of a solid or liquid. In one aspect, the carrier(s) are particulate, so that the compositions are, for example, in tablet or powder form. The carrier(s) may be liquid, with the compositions being, for example, an oral oil, injectable liquid or an aerosol, which is useful in, for example, inhalatory administration.

When intended for oral administration, the pharmaceutical composition is preferably in either solid or liquid form, where semi-solid, semi-liquid, suspension and gel forms are included within the forms considered herein as either solid or liquid.

As a solid composition for oral administration, the pharmaceutical composition may be formulated into a powder, granule, compressed tablet, pill, capsule, chewing gum, wafer or the like form. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent.

When the pharmaceutical composition is in the form of a capsule, for example, a gelatin capsule, it may contain, in addition to materials of the above type, a liquid carrier such as polyethylene glycol or oil.

The pharmaceutical composition may be in the form of a liquid, for example, an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions of the disclosure, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile. A liquid pharmaceutical composition of the disclosure intended for either parenteral or oral administration should contain an amount of a compound of the disclosure such that a suitable dosage will be obtained. Typically, this amount is at least 0.01% of a compound of the disclosure in the composition. When intended for oral administration, this amount may be varied to be between 0.1 and about 70% of the weight of the composition. Preferred oral pharmaceutical compositions contain between about 4% and about 75% of the compound of the disclosure. Preferred pharmaceutical compositions and preparations according to the present disclosure are prepared so that a parenteral dosage unit contains between 0.01 to 10% by weight of the compound prior to dilution of the disclosure.

The pharmaceutical composition of the disclosure may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. Topical formulations may contain a concentration of the compound of the disclosure from about 0.1 to about 10% w/v (weight per unit volume). The pharmaceutical composition of the disclosure may be intended for rectal administration, in the form, for example, of a suppository, which will melt in the rectum and release the drug. The composition for rectal administration may contain an oleaginous base as a suitable nonirritating excipient. Such bases include, without limitation, lanolin, cocoa butter and polyethylene glycol. The pharmaceutical composition of the disclosure may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule.

The pharmaceutical composition of the disclosure in solid or liquid form may include an agent that binds to the compound of the disclosure and thereby assists in the delivery of the compound. Suitable agents that may act in this capacity include a monoclonal or polyclonal antibody, a protein or a liposome. The pharmaceutical composition of the disclosure may consist of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols of compounds of the disclosure may be delivered in single phase, bi-phasic, or tri-phasic systems in order to deliver the active ingredient(s). Delivery of the aerosol includes the necessary container, activators, valves, subcontainers, and the like, which together may form a kit. One of ordinary skill in the art, without undue experimentation may determine preferred aerosols. The pharmaceutical compositions of the disclosure may be prepared by methodology well known in the pharmaceutical art. For example, a pharmaceutical composition intended to be administered by injection can be prepared by combining a compound of the disclosure with sterile, distilled water so as to form a solution. A surfactant may be added to facilitate the formation of a homogeneous solution or suspension. Surfactants are compounds that non-covalently interact with the compound of the disclosure so as to facilitate dissolution or homogeneous suspension of the compound in the aqueous delivery system.

The compounds of the disclosure, or their pharmaceutically acceptable salts, are administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy. Generally, a therapeutically effective daily dose is (for a 70 kg mammal) from about 0.001 mg/kg (i.e., 0.7 mg) to about 100 mg/kg (i.e., 7.0 gm); preferably a therapeutically effective dose is (for a 70 kg mammal) from about 0.01 mg/kg (i.e., 7 mg) to about 50 mg/kg (i.e., 3.5 g); more preferably a therapeutically effective dose is (for a 70 kg mammal) from about 1 mg/kg (i.e., 70 mg) to about 25 mg/kg (i.e., 1.75 g).

Compounds of Formula (I), (IA), (IB) or substructures thereof, or pharmaceutically acceptable derivatives thereof, may also be administered simultaneously with, prior to, or after administration of one or more other therapeutic agents. Such combination therapy includes administration of a single pharmaceutical dosage formulation which contains a compound of the disclosure and one or more additional active agents, as well as administration of the compound of the disclosure and each active agent in its own separate pharmaceutical dosage formulation. For example, a compound of the disclosure and the other active agent can be administered to the patient together in a single oral dosage composition such as a tablet or capsule, or each agent administered in separate oral dosage formulations. Where separate dosage formulations are used, the compounds of the disclosure and one or more additional active agents can be administered at essentially the same time, i.e., concurrently, or at separately staggered times, i.e., sequentially; combination therapy is understood to include all these regimens.

Isotopic Enrichment of Compounds

Isotopic enrichment is a process by which the relative abundance of the isotopes of a given element are altered, thus producing a form of the element that has been enriched in one particular isotope and depleted in its other isotopic forms. Isotopic enrichment of a drug are used for the following applications: reducing or eliminating unwanted metabolites; increasing the half-life of the parent drug; decreasing the number of doses needed to achieve a desired effect; decreasing the amount of a dose necessary to achieve a desired effect; increasing the formation of active metabolites, if any are formed; and/or decreasing the production of deleterious metabolites in specific tissues and/or create a more effective drug and/or a safer drug for combination therapy, whether the combination therapy is intentional or not.

Replacement of an atom for one of its isotopes often will result in a change in the reaction rate of a chemical reaction. This phenomenon is known as the Kinetic Isotope Effect. For example, if a C—H bond is broken during a rate-determining step in a chemical reaction (i.e. the step with the highest transition state energy), substitution of a deuterium for that hydrogen will cause a decrease in the reaction rate and the process will slow down. This phenomenon is known as the Deuterium Kinetic Isotope Effect (Foster et. al., *Adv.*

Drug Res., 1985, 14, 1-36; Kushner et. al., Can. J. Physiol. Pharmacol., 1999, 77, 79-88).

Improvement of metabolism, pharmacokinetics, pharmacodynamics, and toxicity profiles of pharmaceuticals by isotopic enrichment such as deuteration has been demonstrated by the following examples: Lijinsky et. al., J. Nat. Cancer Inst., 1982, 69, 1127-1133; Gately et. al., J. Nucl. Med., 1986, 27, 388-394; Gordon et. al., Drug Metab. Dispos., 1987, 15, 589-594; Mangold et. al., Mutation Res., 1994, 308, 33-42; Zello et. al., Metabolism, 1994, 43, 487-491; Wade D., Chem. Biol. Interact., 1999, 117, 191-637.

Preparation of the Compounds of Formula (I), (IA) or (TB)

It is understood that in the following description, combinations of substituents and/or variables of the depicted formulae are permissible only if such contributions result in stable compounds.

It will also be appreciated by those skilled in the art that in the process described below the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (e.g., t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R" (where R" is alkyl, aryl or arylalkyl), p-methoxybenzyl, trityl and the like. Suitable protecting groups for carboxylic acid include alkyl, aryl or arylalkyl esters.

Protecting groups may be added or removed in accordance with standard techniques, which are well-known to those skilled in the art and as described herein.

The use of protecting groups is described in detail in Green, T. W. and P. G. M. Wutz, Protective Groups in Organic Synthesis (1999), 3rd Ed., Wiley. The protecting group may also be a polymer resin such as a Wang resin or a 2-chlorotrityl-chloride resin.

It will also be appreciated by those skilled in the art, although such protected derivatives of compounds of this disclosure may not possess pharmacological activity as such, they may be administered to a mammal and thereafter metabolized in the body to form compounds of the disclosure which are pharmacologically active. Such derivatives may therefore be described as "prodrugs". All prodrugs of compounds of this disclosure are included within the scope of the disclosure.

The following Reaction Schemes illustrate methods to make compounds of this disclosure. It is understood that one of those skilled in the art would be able to make these compounds by similar methods or by methods known to one skilled in the art. In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, e.g., Advanced Organic Chemistry: Reactions, Mechanisms, and Structure, 5th edition (Wiley, December 2000)) or prepared as described in this disclosure.

As representative examples, compounds of formula (IA1), in which W is

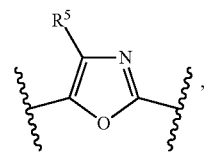

(i.e., A is —O—, $A^1$ is —C($R^5$)=; $A^2$ is —N=) and $R^5$ is hydrogen can be synthesized following the general procedure as described in Reaction Scheme 1.

REACTION SCHEME 1

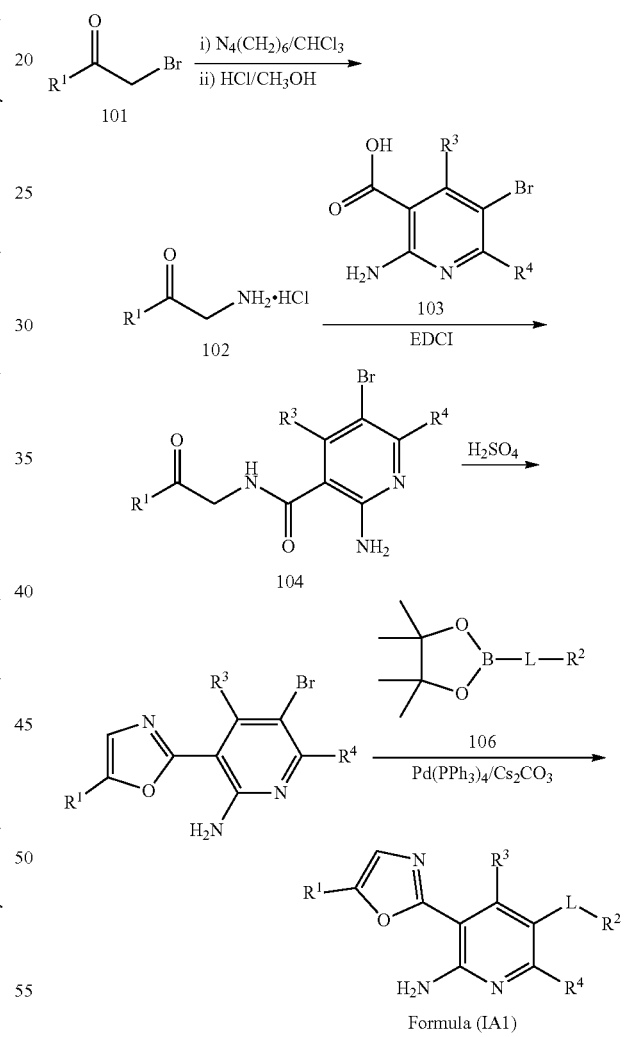

The starting materials for the above reaction scheme are commercially available or can be prepared according to methods known to one skilled in the art or by methods disclosed herein. In general, the compounds of the Formula (I) or (IA1) are prepared in the above reaction scheme as follows:

The starting α-bromo ketone 101 is treated with hexamethylenetetramine under Delépine reaction conditions to afford the α-amino ketone 102 as a hydrochloride salt.

Under amide formation conditions, 2-amino-5-bromonicotinic acid 103 reacts with compound 102 in the presence of a coupling reagent, such as, but not limited to, EDCI to form compound 104. The oxazole compound 105 is obtained under acid cyclization conditions. This oxazole compound is coupled with the boron reagent 106 under the Suzuki coupling reaction conditions to afford the compound of formula (IA1) where W is

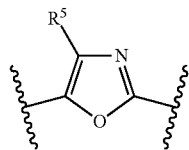

and $R^5$ is hydrogen.

Compounds of formula (IA2), in which W is

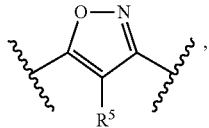

(i.e., A is —C($R^5$)=; $A^1$ is —O—, $A^2$ is —N=) and $R^5$ is hydrogen can be synthesized following the general procedure as described in Reaction Scheme 2.

REACTION SCHEME 2

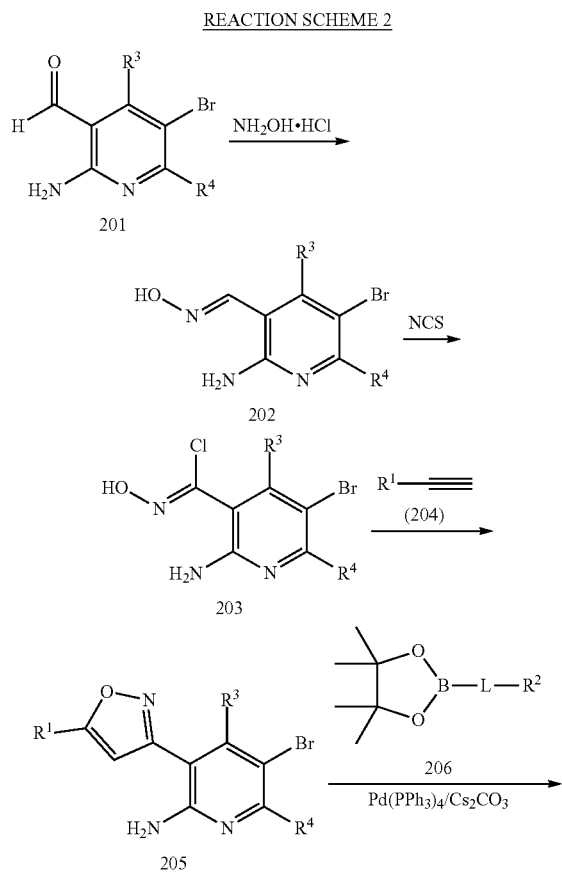

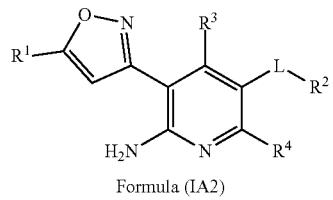

Formula (IA2)

The starting materials for the above reaction scheme are commercially available or can be prepared according to methods known to one skilled in the art or by methods disclosed herein. In general, the compounds of the Formula (IA2) are prepared in the above reaction scheme as follows:

The starting material, an appropriately substituted 2-amino-5-bromonicotinic aldehyde 201 reacts with hydroxylamine hydrochloride salt under reflux to afford the nicotinic aldoxime intermediate 202. This oxime compound is then treated with N-chlorosuccinimide to generate the chlorinated oxime compound 203 which is cyclized with acetylene compound 204 to afford the isoxazole compound 205. This isoxazole compound is coupled with the boron reagent 206 under the Suzuki coupling reaction conditions to afford the compound of formula (IA2).

Alternatively, compounds of formula (IA3), in which W is

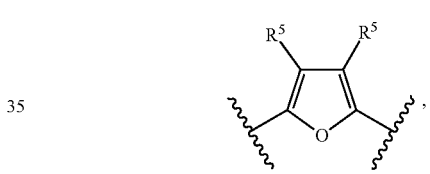

(i.e., A is —O—, each of $A^1$ and $A^2$ is —C($R^5$)=) and each $R^5$ is hydrogen, can be synthesized following the general procedure as described in Reaction Scheme 3.

REACTION SCHEME 3

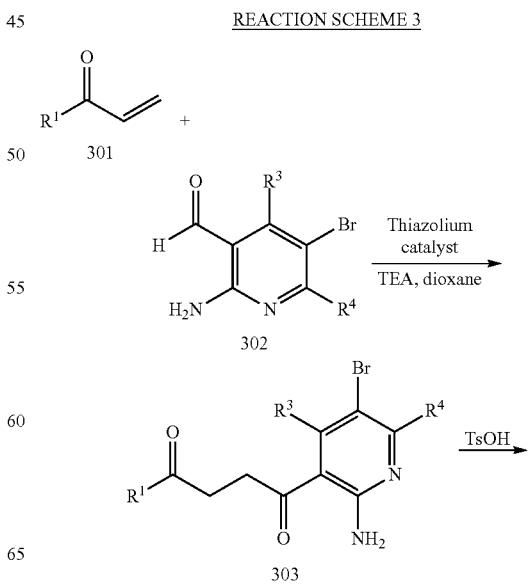

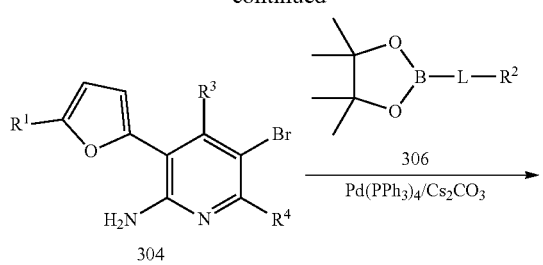

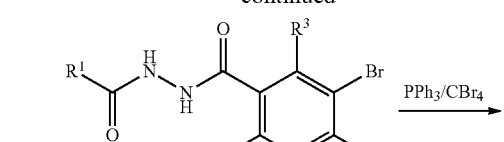

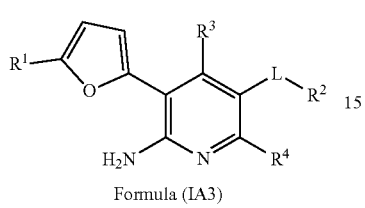

The starting materials for the above reaction scheme are commercially available or can be prepared according to methods known to one skilled in the art or by methods disclosed herein. In general, the compounds of the Formula (IA3) are prepared in the above reaction scheme as follows:

The starting α-ketoalkene 301 reacts with aldehyde compound 302 (e.g., an appropriately substituted 2-amino-5-bromonicotinic aldehyde) under the Stetter Reaction conditions in the presence of a thiazolium catalyst, such as, but not limited to, 3-benzyl-5-(2-hydroxyethyl)-4-methylthiazolium chloride, to afford 1,4-dione compound 303, which is cyclized under the Paal-Knorr furan synthesis conditions to afford the furan compound 304. This furan compound is further coupled with the boron reagent 306 under the Suzuki coupling reaction conditions to afford the compound of formula (IA3).

In general, compounds of formula (IA4), in which W is

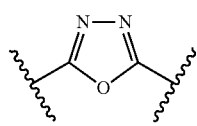 [SMILES: *c1nnc(*)o1]

(i.e., A is —O—, each $A^1$ and $A^2$ is —N=) can be synthesized following the general procedure as described in Reaction Scheme 4.

REACTION SCHEME 4

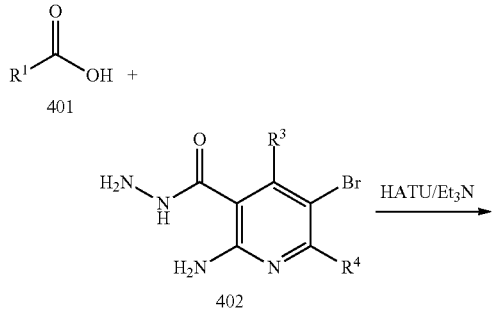

The starting materials for the above reaction scheme are commercially available or can be prepared according to methods known to one skilled in the art or by methods disclosed herein. In general, the compounds of the disclosure are prepared in the above reaction scheme as follows:

The starting carboxylic acid 401 reacts with hydrazide 402 in the presence of a coupling reagent, such as, but not limited to, HATU and a base, such as, but not limited to, triethylamine to generate the 1,2-diacylhydrazine compound 403. Cyclodehydration of compound 403 in the presence of a dehydrating reagent, such as, but not limited to, triphenylphosphine/carbon tetrabromide to generate the 1,3,4-oxadiazole 404. This oxadiazole compound is coupled with the boron reagent 406 under the Suzuki coupling reaction conditions to afford the compound of Formula (IA4).

Compounds of formula (IA5) of this disclosure in which W is

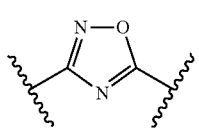 [SMILES: *c1noc(*)n1]

(i.e., A is —N=, $A^1$ is —N=, $A^2$ is —O—) can be synthesized following the general procedure as described in Reaction Scheme 5.

REACTION SCHEME 5

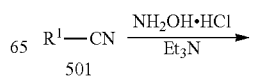

REACTION SCHEME 6

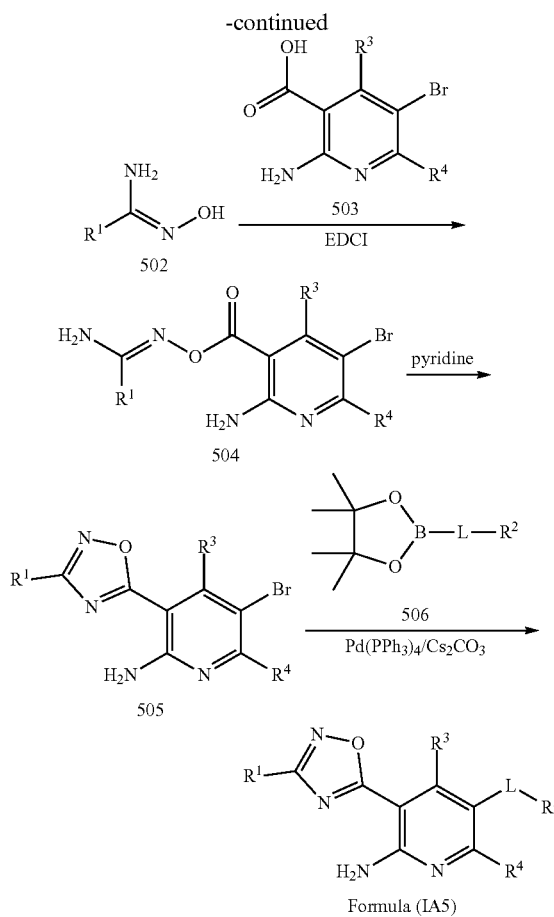

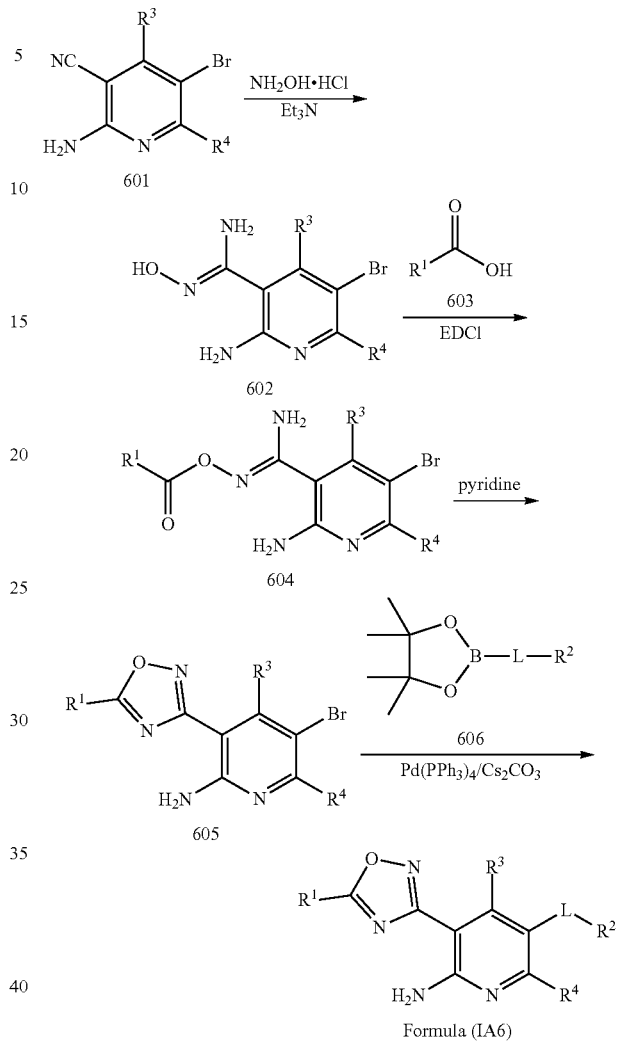

The starting materials for the above reaction scheme are commercially available or can be prepared according to methods known to one skilled in the art or by methods disclosed herein. In general, the compounds of the disclosure are prepared in the above reaction scheme as follows:

Nitrile compound 501 is treated with hydroxylamine hydrochloride in the presence of a base, such as, but not limited to, triethylamine under reflux to generate amidoxime compound 502. A condensation reaction of the amidoxime compound 602 with an appropriately substituted nicotinic acid 503 in the presence of a coupling agent, such as, but not limited to, EDCI generates compound 504. Under reflux in the presence of pyridine, compound 504 is cyclized to afford 1,2,4-oxadiazole compound 505. This oxadiazole compound is coupled with a boron reagent 506 under the Suzuki coupling reaction conditions to afford the compound of formula (IA5).

Compounds of Formula (IA6) of this disclosure in which W is

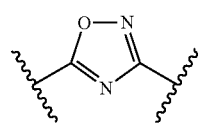 [SMILES: *c1noc(*)n1]

(i.e., A is —N═, $A^1$ is —O—, $A^2$ is —N═) can be synthesized following the general procedure as described in Reaction Scheme 6.

The starting materials for the above reaction scheme are commercially available or can be prepared according to methods known to one skilled in the art or by methods disclosed herein. In general, the compounds of the disclosure are prepared in the above reaction scheme as follows:

Nitrile compound 601 is treated with hydroxylamine hydrochloride in the presence of a base, such as, but not limited to, triethylamine under reflux to generate amidoxime compound 602. The condensation of amidoxime 602 with carboxlic acid 303 in the presence of a coupling agent, such as, but not limited to, EDCI generates compound 604. Under reflux in the presence of pyridine, compound 604 is cyclized to afford 1,2,4-oxadiazole compound 605. This oxadiazole compound is coupled with the boron reagent 606 under the Suzuki coupling reaction conditions to afford the compound of formula (I) of the disclosure.

More specific details on synthetic techniques for compounds of Formula (I), (IA) and (IB) and their substructures are provided herein. Unless otherwise provided, all reagents and reaction conditions employed in synthesis are known to those skilled in the art and are available from ordinary commercial sources.

PREPARATIONS

Preparation 1

Preparation of 2-amino-1-phenylethanone Hydrochloride

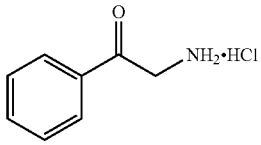

To a solution of 2-bromo-1-phenylethanone (5.00 g, 25.0 mmol) in 25 mL of chloroform was added a solution of hexamethylenetetramine (3.50 g, 25.0 mmol) in 15 mL of chloroform dropwise. The resulting mixture was stirred at ambient temperature for 1 hour to yield a white solid. The white solid collected by filtration was dissolved in 50 mL of methanol and 10.0 mL of concentrated hydrochloroic acid was added. The mixture was refluxed for 3 hours to afford white precipitates. The precipitates were collected by filtration and washed with tetrahydrofuran to afford 2-amino-1-phenylethanone hydrochloride as a white solid in 66% yield (2.80 g) which was used directly for the next step reaction without further purification. $^1$H NMR (400 MHz, DMSO-$d_6$): δ 8.49 (br s, 3H), 8.00-7.96 (m, 2H), 7.72-7.66 (m, 1H), 7.56-7.50 (m, 2H), 4.54 (s, 2H).

Preparation 1.1

Preparation of 2-amino-1-(4-chlorophenyl)ethanone Hydrochloride

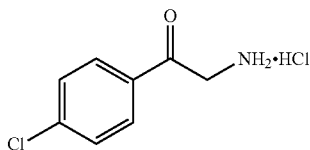

Following the procedure as described in Preparation 1, making variations using 2-bromo-1-(4-chlorophenyl)ethanone to replace 2-bromo-1-phenylethanone, 2-amino-1-(4-chlorophenyl)ethanone hydrochloride was obtained as a white solid in a quantitative yield. $^1$H NMR (400 MHz, DMSO-$d_6$): δ 8.52 (br s, 3H), 8.02-7.97 (m, 2H), 7.65-7.60 (m, 2H), 4.53 (s, 2H).

Preparation 1.2

Preparation of 2-amino-1-(3-chlorophenyl)ethanone Hydrochloride

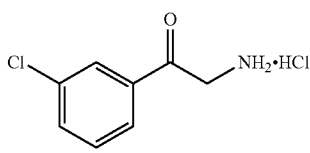

Following the procedure as described in Preparation 1, making variations using 2-bromo-1-(3-chlorophenyl)ethanone to replace 2-bromo-1-phenylethanone, 2-amino-1-(3-chlorophenyl)ethanone hydrochloride was obtained as a white solid in 96% yield. $^1$H NMR (400 MHz, DMSO-$d_6$): δ 8.54 (br s, 3H), 8.02-7.98 (m, 1H), 7.96-7.92 (m, 1H), 7.78-7.74 (m, 1H), 7.62-7.56 (m, 1H), 4.57 (s, 2H).

Preparation 2

Preparation of 2-amino-5-bromo-N-(2-oxo-2-phenylethyl)nicotinamide

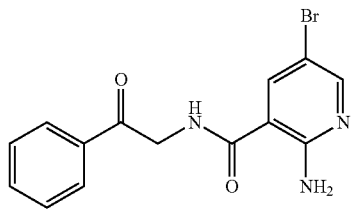 [SMILES: Nc1ncc(Br)cc1C(=O)NCC(=O)c1ccccc1]

To a suspension of 2-amino-5-bromopyridine-3-carboxylic acid (0.43 g, 2.00 mmol) and 2-amino-1-phenylethanone hydrochloride (0.51 g, 3.00 mmol) in 40 mL of dichloromethane was added 1-ethyl-3-(3-dimethylaminopropyl)-carbodiimide (1.19 g, 6.00 mmol). The mixture was stirred at ambient temperature for 3 hours. After removal of the solvent in vacuo, the residue was purified by column chromatography eluted with 1:1 ethyl acetate:hexane to afford 2-amino-5-bromo-N-(2-oxo-2-phenylethyl)nicotinamide as a yellow solid in 72% yield (0.48 g). $^1$H NMR (400 MHz, CDCl$_3$): δ 8.21 (d, J=2.0 Hz, 1H), 8.13-8.02 (m, 2H), 8.03 (d, J=2.0 Hz, 1H), 7.70-7.65 (m, 1H), 7.58-7.52 (m, 2H), 7.24 (t, J=4.4 Hz, 1H), 6.57 (br s, 2H), 4.91 (d, J=4.4 Hz, 2H).

Preparation 2.1

Preparation of 2-amino-5-bromo-N-(2-(4-chlorophenyl)-2-oxoethyl)nicotinamide

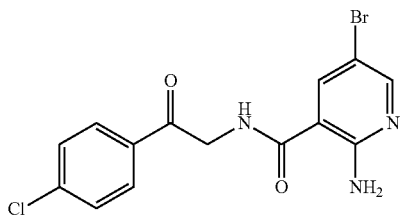 [SMILES: Nc1ncc(Br)cc1C(=O)NCC(=O)c1ccc(Cl)cc1]

Following the procedure as described in Preparation 2, making variations using 2-amino-1-(4-chlorophenyl)ethanone hydrochloride to replace 2-amino-1-phenyl-ethanone hydrochloride, 2-amino-5-bromo-N-(2-(4-chlorophenyl)-2-oxoethyl)-nicotinamide was obtained as a yellow solid in 55% yield. $^1$H NMR (400 MHz, CDCl$_3$): δ 8.12 (s, 1H), 8.11 (s, 1H), 7.90 (d, J=6.8 Hz, 2H), 7.80 (d, J=4.8 Hz, 1H), 7.44 (d, J=6.8 Hz, 2H), 6.58 (br s, 2H), 4.77 (d, J=4.8 Hz, 2H).

Preparation 3

Preparation of 5-bromo-3-(5-phenyloxazol-2-yl)pyridin-2-amine

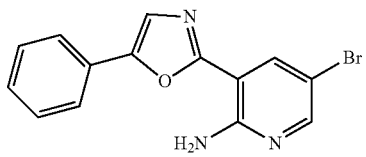 [SMILES: Nc1ncc(Br)cc1-c1ncc(-c2ccccc2)o1]

A mixture of 2-amino-5-bromo-N-(2-oxo-2-phenylethyl) nicotinamide (450 mg, 1.35 mmol) in 10 mL of concentrated sulfuric acid was stirred at ambient temperature for 18 hours. The mixture was mixed with 20 mL of ice cold water and neutralized with aqueous ammonia to yield yellow precipitates. After suction filtration, the yellow precipitates were washed with water to afford 5-bromo-3-(5-phenyloxazol-2-yl)pyridin-2-amine as a yellowish solid in 88% yield (375 mg). $^1$H NMR (400 MHz, CD$_3$OD): δ 8.28 (s, 1H), 8.18 (s, 1H), 7.74-7.70 (m, 2H), 7.54-7.34 (m, 4H), 6.85 (br s, 2H).

Preparation 3.1

Preparation of 5-bromo-3-(5-(4-chlorophenyl)oxazol-2-yl)pyridin-2-amine

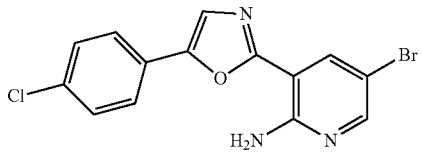 [SMILES: Nc1ncc(Br)cc1-c1ncc(-c2ccc(Cl)cc2)o1]

Following the procedure as described in Preparation 3, making variations using 2-amino-5-bromo-N-(2-(4-chlorophenyl)-2-oxoethyl)nicotinamide to replace 2-amino-5-bromo-N-(2-oxo-2-phenylethyl)nicotinamide, 5-bromo-3-(5-(4-chlorophenyl)-oxazol-2-yl)pyridin-2-amine was obtained as a yellow solid in 86%. $^1$H NMR (400 MHz, CDCl$_3$): δ 8.24 (s, 1H), 8.19 (s, 1H), 7.65 (d, J=8.0 Hz, 2H), 7.50-7.38 (m, 3H), 6.75 (br s, 2H).

Preparation 4

Preparation of 5-bromo-3-(5-(3-chlorophenyl)oxazol-2-yl)pyridin-2-amine

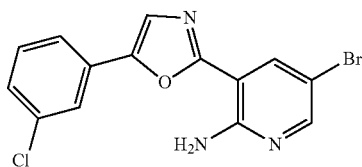 [SMILES: Nc1ncc(Br)cc1-c1ncc(-c2cccc(Cl)c2)o1]

To a suspension of 2-amino-5-bromopyridine-3-carboxylic acid (1.75 g, 8.09 mmol) and 2-amino-1-(3-chlorophenyl)ethanone hydrochloride (2.50 g, 12.1 mmol) in 100 mL of dichloromethane was added 1-ethyl-3-(3-dimethylaminopropyl)carbodiimide (3.19 g, 16.2 mmol). The mixture was stirred at ambient temperature overnight to yield yellow precipitates. After filtration, the yellow precipitates were washed with dichloromethane to afford a yellow solid which was mixed with 10 mL of concentrated sulfuric acid and was stirred at ambient temperature for 20 hours. The reaction mixture was mixed with 40 mL of ice cold water and neutralized with ammonia solution to yield yellow precipitates. After suction filtration, the yellow precipitates were washed with water to afford 5-bromo-3-(5-(3-chlorophenyl)oxazol-2-yl)pyridin-2-amine as an orange solid in 77% (2.00 g). $^1$H NMR (400 MHz, CDCl$_3$): δ 8.27 (d, J=2.4 Hz, 1H), 8.19 (d, J=2.4 Hz, 1H), 7.71 (s, 1H), 7.65-7.57 (m, 1H), 7.55-7.45 (m, 1H), 7.45-7.33 (m, 2H), 6.78 (br s, 2H).

Preparation 5

Preparation of 5-bromo-3-(5-phenylisoxazol-3-yl)pyridin-2-amine

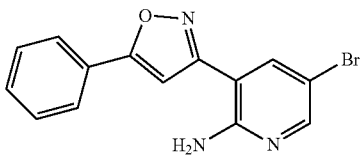

A. To a solution of 2-aminopyridine-3-carbaldehyde (10.1 g, 81.0 mmol) in acetonitrile (150 mL) was added N-bromosuccinimide (15.1 g, 84.0 mmol). The resulting mixture was stirred at reflux for 2 hours. After cooled to room temperature, the reaction mixture was filtered. The collected solid was washed with methanol, and dried in vacuo to afford 2-amino-5-bromopyridine-3-carbaldehyde as a brown solid in 79% yield (12.9 g). $^1$H NMR (400 MHz, CDCl$_3$): δ 9.81 (s, 1H), 8.30 (d, J=2.4 Hz, 1H), 7.89 (d, J=2.4 Hz, 1H), 6.78 (br s, 2H).

B. A mixture of 2-amino-5-bromopyridine-3-carbaldehyde (8.90 g, 44.3 mmol), hydroxylamine hydrochloride (3.72 g, 53.1 mmol) and sodium acetate (4.36 g, 53.1 mmol) in 95% ethanol (150 mL) was stirred under reflux for 3 hours. After cooled to room temperature, the reaction mixture was concentrated and the residue was re-dissolved in ethyl acetate (500 mL), washed with brine (2×300 mL). The aqueous phase was back-washed with ethyl acetate (2×250 mL). The combined organic layer was washed with brine (2×250 mL), dried and filtered. The solvent of the filtrate was removed in vacuo, and the residue was dried in vacuo to afford 2-amino-5-bromopyridine-3-carbaldehyde oxime as a yellow solid in 90% yield (8.60 g). $^1$H NMR (400 MHz, CDCl$_3$): δ 11.4 (s, 1H), 8.19 (s, 1H), 7.98 (d, J=2.4 Hz, 1H), 7.77 (d, J=2.4 Hz, 1H), 7.10 (br s, 2H).

C. To a suspension of 2-amino-5-bromopyridine-3-carbaldehyde oxime (4.32 g, 20.0 mmol) was added N-chlorosuccinimide (2.99 g, 22.0 mmol). The mixture was stirred at 50° C. overnight and then cooled to room temperature, and followed by the addition of dichloromethane (100 mL), phenylacetylene (2.24 mL, 20.0 mmol) and triethylamine (4.20 mL, 30.0 mmol). The resulting mixture was stirred at room temperature overnight, then diluted with ethyl acetate (500 mL), washed with brine (4×300 mL). The aqueous phase was back-washed with ethyl acetate (1×300 mL). The combined organic layer was washed with brine (3×150 mL), dried and filtered. The solvent of the filtrate was removed in vacuo and the residue was purified by column chromatography eluted with hexanes:ethyl acetate (from 10:1 to 5:1) to afford 5-bromo-3-(5-phenylisoxazol-3-yl)pyridin-2-amine as a yellow solid in 6% yield (366 mg). $^1$H NMR (400 MHz, CDCl$_3$): δ 8.19 (d, J=2.4 Hz, 1H), 7.89 (d, J=2.4 Hz, 1H), 7.87-7.82 (m, 2H), 7.55-7.48 (m, 3H), 6.87 (s, 1H), 6.40-6.25 (br s, 2H).

Preparation 6

Preparation of 5-bromo-3-(5-phenylfuran-2-yl)pyridin-2-amine

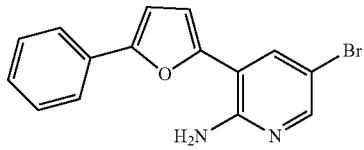 [SMILES: Nc1ncc(Br)cc1-c1ccc(-c2ccccc2)o1]

A. A mixture of 3-chloro-1-phenylpropan-1-one (2.00 g, 11.9 mmol) and triethylamine (1.44 g, 14.2 mmol) in chloroform was stirred at room temperature overnight. The reaction mixture was diluted with dichloromethane, washed with 0.1 M hydrochloric acid solution (2×20 mL) and brine (20 mL). The organic solution was dried over anhydrous sodium sulfate and filtered. The filtrate was dried in vacuo to afford 1-phenylprop-2-en-1-one as a yellow liquid in 91% yield (1.42 g). $^1$H NMR (400 MHz, CDCl$_3$): δ 7.97-7.92 (m, 2H), 7.61-7.54 (m, 1H), 7.51-7.44 (m, 2H), 7.16 (dd, J=17.2, 10.8 Hz, 1H), 6.44 (dd, J=17.2, 1.6 Hz, 1H), 5.93 (dd, J=10.8, 1.6 Hz, 1H).

B. A mixture of 1-phenylprop-2-en-1-one (1.40 g, 10.6 mmol), 2-amino-5-bromopyridine-3-carbaldehyde (1.70 g, 8.48 mmol) and triethylamine in 5 mL of dioxane was heated at 100° C. for 10 minutes, followed by the addition of 3-benzyl-5-(2-hydroxyethyl)-4-methylthiazolium chloride (0.49 g, 1.59 mmol) in 20 mL of dioxane dropwise in 0.5 hour. The resulting mixture was heated at 100° C. overnight, then concentrated. The residue was purified by column chromatography eluted with 10% ethyl acetate in hexane to afford 1-(2-amino-5-bromopyridin-3-yl)-4-phenylbutane-1,4-dione as a yellow solid in 13% yield (300 mg). $^1$H NMR (400 MHz, CDCl$_3$): δ 8.25 (d, J=2.4 Hz, 1H), 8.21 (d, J=2.4 Hz, 1H), 8.08-8.02 (m, 2H), 7.62-7.56 (m, 1H), 7.52-7.46 (m, 2H), 3.47-3.36 (m, 4H).

C. A mixture of 1-(2-amino-5-bromopyridin-3-yl)-4-phenylbutane-1,4-dione (300 mg, 0.900 mmol) and p-toluenesulfonic acid (0.860 g, 4.50 mmol) in 10 mL of toluene was heated at 100° C. for 2 hours, then concentrated. The residue was neutralized with saturated sodium bicarbonate, then extracted with dichloromethane (3×20 mL). The organic solution was dried over anhydrous sodium sulfate and filtered. The solvent of the filtrate was removed in vacuo and the residue was purified by column chromatography eluted with 20% ethyl acetate in hexane to afford 5-bromo-3-(5-phenylfuran-2-yl)pyridin-2-amine as a yellow solid in 48% yield (136 mg). $^1$H NMR (400 MHz, CDCl$_3$): δ 8.08 (d, J=2.4 Hz, 1H), 7.89 (d, J=2.4 Hz, 1H), 7.73-7.68 (m, 2H), 7.47-7.41 (m, 2H), 7.35-7.28 (m, 1H), 6.80 (d, J=3.6 Hz, 1H), 6.76 (d, J=3.6 Hz, 1H), 5.23 (br s, 2H).

Preparation 7

Preparation of 5-bromo-3-(5-(pyridin-3-yl)oxazol-2-yl)pyridin-2-amine

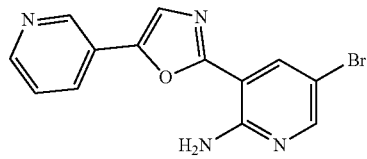 [SMILES: Nc1ncc(Br)cc1-c1ncc(-c2cccnc2)o1]

A. To a solution of 1-(pyridin-3-yl)ethanone (10.0 g, 82.4 mmol) in 100 mL of acetic acid was added 48% (w/v) hydrobromic acid in acetic acid (21.8 mL, 123.6 mmol), followed by the addition of bromine dropwise. The resulting mixture was heated at 60° C. for 2 hours to yield white precipitates. After filtration, the solid was washed with ether to afford a white solid which was mixed with 200 mL of acetonitrile and sodium diformylamide (16.9 g, 178 mmol) was added. The mixture was heated at 60° C. for 3 hours. After removal of solvent, the residue was purified by column chromatography to afford N-formyl-N-(2-oxo-2-(pyridin-3-yl)ethyl)formamide as a yellowish wax in 23% yield (1.6 g). $^1$H NMR (400 MHz, CDCl$_3$): δ 9.23 (m, 1H), 9.05 (s, 2H), 8.89-8.83 (m, 1H), 8.27-8.22 (m, 1H), 7.52-7.45 (m, 1H), 5.10 (s, 2H).

B. To a solution of N-formyl-N-(2-oxo-2-(pyridin-3-yl)ethyl)formamide (1.60 g, 8.33 mmol) in 150 mL of ethanol was added 10.0 mL of concentrated hydrochloric acid. The mixture was heated at 50° C. overnight to yield white precipitates which were collected by filtration and washed with ice cold ethanol to afford 2-amino-1-(pyridin-3-yl)ethanone hydrochloride as a white solid in 81% yield (1.17 g). $^1$H NMR (400 MHz, DMSO-d$_6$): δ 9.25-9.22 (m, 1H), 8.93-8.90 (m, 1H), 8.62-8.53 (br s, 3H), 8.63-8.49 (m, 1H), 7.78-7.75 (m, 1H), 4.65-4.58 (m, 2H).

C. To a suspension of 2-amino-5-bromopyridine-3-carboxylic acid (0.566 g, 2.60 mmol) and 2-amino-1-(pyridin-3-yl)ethanone hydrochloride (0.500 g, 2.90 mmol) in 40 mL of dichloromethane was added HATU (1.97 g, 5.20 mmol), followed by the addition of N,N-diisopropylethylamine (1.00 mL, 5.80 mmol). The mixture was stirred at room temperature overnight to yield white precipitates. After filtration, the white precipitates were washed with water to afford 2-amino-5-bromo-N-(2-oxo-2-(pyridin-3-yl)ethyl)pyridine-3-carboxamide as a white solid in 69% yield (0.60 g). $^1$H NMR (400 MHz, DMSO-d$_6$): δ 9.17-9.14 (m, 1H), 9.00 (t, J=5.6 Hz, 1H), 8.82-8.78 (m, 1H), 8.35-8.28 (m, 1H), 8.18-8.13 (m, 2H), 7.60-7.53 (m, 1H), 7.21 (br s, 2H), 4.74 (d, J=5.6 Hz, 2H).

D. To a cold (0° C.) suspension of 2-amino-5-bromo-N-(2-oxo-2-(pyridin-3-yl)ethyl)pyridine-3-carboxamide (0.56 g, 1.67 mmol) in 25 mL of dichloromethane was added triethylamine (1.14 mL, 8.35 mmol), followed by the addition of triphenylphosphine (0.55 g, 2.09 mmol) and tetrabromomethane (0.69 g, 2.09 mmol). The resulting mixture was stirred at room temperature for 5 hours. After removal of solvent, the residue was purified by column chromatography eluted with 3:2 ethyl acetate:dichloromethane to afford a yellow solid which was further purified by recrystallization in methanol to afford 5-bromo-3-(5-(pyridin-3-yl)oxazol-2-yl)pyridin-2-amine as a light yellow solid in 35% yield (0.185 g). $^1$H NMR (400 MHz, CDCl$_3$): δ 9.02-8.98 (m, 1H), 8.64-8.60 (m, 1H), 8.27 (d, J=2.4 Hz, 1H), 8.21 (d, J=2.4 Hz, 1H), 8.04-7.99 (m, 1H), 7.56 (s, 1H), 7.44-7.40 (m, 1H), 6.75 (br s, 2H).

Preparation 8

Preparation of 2-amino-5-bromonicotinohydrazide

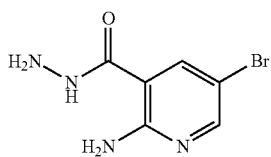

1. To a suspension of 2-aminonicotinic acid 1 (13.8 g, 100 mmol) in 100 mL of acetic acid was added bromine (5.70 mL, 110 mmol) dropwise over 20 min. The mixture was stirred at ambient temperature for 1 h, evaporated, triturated with ether (50 mL). The solid was collected by filtration, washed with diethyl ether (2×20 mL) and dried in air. The product, 2-amino-5-bromonicotinic acid hydrobromide, was obtained as a brown solid in 93% yield (27.8 g). $^1$H NMR (400 MHz, DMSO-d$_6$): δ 8.28 (d, J=2.4 Hz, 1H), 8.15 (d, J=2.4 Hz, 1H), 5.00 (br s, 4H).

2. To a suspension of 2-amino-5-bromonicotinic acid hydrobromide (18.8 g, 60.0 mmol) in 150 mL of methanol was added conc. sulfuric acid (6 mL). The mixture was heated at 75° C. for 2 days, evaporated, diluted with water (100 mL), basified with solid sodium bicarbonate to pH 7-8, and extracted with ethyl acetate (3×100 mL). The extracts were washed with brine (50 mL), dried over sodium sulfate and filtered. The filtrate was dried in vacuo and the residue was purified by flash chromatography eluted with ethyl acetate/hexanes (1/4) to afford methyl 2-amino-5-bromonicotinate as a white solid in 36% yield (5.0 g). $^1$H NMR (400 MHz, CDCl$_3$): δ 8.26 (d, J=2.8 Hz, 1H), 8.23 (d, J=2.8 Hz, 1H), 3.92 (s, 3H).

3. To a solution of methyl 2-amino-5-bromonicotinate (4.95 g, 21.4 mmol) in tetrahydrofuran/methanol (30 mL/30 mL) was added 5.2 mL of hydrazine hydrate (NH$_2$NH.H$_2$O). The mixture was stirred at 75° C. for 18 h, and cooled. The solid was collected by filtration, washed with methanol (2×10 mL) and dried in air to afford 2-amino-5-bromonicotinohydrazide as a white solid (3.6 g). The filtrate was evaporated and purified by column chromatography eluted with 5% methanol in dichloromethane to afford another 1.1 g of 2-amino-5-bromonicotinohydrazide as a white solid (total 4.7 g, 95%). $^1$H NMR (400 MHz, DMSO-d$_6$): δ 9.74 (s, 1H), 8.09 (d, J=2.4 Hz, 1H), 7.95 (d, J=2.4 Hz, 1H), 7.13 (s, 2H), 4.42 (s, 2H).

Preparation 9

Preparation of 2-amino-5-bromo-N'-(2,6-dichloro-3-fluorobenzoyl)nicotinohydrazide

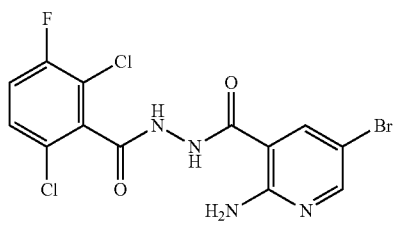 [SMILES: Nc1ncc(Br)cc1C(=O)NNC(=O)c1c(Cl)ccc(F)c1Cl]

To a cooled (0° C.) solution of 2-amino-5-bromonicotinohydrazide (0.71 g, 3.08 mmol) in 18 mL of pyridine was added a solution of 2,6-dichloro-3-fluorobenzoyl chloride (crude, 3.24 mmol, prepared from 2,6-dichloro-3-fluorobenzoic acid (0.68 g, 3.24 mmol) with oxalyl chloride) in dichloromethane (5 mL) dropwise. The mixture was warmed to ambient temperature overnight and evaporated. The residue was purified by flash chromatography eluted with 3% methanol in dichloromethane to afford 2-amino-5-bromo-N'-(2,6-dichloro-3-fluorobenzoyl)nicotino-hydrazide as a white solid in 26% yield (0.34 g). $^1$H NMR (400 MHz, DMSO-d$_6$): δ 10.8 (s, 1H), 10.7 (s, 1H), 8.24-8.18 (m, 2H), 7.62-7.52 (m, 2H), 7.24 (br s, 2H).

Preparation 9.1

Preparation of 2-amino-N'-benzoyl-5-bromonicotinohydrazide

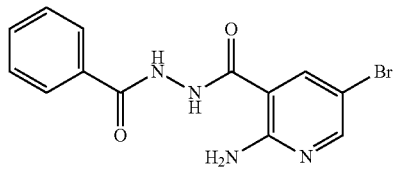 [SMILES: Nc1ncc(Br)cc1C(=O)NNC(=O)c1ccccc1]

Following the procedure as described in Preparation 9, making variations using benzoyl chloride to replace 2,6-dichloro-3-fluorobenzoyl chloride to react with 2-amino-5-bromonicotinohydrazide, 2-amino-N'-benzoyl-5-bromonicotinohydrazide was obtained as a white solid in 72% yield. $^1$H NMR (400 MHz, DMSO-d$_6$): δ 10.5 (s, 2H), 8.20-8.15 (m, 2H), 7.89-7.85 (m, 2H), 7.59-7.46 (m, 3H), 7.22 (br s, 2H).

Preparation 9.2

Preparation of Synthesis of 2-amino-5-bromo-N'-(4-(tert-butyl)benzoyl)nicotinohydrazide

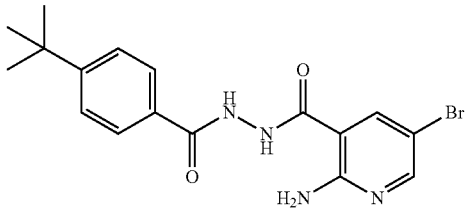 [SMILES: CC(C)(C)c1ccc(C(=O)NNC(=O)c2cc(Br)cnc2N)cc1]

Following the procedure as described in Preparation 9, making variations using 4-tert-butylbenzoyl chloride to replace 2,6-dichloro-3-fluorobenzoyl chloride to react with 2-amino-5-bromonicotinohydrazide, 2-amino-5-bromo-N'-(4-(tert-butyl)benzoyl)-nicotinohydrazide was obtained as a white solid in a quantitative yield. $^1$H NMR (400 MHz, DMSO-d$_6$): δ 10.5 (s, 1H), 10.4 (s, 1H), 8.20-8.15 (m, 2H), 7.84-7.78 (m, 2H), 7.52-7.46 (m, 2H), 7.22 (br s, 2H), 1.23 (s, 9H).

Preparation 9.3

Preparation of 2-amino-5-bromo-N'-(2,5-difluorobenzoyl)nicotinohydrazide

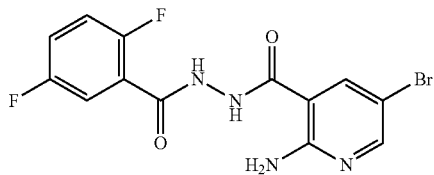

Following the procedure as described in Preparation 9, making variations using 2,5-difluorobenzoyl chloride to replace 2,6-dichloro-3-fluorobenzoyl chloride to react with 2-amino-5-bromonicotinohydrazide, 2-amino-5-bromo-N'-(2,5-difluorobenzoyl)-nicotinohydrazide was obtained as a white solid in 94% yield. $^1$H NMR (400 MHz, DMSO-d$_6$): δ 10.6 (s, 1H), 10.4 (s, 1H), 8.19 (d, J=2.4 Hz, 1H), 8.15 (d, J=2.4 Hz, 1H), 7.48-7.34 (m, 3H), 7.23 (br s, 2H).

Preparation 9.4

Preparation of 2-amino-5-bromo-N'-(2,6-dichlorobenzoyl)nicotinohydrazide

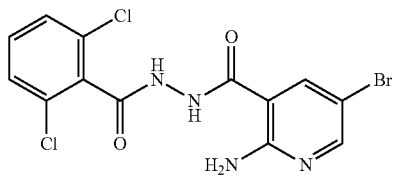 [SMILES: Nc1ncc(Br)cc1C(=O)NNC(=O)c1c(Cl)cccc1Cl]

Following the procedure as described in Preparation 9, making variations using 2,6-dichlorobenzoyl chloride to replace 2,6-dichloro-3-fluorobenzoyl chloride to react with 2-amino-5-bromonicotinohydrazide, 2-amino-5-bromo-N'-(2,6-dichlorobenzoyl)nicotinohydrazide was obtained as a white solid in 97% yield. $^1$H NMR (400 MHz, DMSO-d$_6$): δ 10.7 (s, 1H), 10.6 (s, 1H), 8.25-8.17 (m, 2H), 7.55-7.43 (m, 3H), 7.23 (br s, 2H).

Preparation 9.5

Preparation of 2-amino-5-bromo-N'-(4-fluorobenzoyl)nicotinohydrazide

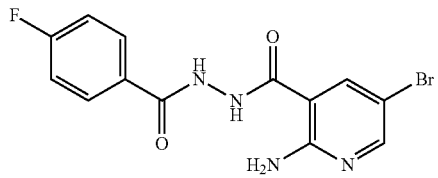

Following the procedure as described in Preparation 9, making variations using 4-fluorobenzoyl chloride to replace 2,6-dichloro-3-fluorobenzoyl chloride to react with 2-amino-5-bromonicotinohydrazide, 2-amino-5-bromo-N'-(4-fluorobenzoyl)nicotinehydrazide was obtained as a white solid in 71% yield. $^1$H NMR (400 MHz, DMSO-d$_6$): δ 10.5 (s, 2H), 8.19 (d, J=2.4 Hz, 1H), 8.15 (d, J=2.4 Hz, 1H), 7.98-7.82 (m, 2H), 7.36-7.28 (m, 2H), 7.21 (br s, 2H).

Preparation 9.6

Preparation of 2-amino-5-bromo-N'-(cyclohexanecarbonyl)nicotinohydrazide

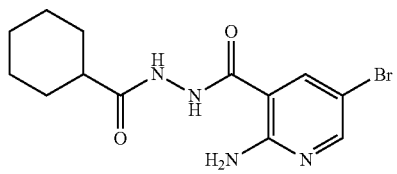 [SMILES: Nc1ncc(Br)cc1C(=O)NNC(=O)C1CCCCC1]

Following the procedure as described in Preparation 9, making variations using cyclohexanecarbonyl chloride to replace 2,6-dichloro-3-fluorobenzoyl chloride to react with 2-amino-5-bromonicotinohydrazide, 2-amino-5-bromo-N'-(cyclohexanecarbonyl)nicotinohydrazide was obtained as a white solid in 16% yield. $^1$H NMR (400 MHz, DMSO-d$_6$): δ10.26 (br s, 1H), 9.75 (br s, 1H), 8.16 (d, J=2.4 Hz, 1H), 8.08 (d, J=2.4 Hz, 1H), 7.18 (br s, 2H), 2.26-2.17 (m, 1H), 1.75-1.66 (m, 4H), 1.64-1.56 (m, 1H), 1.42-1.30 (m, 2H), 1.39-1.11 (m, 3H).

Preparation 10

Preparation of 5-bromo-3-(5-(pyridin-2-yl)-1,3,4-oxadiazol-2-yl)pyridin-2-Amine

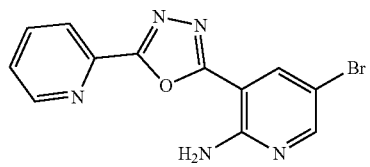 [SMILES: Nc1ncc(Br)cc1-c1nnc(-c2ccccn2)o1]

Picolinic acid (149 mg, 99%, 1.20 mmol), 2-amino-5-bromo-N'-nicotinoylnicotinohydrazide (231 mg, 1.00 mmol) and 1-[bis(dimethylamino)methylene]-1H-1,2,3-triazolo[4,5-b]pyridinium 3-oxid hexafluorophosphate (576 mg, 1.50 mmol) were dissolved in N,N-dimethylformamide (3.0 mL), followed by the addition of triethylamine (0.282 mL, 2.00 mmol). The resulting mixture was stirred at ambient temperature overnight, and then diluted with ethyl acetate (50 mL), washed with brine (2×50 mL), and dried over sodium sulfate. After filtration and removal of the solvent, the residue was dried under vacuum to afford a yellow solid N'-(2-amino-5-bromonicotinoyl)picolinohydrazide which was suspended in dichloromethane (20 mL), followed by the addition of triethylamine (0.697 mL, 5.00 mmol), triphenylphosphine (331 mg, 1.25 mmol) and carbon tetrachloride (419 mg, 99%, 1.25 mmol). The resulting mixture was stirred at ambient temperature for 3 hrs, and then concentrated. The residue was treated with methanol (5.0 mL), and filtered. The solid collected was washed with methanol and dried in vacuo to afford 5-bromo-3-(5-(pyridin-2-yl)-1,3,4-oxadiazol-2-yl)pyridin-2-amine as a yellow solid in 59% yield (188 mg). $^1$H NMR (400 MHz, CDCl$_3$): δ 8.84 (d, J=4.8 Hz, 1H), 8.40 (d, J=2.4 Hz, 1H), 8.33 (d, J=8.0 Hz, 1H), 8.28 (d, J=2.4 Hz, 1H), 7.98-7.90 (m, 1H), 7.68-7.64 (m, 1H), 6.90-6.70 (br s, 2H).

Preparation 10.1

Preparation of 5-Bromo-3-(5-(pyridin-3-yl)-1,3,4-oxadiazol-2-yl)pyridin-2-Amine

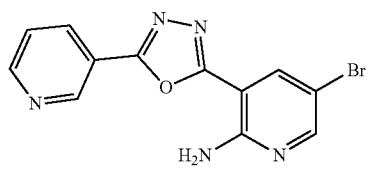 [SMILES: Nc1ncc(Br)cc1-c1nnc(-c2cccnc2)o1]

Following the procedure as described in Preparation 10, making variations using nicotinic acid to replace picolinic acid to react with 2-amino-5-bromonicotinohydrazide, 5-bromo-3-(5-(pyridin-3-yl)-1,3,4-oxadiazol-2-yl)pyridin-2-amine was obtained as a yellow solid in 62% yield. $^1$H NMR (400 MHz, CDCl$_3$): δ 9.38 (s, 1H), 8.84 (d, J=4.8 Hz, 1H), 8.42 (d, J=4.8 Hz, 1H), 8.30 (s, 1H), 8.22 (s, 1H), 7.53 (m, 1H), 6.85-6.55 (br s, 2H).

Preparation 10.2

Preparation of 5-bromo-3-(5-(pyrazin-2-yl)-1,3,4-oxadiazol-2-yl)pyridin-2-Amine

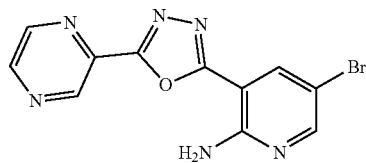 [SMILES: Nc1ncc(Br)cc1-c1nnc(-c2cnccn2)o1]

Following the procedure as described in Preparation 10, making variations using pyrazine-2-carboxylic acid to replace picolinic acid to react with 2-amino-5-bromonicotinohydrazide, 5-bromo-3-(5-(pyrazin-2-yl)-1,3,4-oxadiazol-2-yl)pyridin-2-amine was obtained as a yellowish solid in 57% yield. $^1$H NMR (400 MHz, CDCl$_3$): δ 9.33 (s, 1H), 8.64-8.60 (m, 2H), 8.18 (d, J=2.4 Hz, 1H), 8.10 (d, J=2.4 Hz, 1H), 7.20-7.05 (br s, 2H).

Preparation 10.3

Preparation of 3-(5-benzyl-1,3,4-oxadiazol-2-yl)-5-bromopyridin-2-amine

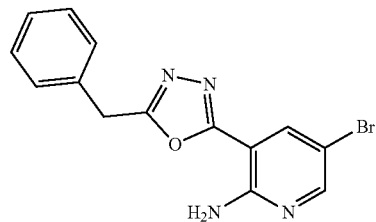 [SMILES: Nc1ncc(Br)cc1-c1nnc(Cc2ccccc2)o1]

Following the procedure as described in Preparation 10, making variations using 2-phenylacetic acid to replace picolinic acid to react with 2-amino-5-bromonicotinohydrazide, 3-(5-benzyl-1,3,4-oxadiazol-2-yl)-5-bromopyridin-2-amine was obtained as a white solid in 49% yield. $^1$H NMR (400 MHz, CDCl$_3$): δ 8.21 (d, J=2.4 Hz, 1H), 8.02 (d, J=2.4 Hz, 1H), 7.41-7.29 (m, 5H), 6.80-6.55 (br s, 2H), 4.28 (s, 2H).

Preparation 10.4

Preparation of 5-bromo-3-(5-(cyclopropylmethyl)-1,3,4-oxadiazol-2-yl)pyridin-2-amine

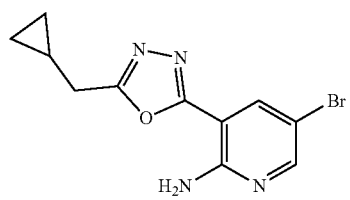 [SMILES: Nc1ncc(Br)cc1-c1nnc(CC2CC2)o1]

Following the procedure as described in Preparation 10, making variations using 2-cyclopropylacetic acid to replace picolinic acid to react with 2-amino-5-bromonicotinohydrazide, 5-bromo-3-(5-(cyclopropylmethyl)-1,3,4-oxadiazol-2-yl)-pyridin-2-amine was obtained as a yellowish solid in 38% yield. $^1$H NMR (400 MHz, CDCl$_3$): δ 8.24 (d, J=2.4 Hz, 1H), 8.10 (d, J=2.4 Hz, 1H), 6.85-6.60 (br s, 2H), 2.85 (d, J=7.2 Hz, 2H), 1.27-1.16 (m, 1H), 0.71-0.65 (m, 2H), 0.39-0.36 (m, 2H).

Preparation 10.5

Preparation of 5-bromo-3-(5-(thiazol-2-yl)-1,3,4-oxadiazol-2-yl)pyridin-2-amine

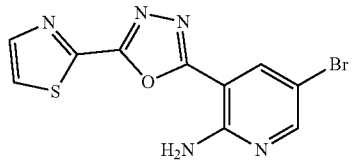

Following the procedure as described in Preparation 10, making variations using thiazole-2-carboxylic acid to replace picolinic acid to react with 2-amino-5-bromonicotinohydrazide, 5-bromo-3-(thiazol-2-yl)-1,3,4-oxadiazol-2-yl)pyridin-2-amine was obtained as a yellow solid in 53% yield. $^1$H NMR (400 MHz, CDCl$_3$): δ 7.90 (d, J=2.4 Hz, 1H), 7.87 (d, J=2.4 Hz, 1H), 7.73 (d, J=3.2 Hz, 1H), 7.46 (d, J=3.2 Hz, 1H), 7.00-6.85 (br s, 2H).

Preparation 10.6

Preparation of 5-bromo-3-(5-(4-(trifluoromethyl)thiazol-2-yl)-1,3,4-oxadiazol-2-yl)pyridin-2-amine

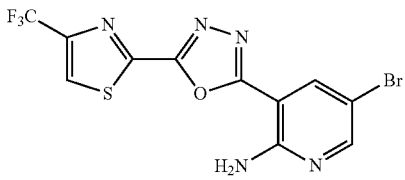 [SMILES: Nc1ncc(Br)cc1-c1nnc(-c2nc(C(F)(F)F)cs2)o1]

Following the procedure as described in Preparation 10, making variations using 4-(trifluoromethyl)thiazole-2-carboxylic acid to replace picolinic acid to react with 2-amino-5-bromonicotinohydrazide, 5-bromo-3-(5-(4-(trifluoromethyl)-thiazol-2-yl)-1,3,4-oxadiazol-2-yl)pyridin-2-amine was obtained as a yellow solid in 35% yield. $^1$H NMR (400 MHz, CDCl$_3$): δ 8.37 (d, J=2.4 Hz, 1H), 8.32 (d, J=2.4 Hz, 1H), 8.07 (s, 1H), 6.85-6.55 (br s, 2H).

Preparation 11

Preparation of 5-bromo-3-(5-(2,6-dichloro-3-fluorophenyl)-1,3,4-oxadiazol-2-yl)pyridin-2-amine

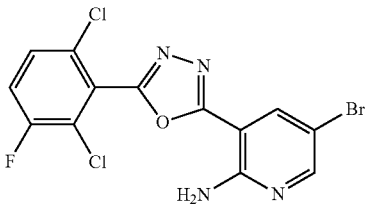

To a suspension of 2-amino-5-bromo-N'-(2,6-dichloro-3-fluorobenzoyl)-nicotinohydrazide (0.34 g, 0.81 mmol) in 20 mL of dichloromethane were added triethylamine (0.59 mL, 4.30 mmol), triphenylphosphine (0.28 g, 1.05 mmol) and tetrabromomethane (CBr$_4$) (0.35 g, 1.05 mmol). The mixture was stirred for 18 h, and evaporated. The residue was purified by flash chromatography eluted with ethyl acetate/dichloromethane (1/20) to afford 5-bromo-3-(5-(2,6-dichloro-3-fluorophenyl)-1,3,4-oxadiazol-2-yl)pyridin-2-amine as a pale brown solid in 38% yield (0.125 g). $^1$H NMR (400 MHz, DMSO-d$_6$): δ 8.32 (d, J=2.4 Hz, 1H), 8.20 (d, J=2.4 Hz, 1H), 7.88-7.81 (m, 2H), 7.53 (br s, 2H).

Preparation 11.1

Preparation of 5-bromo-3-(5-phenyl-1,3,4-oxadiazol-2-yl)pyridin-2-amine

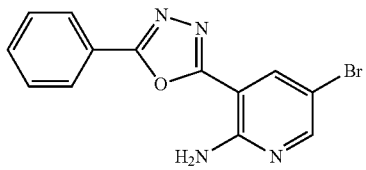

Following the procedure as described in Preparation 11, making variations using 2-amino-N'-benzoyl-5-bromonicotinohydrazide to replace 2-amino-5-bromo-N'-(2,6-dichloro-3-fluorobenzoyl)nicotinohydrazide, 5-bromo-3-(5-phenyl-1,3,4-oxadiazol-2-yl)pyridin-2-amine was obtained as a white solid in 89% yield. $^1$H NMR (400 MHz, DMSO-d$_6$): δ 8.44 (d, J=2.4 Hz, 1H), 8.28 (d, J=2.4 Hz, 1H), 8.21-8.16 (m, 2H), 7.65-7.57 (m, 3H), 7.48 (br s, 2H).

Preparation 11.2

Preparation of 5-bromo-3-(5-(4-(tert-butyl)phenyl)-1,3,4-oxadiazol-2-yl)pyridin-2-amine

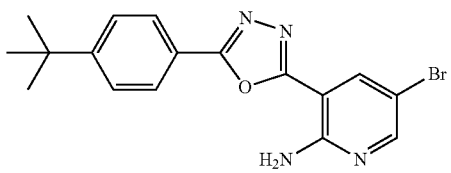 [SMILES: CC(C)(C)c1ccc(-c2nnc(-c3cc(Br)cnc3N)o2)cc1]

Following the procedure as described in Preparation 11, making variations using 2-amino-5-bromo-N'-(4-(tert-butyl)benzoyl)nicotinohydrazide to replace 2-amino-5-bromo-N'-(2,6-dichloro-3-fluorobenzoyl)nicotinohydrazide, 5-bromo-3-(5-(4-(tert-butyl)-phenyl)-1,3,4-oxadiazol-2-yl)pyridin-2-amine was obtained as a white solid in 82% yield. $^1$H NMR (400 MHz, DMSO-$d_6$): δ 8.42 (d, J=2.4 Hz, 1H), 8.27 (d, J=2.4 Hz, 1H), 8.12-8.08 (m, 2H), 7.64-7.59 (m, 2H), 7.49 (br s, 2H), 1.31 (s, 9H).

Preparation 11.3

Preparation of 5-bromo-3-(5-(2,5-difluorophenyl)-1,3,4-oxadiazol-2-yl)pyridin-2-amine

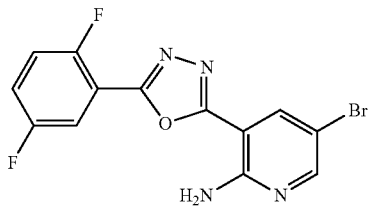 [SMILES: Nc1ncc(Br)cc1-c1nnc(-c2cc(F)ccc2F)o1]

Following the procedure as described in Preparation 11, making variations using 2-amino-5-bromo-N'-(2,5-difluorobenzoyl)nicotinohydrazide to replace 2-amino-5-bromo-N'-(2,6-dichloro-3-fluorobenzoyl)nicotinohydrazide, 5-bromo-3-(5-(2,5-difluoro-phenyl)-1,3,4-oxadiazol-2-yl)pyridin-2-amine was obtained as a pale yellow solid in 87% yield. $^1$H NMR (400 MHz, DMSO-$d_6$): δ 8.47 (d, J=2.4 Hz, 1H), 8.29 (d, J=2.4 Hz, 1H), 8.23-8.17 (m, 1H), 7.59-7.53 (m, 2H), 7.49 (br s, 2H).

Preparation 11.4

Preparation of 5-bromo-3-(5-(2,6-dichlorophenyl)-1,3,4-oxadiazol-2-yl)pyridin-2-amine

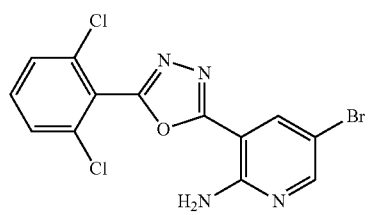 [SMILES: Nc1ncc(Br)cc1-c1nnc(-c2c(Cl)cccc2Cl)o1]

Following the procedure as described in Preparation 11, making variations using 2-amino-5-bromo-N'-(2,6-dichlorobenzoyl)nicotinohydrazide to replace 2-amino-5-bromo-N'-(2,6-dichloro-3-fluorobenzoyl)nicotinohydrazide, 5-bromo-3-(5-(2,6-dichloro-phenyl)-1,3,4-oxadiazol-2-yl)pyridin-2-amine was obtained as a white solid in 70% yield. $^1$H NMR (400 MHz, DMSO-$d_6$): δ 8.31 (d, J=2.4 Hz, 1H), 8.20 (d, J=2.4 Hz, 1H), 7.78-7.70 (m, 3H), 7.53 (br s, 2H).

Preparation 11.5

Preparation of 5-bromo-3-(5-(4-fluorophenyl)-1,3,4-oxadiazol-2-yl)-pyridin-2-amine

Following the procedure as described in Preparation 11, making variations using 2-amino-5-bromo-N'-(4-fluorobenzoyl)nicotinohydrazide to replace 2-amino-5-bromo-N'-(2,6-dichloro-3-fluorobenzoyl)nicotinohydrazide, 5-bromo-3-(5-(4-fluorophenyl)-1,3,4-oxadiazol-2-yl)pyridin-2-amine was obtained as a pale yellow solid in 83% yield. $^1$H NMR (400 MHz, DMSO-$d_6$): δ 8.47 (d, J=2.4 Hz, 1H), 8.28 (d, J=2.4 Hz, 1H), 8.27-8.23 (m, 2H), 7.48 (br s, 2H), 7.48-7.42 (m, 2H).

Preparation 12

Preparation of 1-cyclohexyl-4-(4,4,5,5-tetramethyl-1,3,2-dioxaborolan-2-yl)-1H-pyrazole

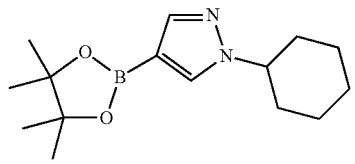 [SMILES: CC1(C)OB(c2cnn(C3CCCCC3)c2)OC1(C)C]

1. To a cooled (0° C.) solution of cyclohexanol (2.50 g, 25.0 mmol) in dichloromethane (50 mL) was added triethylamine (7.00 mL, 50.0 mmol), followed by the addition of methanesulfonyl chloride (2.91 mL, 37.5 mmol). The mixture was stirred at ambient temperature for 20 h, diluted with dichloromethane (50 mL), washed with 1 N hydrochloroic acid solution (20 mL), saturated sodium bicarbonate (30 mL), water (30 mL), brine (30 mL) and dried. The crude cyclohexyl methanesulfonate was obtained as pale yellow oil after removal of the solvent (4.47 g, 100% yield). 1H NMR (300 MHz, CDCl$_3$): δ 4.75-4.67 (m, 1H), 3.00 (s, 3H), 2.04-1.95 (m, 2H), 1.83-1.74 (m, 2H), 1.70-1.59 (m, 2H), 1.57-1.49 (m, 1H), 1.46-1.25 (m, 3H).

2. To a cooled (0° C.) solution of 4-bromo-1H-pyrazole (2.21 g, 15.0 mmol) in dimethylformamide (25 mL) was added 60% sodium hydride (0.900 g, 22.5 mmol) in portions. After 30 min, a solution of cyclohexyl methanesulfonate (2.84 g, 16.0 mmol) in dimethylformamide (4 mL) was added. The mixture was heated at 105° C. for 20 h. The volatiles were removed in vacuo and the residue was diluted with ethyl acetate (100 mL), washed with water (2×20 mL), brine (20 mL) and dried. The residue after removal of the solvents was purified by flash column chromatography eluted with 5% ethyl acetate in hexanes to afford 4-bromo-1-cyclohexyl-1H-pyrazole as a white solid in 33% yield (1.14 g). $^1$H NMR (400 MHz, CDCl$_3$): δ 7.45 (s, 1H), 7.44

(s, 1H), 4.13-4.05 (m, 1H), 2.18-2.10 (m, 2H), 1.94-1.86 (m, 2H), 1.75-1.62 (m, 3H), 1.48-1.36 (m, 2H), 1.31-1.19 (m, 1H).

3. To a solution of 4-bromo-1-cyclohexyl-1H-pyrazole (1.13 g, 4.95 mmol) in dimethyl sulfoxide (10 mL) was added potassium acetate (1.47 g, 15 mmol), pinacol diboron (1.52 g, 6.00 mmol). The mixture was degassed for 10 min, followed by the addition of PdCl$_2$(dppf) (0.300 g, 0.400 mmol). The mixture was degassed for another 10 min and heated at 90° C. for 20 h, diluted with ethyl acetate (80 mL), washed with water (2×20 mL), brine (20 mL) and dried. The residue after removal of the solvents was purified by flash column chromatography eluted with 10% ethyl acetate in hexanes to afford 1-cyclohexyl-4-(4,4,5,5-tetramethyl-1,3,2-dioxaborolan-2-yl)-1H-pyrazole as a white solid in 20% yield (0.265 g). $^1$H NMR (300 MHz, CDCl$_3$) δ 7.80 (s, 1H), 7.75 (s, 1H), 4.21-4.11 (m, 1H), 2.21-2.14 (m, 2H), 1.94-1.85 (m, 2H), 1.77-1.65 (m, 3H), 1.48-1.34 (m, 3H), 1.32 (s, 12H).

Preparation 13

Preparation of N'-hydroxybenzamidine

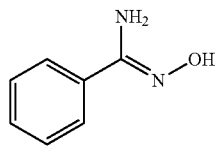

A mixture of benzonitrile (5.00 g, 48.5 mmol), hydroxylamine hydrochloride (8.42 g, 121 mmol) and triethylamine (30 mL) was refluxed in 30 mL of ethanol for 7 hours. After removal of solvent in vacuo, the residue (white suspension) was mixed with water and extracted with ethyl acetate (3×50 mL). The collected organic solution was dried over sodium sulfate. N'-hydroxybenzamidine was obtained as a grey gum in 70% yield (4.60 g) after the removal of the solvent in vacuo. $^1$H NMR (400 MHz, CDCl$_3$): δ7.65-7.60 (m, 2H), 7.46-7.35 (m, 3H), 4.95 (br s, 2H).

Preparation 13.1

Preparation of (Z)-2,6-dichloro-N'-hydroxybenzamidine

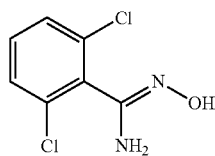 [SMILES: N/C(=N\O)c1c(Cl)cccc1Cl]

Following the procedure as described in Preparation 13, making variations using 2,6-dichlorobenzonitrile to replace benzonitrile, (Z)-2,6-dichloro-N'-hydroxybenzamidine was obtained as a white solid in 37% yield. $^1$H NMR (400 MHz, DMSO-d$_6$): δ 9.38 (s, 1H), 7.48-7.45 (m, 2H), 7.41-7.35 (m, 1H), 5.88 (br s, 2H).

Preparation 14

Preparation of N'-((2-amino-5-bromonicotinoyl)oxy)benzimidamide

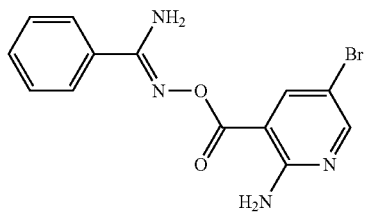 [SMILES: N/C(=N\OC(=O)c1cc(Br)cnc1N)c1ccccc1]

To a mixture of N'-hydroxybenzamidine (0.50 g, 3.68 mmol) and 2-amino-5-bromopyridine-3-carboxylic acid (0.83 g, 4.05 mmol) in 30 mL of dichloromethane was added 1-ethyl-3-(3-dimethylaminopropyl)carbodiimide (1.45 g, 7.36 mmol). The resulting mixture was stirred at ambient temperature overnight. After removal of solvent in vacuo, the residue was purified by column chromatography eluted with 5% methanol in dichloromethane to afford a yellow oil which was treated with dichloromethane and ethyl ether to afford N'-((2-amino-5-bromonicotinoyl)oxy)-benzimidamide as a yellow solid in 32% yield (0.25 g). $^1$H NMR (400 MHz, DMSO-d$_6$): δ8.61 (d, J=2.4 Hz, 1H), 8.25 (d, J=2.4 Hz, 1H), 7.74-7.70 (m, 2H), 7.52-7.42 (m, 3H), 7.34 (br s, 2H), 7.04 (br s, 2H).

Preparation 14.1

Preparation of (Z)—N'-((2-amino-5-bromonicotinoyl)oxy)-2,6-dichlorobenzimidamide

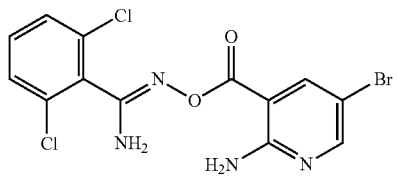 [SMILES: N/C(=N\OC(=O)c1cc(Br)cnc1N)c1c(Cl)cccc1Cl]

Following the procedure as described in Preparation 14, making variations using (Z)-2,6-dichloro-N'-hydroxybenzamidine to replace N'-hydroxybenzamidine to react with 2-amino-5-bromopyridine-3-carboxylic acid, (Z)—N'-((2-amino-5-bromonicotinoyl)oxy)-2,6-dichlorobenzimidamide was obtained as a yellowish solid in 41% yield. $^1$H NMR (400 MHz, DMSO-d$_6$): δ 8.67 (d, J=2.4 Hz, 1H), 8.25 (d, J=2.4 Hz, 1H), 7.56-7.46 (m, 3H), 7.34 (br s, 4H).

Preparation 15

Preparation of 5-bromo-3-(3-phenyl-1,2,4-oxadiazol-5-yl)pyridin-2-amine

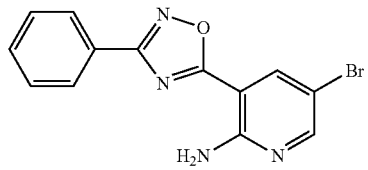 [SMILES: Nc1ncc(Br)cc1-c1nc(-c2ccccc2)no1]

A solution of N'-((2-amino-5-bromonicotinoyl)oxy)benzimidamide (0.30 g, 0.90 mmol) in 5 mL of pyridine was refluxed for 3 hours. After cooling, precipitates were formed. After removal of pyridine by gravity filtration, the precipitates were washed with water to afford 5-bromo-3-(3-phenyl-1,2,4-oxadiazol-5-yl)pyridin-2-amine as a yellowish solid in 92% yield (0.25 g). $^1$H NMR (400 MHz, DMSO-d$_6$): δ8.35 (d, J=2.4 Hz, 1H), 8.32 (d, J=2.4 Hz, 1H), 8.15-8.10 (m, 2H), 7.66 (br s, 2H), 7.60-7.54 (m, 3H).

Preparation 15.1

Preparation of 5-bromo-3-(3-(2,6-dichlorophenyl)-1,2,4-oxadiazol-5-yl)pyridin-2-amine

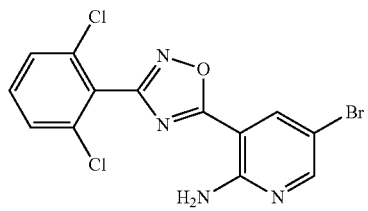 [SMILES: Nc1ncc(Br)cc1-c1nc(-c2c(Cl)cccc2Cl)no1]

Following the procedure as described in Preparation 15, making variations using N-((2-amino-5-bromonicotinoyl)oxy)-2,6-dichlorobenzimidamide to replace N'-((2-amino-5-bromonicotinoyl)oxy)benzimidamide, 5-bromo-3-(3-(2,6-dichlorophenyl)-1,2,4-oxadiazol-5-yl)pyridin-2-amine was obtained as a yellowish solid in 67% yield. $^1$H NMR (400 MHz, CDCl$_3$): δ 8.43 (d, J=2.4 Hz, 1H), 8.33 (d, J=2.0 Hz, 1H), 7.50-7.42 (m, 3H), 6.80 (br s, 2H).

Preparation 16

Preparation of (Z)-2-amino-5-bromo-N'-hydroxynicotinimidamide

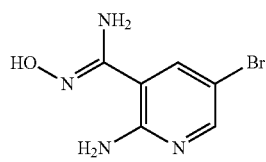

A solution of 2-amino-5-bromopyridine-3-carbonitrile (2.00 g, 10.1 mmol), hydroxylamine hydrochloride (1.06 g, 15.3 mmol) and 24 mL of triethylamine in 40 mL of ethanol was refluxed for 3 h. The resulting mixture was poured into ice cold water to afford a white solid. The solid was separated by filtration and washed with water. The filtrate was extracted with ethyl acetate and the organic layers were combined, dried over anhydrous sodium sulfate and filtered. The filtrate was evaporate to afford a white solid which was combined with the white solid obtained earlier to afford (Z)-2-amino-N'-(benzoyloxy)-5-bromonicotinimidamide in quantitative yield (2.30 g). $^1$H NMR (400 MHz, DMSO-d$_6$): δ9.95 (s, 1H), 7.96 (d, J=2.4 Hz, 1H), 7.89 (d, J=2.4 Hz, 1H), 7.20 (br s, 2H), 5.93 (s, 2H).

Preparation 17

Preparation of 5-bromo-3-(5-phenyl-1,2,4-oxadiazol-3-yl)pyridin-2-amine

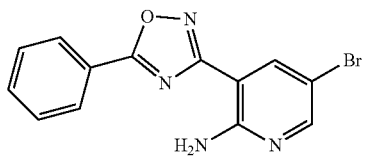 [SMILES: Nc1ncc(Br)cc1-c1noc(-c2ccccc2)n1]

A. A mixture of benzoic acid (319 mg, 2.60 mmol), 2-amino-5-bromo-N-hydroxypyridine-3-carboxamidine (400 mg, 1.73 mmol) and 1-ethyl-3-(3-dimethylaminopropyl)carbodiimide (627 mg, 3.24 mmol) in dichloromethane (10 mL) was stirred at ambient temperature for 5 hours and a white solid was precipitated. The solid was collected by filtration, washed with dichloromethane, and dried in vacuo to afford (Z)-2-amino-N'-(benzoyloxy)-5-bromonicotinimidamide as a white solid in 73% yield (422 mg). $^1$H NMR (400 MHz, DMSO-d$_6$): δ 8.18 (dd, J=8.0, 1.2 Hz, 2H), 8.10 (d, J=2.4 Hz, 1H), 8.00 (d, J=2.4 Hz, 1H), 7.66 (t, J=8.0 Hz, 1H), 7.52 (t, J=8.0 Hz, 2H), 7.29 (br s, 2H), 7.04 (br s, 2H).

B. A suspension of (Z)-2-amino-N'-(benzoyloxy)-5-bromo-nicotinimidamide (405 mg, 1.21 mmol) in pyridine (6.0 mL, 77.0 mmol) was stirred at 110-115° C. overnight. After cooled to ambient temperature, the reaction mixture was concentrated under high vacuum. The residue was azeotroped with toluene (4×10 mL), and dried under vacuum for 30 minutes. The dried residue was treated with methanol (10 mL), and a precipitate was obtained. The precipitate was collected by filtration, and washed with methanol (~20 mL), and dried under vacuum to afford 5-bromo-3-(5-phenyl-1,2,4-oxadiazol-3-yl)pyridin-2-amine as a yellow solid (285 mg, 74%). $^1$H NMR (400 MHz, CDCl$_3$): δ 8.56 (d, J=2.4 Hz, 1H), 8.27 (d, J=2.4 Hz, 1H), 8.25-8.20 (m, 2H), 7.68-7.63 (m, 1H), 7.62-7.56 (m, 2H), 6.30-6.17 (br s, 2H).

Preparation 18

Preparation of 5-bromo-3-(5-(2,5-dichlorophenyl)-1,2,4-oxadiazol-3-yl)pyridin-2-amine

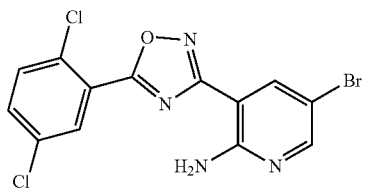 [SMILES: Nc1ncc(Br)cc1-c1noc(-c2cc(Cl)ccc2Cl)n1]

A. To a solution of 2-amino-5-bromo-N-hydroxypyridine-3-carboxamidine (74 mg, 0.344 mmol) and 2,5-dichlorobenzoic acid (72 mg, 0.378 mmol) in 5 mL of dichloromethane was added 1-ethyl-3-(3-dimethylaminopropyl)-carbodiimide (98 mg, 0.516 mmol) and 1 mL of N,N-dimethylformamide. The mixture was stirred at ambient temperature overnight, followed by the addition of water to quench the reaction. The resulting mixture was extracted with dichloromethane (2×10 mL). The combined organic solution was dried over anhydrous sodium sulfate. After filtration and removal of solvent, the residue was purified by flash column chromatography to afford (Z)-2-amino-5-bromo-N'-((2,5-dichlorobenzoyl)oxy)-nicotinimidamide as a white solid in 72% yield (96 mg). $^1$H NMR (400 MHz, DMSO-d$_6$): δ8.12 (d, J=2.4 Hz, 1H), 8.11 (d, J=2.4 Hz, 1H), 7.97 (d, J=2.4 Hz, 1H), 7.65 (dd, J=8.0, 2.4 Hz, 1H), 7.62 (d, J=8.0 Hz, 1H), 7.19 (br s, 2H), 7.08 (br s, 2H).

B. A solution of (Z)-2-amino-5-bromo-N'-((2,5-dichlorobenzoyl)oxy)-nicotinimidamide (170 mg, 0.463 mmol) in 5 mL of pyridine was refluxed for 2 h. The reaction mixture was cooled to room temperature and pyridine was removed in vacuo. The resulting white solid was washed with water and collected by filtration. The collected white solid was washed with a mixture of ethyl acetate:dichloromethane (1:10) to remove the remaining starting material to afford pure 5-bromo-3-(5-(2,5-dichlorophenyl)-1,2,4-oxadiazol-3-yl)pyridin-2-amine as a yellow solid in 34% yield (60 mg). $^1$H NMR (400 MHz, DMSO-d$_6$): δ8.35 (d, J=2.4 Hz, 1H), 8.31-8.28 (m, 2H), 7.82-7.77 (m, 2H), 7.12 (br s, 2H).

Preparation 19

Preparation of tert-butyl 4-(4-(4,4,5,5-tetramethyl-1,3,2-dioxaborolan-2-yl)-1H-pyrazol-1-yl)piperidine-1-carboxylate

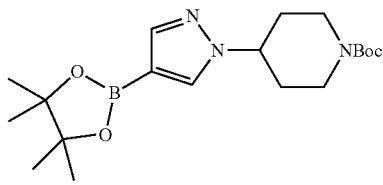 [SMILES: CC(C)(C)OC(=O)N1CCC(n2cc(B3OC(C)(C)C(C)(C)O3)cn2)CC1]

A. To a cold solution (0° C.) of tert-butyl 4-hydroxypiperidine-1-carboxylate (175 g, 0.87 mol) in 750 mL of dichloromethane was added triethylamine (237 mL, 1.74 mol) dropwise, followed by the addition of mesyl chloride (101 mL, 1.31 mol) dropwise. The resulting mixture was stirred at room temperature for 2 hours, then diluted with 400 mL of dichloromethane and washed with saturated sodium bicarbonate (2×750 mL), water (1×600 mL) and brine (1×600 mL). The organic solution was dried over anhydrous sodium sulfate, and filtered. Removal of the solvent afforded tert-butyl 4-((methylsulfonyl)oxy)piperidine-1-carboxylate as a yellow solid in 96.8% yield (235 g). $^1$H NMR (400 MHz, CDCl$_3$) δ 4.90-4.82 (m, 1H), 3.73-3.64 (m, 2H), 3.34-3.25 (m, 2H), 3.03 (s, 3H), 2.00-1.92 (m, 2H), 1.88-1.75 (m, 2H), 1.44 (s, 9H).

B. To a cold solution (0° C.) of 4-bromo-1H-pyrazole (14.9 g, 0.10 mol) in 80 mL of dichloromethane was added sodium hydride (8.13 g, 0.20 mol) portion wise. The mixture was stirred at 0° C. for 1 hour, followed by the addition of a solution of tert-butyl 4-((methylsulfonyl)oxy)piperidine-1-carboxylate (34.0 g, 0.12 mol) in 30 mL of N,N-dimethylformamide. The resulting mixture was heated at 110° C. overnight. Purification by column chromatography afforded tert-butyl 4-(4-bromo-1H-pyrazol-1-yl)piperidine-1-carboxylate as a yellow oil in 58% yield (19.5 g). $^1$H NMR (400 MHz, CDCl$_3$) δ 7.48 (s, 1H), 7.44 (s 1H), 4.35-4.20 (m, 3H), 2.95-2.85 (m, 2H), 2.15-2.05 (m, 2H), 1.92-1.81 (m, 2H), 1.48 (s, 9H).

C. A mixture of tert-butyl 4-(4-bromo-1H-pyrazol-1-yl)piperidine-1-carboxylate (20.0 g, 0.61 mmol), 4,4,5,5-tetramethyl-2-(4,4,5,5-tetramethyl-1,3,2-dioxaborolan-2-yl)-1,3,2-dioxaborolane (30.8 g, 0.12 mmol) and potassium acetate (17.8 g, 0.18 mol) in 50 mL of dimethyl sulfoxide was purged with nitrogen gas for 10 min. After the addition of [1,1'-bis(diphenylphosphino)ferrocene]dichloropalladium(II) (3.55 g, 4.85 mmol), the mixture was purged with nitrogen gas for another 10 minutes, heated at 80° C. overnight under nitrogen atmosphere and filtered through celite and washed with ethyl acetate. The filtrate was extracted with ethyl acetate (2×200 mL). The organic layer was dried over anhydrous sodium sulfate. After filtration and removal of the solvent, the residue was purified by column chromatograph eluted with hexane to afford an oil which was recrystallized from hexane to afford tert-butyl 4-(4-(4,4,5,5-tetramethyl-1,3,2-dioxaborolan-2-yl)-1H-pyrazol-1-yl)piperidine-1-carboxylate as a white solid in 44% yield (10 g). $^1$H NMR (400 MHz, CDCl$_3$) δ 7.79 (s, 1H), 7.72 (s, 1H), 4.32-4.13 (m, 3H), 2.95-2.80 (m, 2H), 2.15-2.05 (m, 2H), 1.93-1.82 (m, 2H), 1.47 (s, 9H), 1.31 (s, 12H).

Preparation 20

Preparation of 5-bromo-3-(5-cyclohexyl-1,3,4-oxadiazol-2-yl)pyridin-2-amine

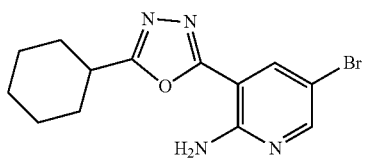 [SMILES: Nc1ncc(Br)cc1-c1nnc(C2CCCCC2)o1]

To a suspension of 2-amino-5-bromo-N'-(cyclohexanecarbonyl)-nicotinohydrazide (0.20 g, 0.59 mmol) in 15 mL of dichloromethane was added triethylamine (0.40 mL, 2.93 mmol) and acetic anhydride (13 μL, 0.14 mmol), followed by the addition of triphenylphosphine (0.19 g, 0.73 mmol) and tetrabromomethane (0.24 g, 0.73 mmol). The resulting mixture was stirred at room temperature for 2 hours. After removal of the solvent in vacuo, the residue was purified by column chromatography eluted with 1:1 ethyl acetate:hexane to afford 5-bromo-3-(5-cyclohexyl-1,3,4-oxadiazol-2-yl)pyridin-2-amine as a white solid in 77% yield (0.14 g). $^1$H NMR (400 MHz, CDCl$_3$): δ8.23 (d, J=2.4 Hz, 1H), 8.07 (d, J=2.4 Hz, 1H), 6.61 (br s, 2H), 3.04-2.95 (m, 1H), 2.20-2.10 (m, 2H), 1.94-1.84 (m, 2H), 1.80-1.60 (m, 3H), 1.50-1.30 (m, 3H).

Preparation 21

Preparation of tert-butyl 4-(3-(4,4,5,5-tetramethyl-1,3,2-dioxaborolan-2-yl)-1H-pyrrol-1-yl)piperidine-1-carboxylate

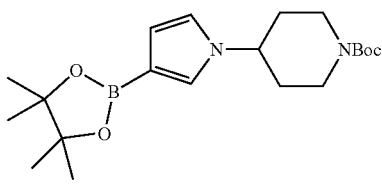 [SMILES: CC(C)(C)OC(=O)N1CCC(n2ccc(B3OC(C)(C)C(C)(C)O3)c2)CC1]

A. To an ice-cold solution of pyrrole (611 mg, 9.11 mmol) in 6 mL of N,N-dimethylformamide was slowly added sodium hydride (364 mg, 9.11 mmol, 60% in mineral oil). After stirred at room temperature for 1 hour, the resulting mixture was cooled to 0° C., followed by the addition of 1-(tert-butoxycarbonyl)piperidin-4-yl methanesulfonate slowly. The mixture was then heated up to 110° C. and stirred overnight. After removal of the solvent in vacuo, the residue was purified by column chromatography eluted with 20% ethyl acetate in hexane to afford tert-butyl 4-(1H-pyrrol-1-yl)piperidine-1-carboxylate as a colorless oil in 21% yield (317 mg). $^1$H NMR (400 MHz, CDCl$_3$): δ 6.75-6.71 (m, 2H), 6.18-6.15 (m, 2H), 4.32-4.20 (m, 2H), 4.02-3.93 (m, 1H), 2.90-2.76 (m, 2H), 2.07-2.03 (m, 2H), 1.89-1.78 (m, 2H), 1.48 (s, 9H).

B. To a solution of tert-butyl 4-(1H-pyrrol-1-yl)piperidine-1-carboxylate (1.03 g, 3.72 mmol) in 30 mL of anhydrous tetrahydrofuran at −78° C. was added phosphorus tribromide (60 mg, 0.220 mmol) and N-bromosuccinimide (663 mg, 3.72 mmol) in sequence. The mixture was stirred at −78° C. for 1 hour, and it was left in the freezer (−15° C.) overnight. A white solid was precipitated after the addition of triethylamine (0.42 g, 1 equiv) and hexanes (40 mL) to the mixture. The suspension was filtered through neutral aluminium oxide pad and dried over sodium sulfate. The removal of the solvent of the filtrate afforded tert-butyl 4-(3-bromo-1H-pyrrol-1-yl)piperidine-1-carboxylate (1.23 g) as yellowish oil which was used for the next step reaction without further purification. $^1$H NMR (400 MHz, CDCl$_3$): δ 6.71-6.69 (m, 1H), 6.63-6.61 (m, 1H), 6.16-6.13 (m, 1H), 4.35-4.20 (m, 2H), 3.95-3.85 (m, 1H), 2.89-2.76 (m, 2H), 2.06-1.98 (m, 2H), 1.89-1.76 (m, 2H), 1.47 (s, 9H).

C. A solution of tert-butyl 4-(3-bromo-1H-pyrrol-1-yl)piperidine-1-carboxylate (1.23 g, 3.7 mmol), bis(pinacolato)diboron (1.90 g, 7.4 mmol) and potassium acetate (1.09 g, 11.1 mmol) in 20 mL of dioxane in a sealed tube was degassed with nitrogen gas for 10 min, followed by the addition of 1,1'-bis(diphenylphosphino)ferrocene-palladium (II) dichloride (270 mg, 0.37 mmol). The mixture was degassed for another 10 min. The tube was sealed and heated at 80° C. overnight. The resulting solution was washed with water and extracted with ethyl acetate. Organic layers were combined and evaporated and the residue was purified by column chromatography eluted with 15% ethyl acetate in hexanes to afford tert-butyl 4-(3-(4,4,5,5-tetramethyl-1,3,2-dioxaborolan-2-yl)-1H-pyrrol-1-yl)piperidine-1-carboxylate as colorless oil in 14% yield (70 mg). $^1$H NMR (400 MHz, CDCl$_3$): δ 7.19-7.17 (m, 1H), 6.76-6.74 (m, 1H), 6.51-6.49 (m, 1H), 4.28-4.19 (m, 2H), 4.02-3.92 (m, 1H), 2.86-2.78 (m, 2H), 2.04-2.01 (m, 2H), 1.88-1.78 (m, 2H), 1.48 (s, 9H), 1.32 (s, 12H).

Preparation 22

Preparation of 1-(tetrahydro-2H-pyran-4-yl)-4-(4,4,5,5-tetramethyl-1,3,2-dioxaborolan-2-yl)-1H-pyrazole

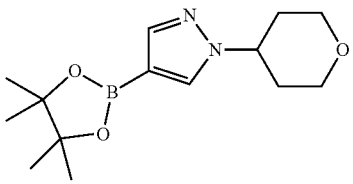 [SMILES: CC1(C)OB(c2cnn(C3CCOCC3)c2)OC1(C)C]

A. To a cooled (0° C.) solution of tetrahydro-2H-pyran-4-ol (5.00 g, 49.0 mmol) in dichloromethane (85 mL) was added triethylamine (5.95 mL, 58.8 mmol), followed by the addition of methanesulfonyl chloride (6.74 mL, 58.8 mmol). The mixture was stirred at room temperature overnight, diluted with dichloromethane (85 mL), then sequentially washed with 0.5 N hydrochloric acid solution (40 mL), saturated sodium bicarbonate (50 mL), water (50 mL), brine (50 mL), dried over anhydrous sodium sulfate and filtered. The filtrate was evaporated to afford the crude product tetrahydro-2H-pyran-4-yl methanesulfonate (8.6 g, 97.4%) as a pale yellow solid. $^1$H NMR (400 Hz, CDCl$_3$) δ 4.95-4.85 (m, 1H), 3.97-3.90 (m, 2H), 3.57-3.51 (m, 2H), 3.04 (s, 3H), 2.08-2.02 (m, 2H), 1.93-1.84 (m, 2H).

B. To a cooled (0° C.) solution of 4-bromo-1H-pyrazole (3.00 g, 20.4 mmol) in N,N-dimethylformamide (10 mL) was added 60% sodium hydride (0.90 g, 22.5 mmol) in portions, followed by the addition of a solution of tetrahydro-2H-pyran-4-yl methanesulfonate (5.52 g, 30.6 mmol) in N,N-dimethylformamide (10 mL) 30 minutes later. The mixture was heated at 110° C. overnight, cooled to room temperature and mixed with water (50 mL). The precipitates obtained were collected by filtration, washed with water and dried to afford 4-bromo-1-(tetrahydro-2H-pyran-4-yl)-1H-pyrazole (2.90 g, 62%) as a brown solid. $^1$H NMR (400 Hz, CDCl$_3$) δ 7.47 (s, 1H), 7.46 (s, 1H), 4.35-4.30 (m, 1H), 4.12-4.08 (m, 2H), 3.55-3.48 (m, 2H), 2.15-2.00 (m, 4H).

C. To a solution of 4-bromo-1-(tetrahydro-2H-pyran-4-yl)-1H-pyrazole (2.90 g, 12.6 mmol) in dimethyl sulfoxide (25 mL) was added potassium acetate (4.94 g, 50.4 mmol), 4,4,5,5-tetramethyl-2-(4,4,5,5-tetramethyl-1,3,2-dioxaborolan-2-yl)-1,3,2-dioxaborolane (6.40 g, 25.2 mmol). The mixture was degassed for 10 min, and then [1,1'-bis(diphenylphosphino)ferrocene]dichloro-palladium(II) (0.922 g, 1.26 mmol) was added. The mixture was degassed for another 10 minutes and heated at 90° C. overnight, diluted with ethyl acetate (80 mL), washed with water (2×20 mL), brine (20 mL), dried and filtered. The solvent of the filtrate was removed and the residue was purified by flash column chromatography eluted with 20% ethyl acetate in hexanes to afford 1-(tetrahydro-2H-pyran-4-yl)-4-(4,4,5,5-tetramethyl-1,3,2-dioxaborolan-2-yl)-1H-pyrazole (0.66 g, 19%) as a white solid. $^1$H NMR (400 Hz, CDCl$_3$) δ 7.81 (s, 1H), 7.76 (s, 1H), 4.42-4.32 (m, 1H), 4.14-4.06 (m, 2H), 3.58-3.50 (m, 2H), 2.16-1.98 (m, 4H), 1.32 (s, 12H).

EXAMPLES

Example 1

Synthesis of tert-butyl 4-(4-(6-amino-5-(5-phenyl)-1,3,4-oxadiazol-2-yl)pyridin-3-yl)-1H-pyrazol-1-yl)piperidine-1-carboxylate

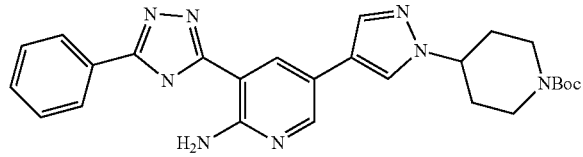 [SMILES: CC(C)(C)OC(=O)N1CCC(n2cc(-c3cnc(N)c(-c4nnc(-c5ccccc5)[nH]4)c3)cn2)CC1]

To a solution of 5-bromo-3-(5-phenyl-1,3,4-oxadiazol-2-yl)pyridin-2-amine (0.112 g, 0.353 mmol) in dimethyl sulfoxide (5 mL) were added tert-butyl 4-(4-(4,4,5,5-tetramethyl-1,3,2-dioxaborolan-2-yl)-1H-pyrazol-1-yl)piperidine-1-carboxylate (0.160 g, 0.424 mmol), potassium acetate (0.140 g, 1.40 mmol) and PdCl$_2$(dppf) (26.0 mg, 0.035 mmol). The mixture was degassed with nitrogen gas for 5 min, evaporated, heated at 100° C. for 20 h, cooled, diluted with 50 mL of ethyl acetate, washed with water (10 mL), and brine (10 mL). The organic phase was dried in vacuo and the residue was purified by flash chromatography eluted with 60% ethyl acetate in hexanes to afford the title compound as a pale brown solid in 24% yield (42 mg). $^1$H NMR (400 MHz, CDCl$_3$): δ 8.40 (d, J=2.0 Hz, 1H), 8.19-8.15 (m, 3H), 7.78 (d, J=0.8 Hz, 1H), 7.68 (d, J=0.8 Hz, 1H), 7.62-7.55 (m, 3H), 6.63 (br s, 2H), 4.38-4.23 (m, 3H), 3.00-2.87 (m, 2H), 2.23-2.16 (m, 2H), 2.06-1.83 (m, 2H), 1.50 (s, 9H).

The table below shows additional examples of compounds of Formula (IA4) that were prepared according to the above process.

| Ex. No. | Chemical Name | Starting Material and Yield | Characterization Data |
|---|---|---|---|
| 1.1 | tert-butyl 4-(4-(6-amino-5-(5-(2,6-dichloro-3-fluorophenyl)-1,3,4-oxadiazol-2-yl)pyridin-3-yl)-1H-pyrazol-1-yl)piperidine-1-carboxylate | 5-bromo-3-(5-(2,6-dichloro-3-fluorophenyl)-1,3,4-oxadiazol-2-yl)pyridin-2-amine and tert-butyl 4-(4-(4,4,5,5-tetramethyl-1,3,2-dioxaborolan-2-yl)-1H-pyrazol-1-yl)piperidine-1-carboxylate; 16% | $^1$H NMR (400 MHz, CDCl$_3$): δ 8.42 (d, J = 2.4 Hz, 1H), 8.10 (d, J = 2.4 Hz, 1H), 7.73 (d, J = 0.8 Hz, 1H), 7.64 (d, J = 0.8 Hz, 1H), 7.52-7.48 (m, 1H), 7.40-7.36 (m, 1H), 6.62 (br s, 2H), 4.35-4.22 (m, 3H), 2.96-2.84 (m, 2H), 2.18-2.12 (m, 2H), 1.98-1.91 (m, 2H), 1.46 (s, 9H). |
| 1.2 | tert-butyl 4-(4-(5-(5-(4-tert-butylphenyl)-1,3,4-oxadiazol-2-yl)-6-aminopyridin-3-yl)-1H-pyrazol-1-yl)piperidine-1-carboxylate | 3-(5-(4-tert-butylphenyl)-1,3,4-oxadiazol-2-yl)-5-bromopyridin-2-amine and tert-butyl 4-(4-(4,4,5,5-tetramethyl-1,3,2-dioxaborolan-2-yl)-1H-pyrazol-1-yl)piperidine-1-carboxylate; 22% | $^1$H NMR (400 MHz, CDCl$_3$): δ 8.39 (d, J = 2.4 Hz, 1H), 8.15 (d, J = 2.4 Hz, 1H), 8.11-8.07 (m, 2H), 7.78 (d, J = 0.8 Hz, 1H), 7.67 (d, J = 0.8 Hz, 1H), 7.60-7.56 (m, 2H), 6.61 (br s, 2H), 4.38-4.20 (m, 3H), 2.98-2.86 (m, 2H), 2.24-2.16 (m, 2H), 2.04-1.83 (m, 2H), 1.48 (s, 9H), 1.38 (s, 9H). |
| 1.3 | tert-butyl 4-(4-(6-amino-5-(5-(2,5-difluorophenyl)-1,3,4-oxadiazol-2-yl)pyridin-3-yl)-1H-pyrazol-1-yl)piperidine-1-carboxylate | 5-bromo-3-(5-(2,5-difluorophenyl)-1,3,4-oxadiazol-2-yl)pyridin-2-amine and tert-butyl 4-(4-(4,4,5,5-tetramethyl-1,3,2-dioxaborolan-2-yl)-1H-pyrazol-1-yl)piperidine-1-carboxylate; 18% | $^1$H NMR (400 MHz, CDCl$_3$): δ 8.41 (d, J = 2.4 Hz, 1H), 8.15 (d, J = 2.4 Hz, 1H), 7.90-7.84 (m, 1H), 7.77 (d, J = 0.8 Hz, 1H), 7.66 (d, J = 0.8 Hz, 1H), 7.30-7.26 (m, 2H), 6.60 (br s, 2H), 4.36-4.22 (m, 3H), 2.98-2.86 (m, 2H), 2.24-2.16 (m, 2H), 2.03-1.83 (m, 2H), 1.48 (s, 9H). |
| 1.4 | tert-butyl 4-(4-(6-amino-5-(5-(2,6-dichlorophenyl)-1,3,4-oxadiazol-2-yl)pyridin-3-yl)-1H-pyrazol-1-yl)piperidine-1-carboxylate | 5-bromo-3-(5-(2,6-dichlorophenyl)-1,3,4-oxadiazol-2-yl)pyridin-2-amine and tert-butyl 4-(4-(4,4,5,5-tetramethyl-1,3,2-dioxaborolan-2-yl)-1H-pyrazol-1-yl)piperidine-1-carboxylate; 34% | $^1$H NMR (400 MHz, CDCl$_3$): δ 8.42 (d, J = 2.4 Hz, 1H), 8.12 (d, J = 2.4 Hz, 1H), 7.74 (d, J = 0.8 Hz, 1H), 7.65 (d, J = 0.8 Hz, 1H), 7.52-7.49 (m, 3H), 6.63 (br s, 2H), 4.36-4.18 (m, 3H), 2.96-2.84 (m, 2H), 2.20-2.13 (m, 2H), 2.02-1.88 (m, 2H), 1.48 (s, 9H). |
| 1.5 | tert-butyl 4-(4-(6-amino-5-(5-(4-fluorophenyl)-1,3,4-oxadiazol-2-yl)pyridin-3-yl)-1H-pyrazol-1-yl)piperidine-1-carboxylate | 5-bromo-3-(5-(4-fluorophenyl)-1,3,4-oxadiazol-2-yl)pyridin-2-amine and tert-butyl 4-(4-(4,4,5,5-tetramethyl-1,3,2-dioxaborolan-2-yl)-1H-pyrazol-1-yl)piperidine-1-carboxylate; 35% | $^1$H NMR (400 MHz, CDCl$_3$): δ 8.40 (d, J = 2.4 Hz, 1H), 8.21-8.15 (m, 2H), 8.14 (d, J = 2.4 Hz, 1H), 7.78 (d, J = 0.8 Hz, 1H), 7.67 (d, J = 0.8 Hz, 1H), 7.30-7.24 (m, 2H), 6.60 (br s, 2H), 4.39-4.23 (m, 3H), 2.98-2.87 (m, 2H), 2.24-2.16 (m, 2H), 2.04-1.83 (m, 2H), 1.48 (s, 9H). |
| 1.6 | 3-(5-(2,6-dichlorophenyl)-1,3,4-oxadiazol-2-yl)-5-(1H-pyrazol-4-yl)pyridin-2-amine | 5-bromo-3-(5-(2,6-dichlorophenyl)-1,3,4-oxadiazol-2-yl)pyridin-2-amine and pyrazole-4-boronic acid pinacol ester; 12% | $^1$H NMR (400 MHz, DMSO-d$_6$): δ 12.9 (br s, 1H), 8.58-8.55 (m, 1H), 8.24-8.21 (m, 1H), 8.20 (s, 1H), 7.92 (s, 1H), 7.79-7.71 (m, 2H), 7.32 (br s, 2H); MS (ES+): m/z 373.2, 374.2 and 375.2 (M + 1). |
| 1.7 | 3-(5-phenyl-1,3,4-oxadiazol-2-yl)-5-(1H-pyrazol-4-yl)pyridin-2-amine | pyrazole-4-boronic acid pinacol ester and 5-bromo-3-(5-phenyl-1,3,4-oxadiazol-2-yl)pyridin-2-amine; 21% | $^1$H NMR (400 MHz, DMSO-d$_6$): δ 12.9 (br s, 1H), 8.53 (d, J = 2.4 Hz, 1H), 8.40 (d, J = 2.4 Hz, 1H), 8.26-8.19 (m, 3H), 7.99 (s, 1H), 7.67-7.59 (m, 3H), 7.26 (br s, 2H); MS (ES+): m/z 305.3 (M + 1). |

-continued

| Ex. No. | Chemical Name | Starting Material and Yield | Characterization Data |
|---|---|---|---|
| 1.8 | 3-(5-(4-tert-butylphenyl)-1,3,4-oxadiazol-2-yl)-5-(1H-pyrazol-4-yl)pyridin-2-amine | 5-bromo-3-(5-(4-(tert-butyl)phenyl)-1,3,4-oxadiazol-2-yl)pyridin-2-amine and pyrazole-4-boronic acid pinacol ester; 21% | $^1$H NMR (400 MHz, DMSO-$d_6$): δ 8.52 (d, J = 2.4 Hz, 1H), 8.37 (d, J = 2.4 Hz, 1H), 8.22 (s, 1H), 8.14-8.10 (m, 2H), 7.97 (s, 1H), 7.64-7.60 (m, 2H), 7.25 (br s, 2H), 1.33 (s, 9H). MS (ES+): m/z 361.3 (M + 1). |
| 1.9 | 3-(5-(2,5-difluorophenyl)-1,3,4-oxadiazol-2-yl)-5-(1H-pyrazol-4-yl)pyridin-2-amine | 5-bromo-3-(5-(2,5-difluorophenyl)-1,3,4-oxadiazol-2-yl)-pyridin-2-amine and pyrazole-4-boronic acid pinacol ester; 20% | $^1$H NMR (400 MHz, DMSO-$d_6$): δ 8.54 (d, J = 2.4 Hz, 1H), 8.38 (d, J = 2.4 Hz, 1H), 8.20-8.13 (m, 2H), 8.09 (s, 1H), 7.59-7.53 (m, 2H) 7.28 (br s, 2H); MS (ES+): m/z 341.3 (M + 1). |
| 1.10 | 3-(5-(2,5-difluorophenyl)-1,3,4-oxadiazol-2-yl)-5-(1H-pyrazol-4-yl)pyridin-2-amine | 5-bromo-3-(5-(4-fluorophenyl)-1,3,4-oxadiazol-2-yl)-pyridin-2-amine and pyrazole-4-boronic acid pinacol ester; 26% | $^1$H NMR (400 MHz, DMSO-$d_6$): δ 8.51 (d, J = 2.4 Hz, 1H), 8.39 (d, J = 2.4 Hz, 1H), 8.30-8.24 (m, 2H), 8.21 (s, 1H), 7.97 (s, 1H), 7.49-7.42 (m, 2H), 7.24 (br s, 2H); MS (ES+): m/z 323.3 (M + 1). |
| 1.11 | 3-(5-(2,6-dichlorophenyl)-1,3,4-oxadiazol-2-yl)-5-(1-cyclohexyl-1H-pyrazol-4-yl)pyridin-2-amine | 5-bromo-3-(5-(2,6-dichlorophenyl)-1,3,4-oxadiazol-2-yl)-pyridin-2-amine and 1-cyclohexyl-4-(4,4,5,5-tetramethyl-1,3,2-dioxaborolan-2-yl)-1H-pyrazole; 38% | $^1$H NMR (400 MHz, CDCl$_3$): δ 8.40 (d, J = 2.0 Hz, 1H), 8.13 (d, J = 2.4 Hz, 1H), 7.72 (s, 1H), 7.64 (s, 1H), 7.52-7.48 (m, 3H), 6.86-6.60 (br s, 2H), 4.15-4.11 (m, 1H), 2.24-2.16 (m, 2H), 1.96-1.86 (m, 2H), 1.76-1.70 (m, 2H), 1.45-1.39 (m, 2H), 1.33-1.20 (m, 2H). MS (ES+): m/z 455.3, 456.3 and 457.3 (M + 1). |

Example 2

Synthesis of 3-(3-phenyl-1,2,4-oxadiazol-5-yl)-5-(1-(tetrahydro-2H-pyran-4-yl)-1H-pyrazol-4-yl)pyridin-2-amine

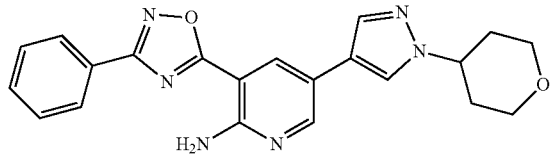 [SMILES: Nc1ncc(-c2cnn(C3CCOCC3)c2)cc1-c1nc(-c2ccccc2)no1]

A mixture of 5-bromo-3-(3-phenyl-1,2,4-oxadiazol-5-yl) pyridin-2-amine (100 mg, 0.33 mmol), 1-(tetrahydro-2H-pyran-4-yl)-4-(4,4,5,5-tetramethyl-1,3,2-dioxaborolan-2-yl)-1H-pyrazole (0.11 g, 0.40 mmol) and cesium carbonate (0.54 g, 1.65 mmol) in 5 mL of 10:1 dioxane:water in a sealed tube was degassed for 10 min, followed by the addition of tetrakis(triphenylphosphine)palladium(0) (38 mg, 0.03 mmol). The mixture was degassed for another 10 minutes and then heated at 100° C. overnight. After removal of the solvents in vacuo, the residue was purified by column chromatography eluted with ethyl acetate to afford the title compound as a yellowish solid in 20% yield (25 mg). $^1$H NMR (400 MHz, DMSO-$d_6$): δ8.48 (s, 1H), 8.35 (d, J=2.4 Hz, 1H), 8.20-8.14 (m, 2H), 7.79 (s, 1H), 7.71 (s, 1H), 7.58-7.50 (m, 3H), 6.66 (br s, 2H), 4.48-4.38 (m, 1H), 4.20-4.10 (m, 2H), 3.62-3.55 (m, 2H), 2.22-2.10 (m, 4H); MS (ES+): m/z 389.3 (M+1).

The table below shows additional examples of compounds of Formula (IA5) that were prepared according to the above process.

| Ex. No. | Chemical Name | Starting Material and Yield | Characterization Data |
|---|---|---|---|
| 2.1 | tert-butyl 4-(4-(6-amino-5-(3-phenyl-1,2,4-oxadiazol-5-yl)pyridin-3-yl)-1H-pyrazol-1-yl)piperidine-1-carboxylate | tert-butyl 4-(4-(4,4,5,5-tetramethyl-1,3,2-dioxaborolan-2-yl)-1H-pyrazol-1-yl)piperidine-1-carboxylate and 5-bromo-3-(3-phenyl-1,2,4-oxadiazol-5-yl)pyridin-2-amine; 60% | $^1$H NMR (400 MHz, CDCl$_3$): δ 8.45 (d, J = 2.4 Hz, 1H), 8.32 (d, J = 2.4 Hz, 1H), 8.17-8.12 (m, 2H), 7.78 (s, 1H), 7.68 (s, 1H), 7.56-7.50 (m, 3H), 6.68 (br s, 2H), 4.38-4.22 (m, 3H), 3.00-2.84 (m, 2H), 2.24-2.14 (m, 2H), 2.06-1.92 (m, 2H), 1.49 (s, 9H). |
| 2.2 | tert-butyl 4-(4-(6-amino-5-(5-(pyridin-2-yl)-1,3,4-oxadiazol-2-yl)pyridin-3-yl)-1H-pyrazol-1-yl)piperidine-1-carboxylate | tert-butyl 4-(4-(4,4,5,5-tetramethyl-1,3,2-dioxaborolan-2-yl)-1H-pyrazol-1-yl)piperidine-1-carboxylate and 5-bromo-3-(5-(pyridin-2-yl)-1,3,4-oxadiazol-2-yl)pyridin-2-amine; 46% | $^1$H NMR (400 MHz, CDCl$_3$): δ 8.83 (d, J = 4.8 Hz, 1H), 8.39 (d, J = 2.4 Hz, 1H), 8.34 (d, J = 8.0 Hz, 1H), 8.31 (d, J = 2.4 Hz, 1H), 7.96-7.90 (m, 1H), 7.77 (s, 1H), 7.70 (s, 1H), 7.54-7.48 (m, 1H), 6.85-6.65 (br s, 2H), 4.38-4.20 (m, 3H), 3.00-2.85 (m, 2H), 2.22-2.14 (m, 2H), 2.04-1.90 (m, 2H), 1.49 (s, 9H). |
| 2.3 | tert-butyl 4-(4-(6-amino-5-(5-(pyridin-3-yl)-1,3,4-oxadiazol-2-yl)pyridin-3-yl)-1H-pyrazol-1- | tert-butyl 4-(4-(4,4,5,5-tetramethyl-1,3,2-dioxaborolan-2-yl)-1H-pyrazol-1-yl)piperidine-1-carboxylate and 5-bromo-3- | $^1$H NMR (400 MHz, CDCl$_3$): δ 9.36 (s, 1H), 8.81 (dd, J = 4.8, 1.2 Hz, 1H), 8.43 (dt, J = 8.0, 2.0 Hz, 1H), 8.39 (d, J = 2.4 Hz, 1H), 8.13 (d, J = 2.4 Hz, 1H), 8.07 (s, 1H), 7.76 (s, |

| Ex. No. | Chemical Name | Starting Material and Yield | Characterization Data |
|---|---|---|---|
| | yl)piperidine-1-carboxylate | (5-(pyridin-3-yl)-1,3,4-oxadiazol-2-yl)pyridin-2-amine; 34% | 1H), 7.67 (s, 1H), 6.75-6.60 (br s, 2H), 4.38-4.20 (m, 3H), 3.00-2.85 (m, 2H), 2.22-2.14 (m, 2H), 2.04-1.90 (m, 2H), 1.47 (s, 9H). |
| 2.4 | tert-butyl 4-(4-(6-amino-5-(5-(pyrazin-2-yl)-1,3,4-oxadiazol-2-yl)pyridin-3-yl)-1H-pyrazol-1-yl)piperidine-1-carboxylate | tert-butyl 4-(4-(4,4,5,5-tetramethyl-1,3,2-dioxaborolan-2-yl)-1H-pyrazol-1-yl)piperidine-1-carboxylate and 5-bromo-3-(5-(pyrazin-2-yl)-1,3,4-oxadiazol-2-yl)pyridin-2-amine; 62% | $^1$H NMR (400 MHz, CDCl$_3$): δ 9.57 (s, 1H), 8.80 (s, 2H), 8.42 (s, 1H), 8.28 (s, 1H), 7.78 (s, 1H), 7.69 (s, 1H), 6.85-6.65 (br s, 2H), 4.38-4.20 (m, 3H), 3.00-2.85 (m, 2H), 2.22-2.14 (m, 2H), 2.04-1.90 (m, 2H), 1.49 (s, 9H). |
| 2.5 | tert-butyl 4-(4-(6-amino-5-(5-(cyclopropylmethyl)-1,3,4-oxadiazol-2-yl)pyridin-3-yl)-1H-pyrazol-1-yl)piperidine-1-carboxylate | tert-butyl 4-(4-(4,4,5,5-tetramethyl-1,3,2-dioxaborolan-2-yl)-1H-pyrazol-1-yl)piperidine-1-carboxylate and 5-bromo-3-(5-(cyclopropylmethyl)-1,3,4-oxadiazol-2-yl)pyridin-2-amine; 46% | $^1$H NMR (400 MHz, CDCl$_3$): δ 8.35 (d, J = 2.4 Hz, 1H), 8.05 (d, J = 2.4 Hz, 1H), 7.74 (s, 1H), 7.64 (s, 1H), 6.70-6.55 (br s, 2H), 4.38-4.20 (m, 3H), 3.00-2.86 (m, 2H), 2.86 (d, J = 6.4 Hz, 2H), 2.22-2.14 (m, 2H), 2.04-1.90 (m, 2H), 1.48 (s, 9H), 1.28-1.18 (m, 1H), 0.70-0.58 (m, 2H), 0.38-0.28 (m, 2H). |
| 2.6 | tert-butyl 4-(4-(6-amino-5-(5-benzyl-1,3,4-oxadiazol-2-yl)pyridin-3-yl)-1H-pyrazol-1-yl)piperidine-1-carboxylate | tert-butyl 4-(4-(4,4,5,5-tetramethyl-1,3,2-dioxaborolan-2-yl)-1H-pyrazol-1-yl)piperidine-1-carboxylate and 3-(5-benzyl-1,3,4-oxadiazol-2-yl)-5-bromopyridin-2-amine; 36% | $^1$H NMR (400 MHz, CDCl$_3$): δ 8.34 (d, J = 2.4 Hz, 1H), 7.99 (d, J = 2.4 Hz, 1H), 7.72 (s, 1H), 7.62 (s, 1H), 7.41-7.29 (m, 5H), 6.70-6.50 (br s, 2H), 4.38-4.20 (m, 5H), 3.00-2.85 (m, 2H), 2.22-2.14 (m, 2H), 2.04-1.90 (m, 2H), 1.49 (s, 9H). |
| 2.7 | tert-butyl 4-(4-(6-amino-5-(5-(thiazol-2-yl)-1,3,4-oxadiazol-2-yl)pyridin-3-yl)-1H-pyrazol-1-yl)piperidine-1-carboxylate | tert-butyl 4-(4-(4,4,5,5-tetramethyl-1,3,2-dioxaborolan-2-yl)-1H-pyrazol-1-yl)piperidine-1-carboxylate and 5-bromo-3-(5-(thiazol-2-yl)-1,3,4-oxadiazol-2-yl)pyridin-2-amine; 62% | $^1$H NMR (400 MHz, CDCl$_3$): δ 8.41 (d, J = 2.4 Hz, 1H), 8.28 (d, J = 2.4 Hz, 1H), 8.13 (d, J = 2.4 Hz, 1H), 7.77 (s, 1H), 7.71-7.68 (m, 2H), 6.85-6.65 (br s, 2H), 4.38-4.20 (m, 3H), 3.00-2.86 (m, 2H), 2.22-2.14 (m, 2H), 2.04-1.90 (m, 2H), 1.48 (s, 9H). |
| 2.8 | tert-butyl 4-(4-(6-amino-5-(5-(4-(trifluoromethyl)thiazol-2-yl)-1,3,4-oxadiazol-2-yl)pyridin-3-yl)-1H-pyrazol-1-yl)piperidine-1-carboxylate | tert-butyl 4-(4-(4,4,5,5-tetramethyl-1,3,2-dioxaborolan-2-yl)-1H-pyrazol-1-yl)piperidine-1-carboxylate and 5-bromo-3-(5-(4-(trifluoromethyl)thiazol-2-yl)-1,3,4-oxadiazol-2-yl)pyridin-2-amine; 36% | $^1$H NMR (400 MHz, CDCl$_3$): δ 8.43 (d, J = 2.4 Hz, 1H), 8.28 (d, J = 2.4 Hz, 1H), 8.07 (s, 1H), 7.79 (s, 1H), 7.73 (s, 1H), 6.70-6.55 (br s, 2H), 4.38-4.20 (m, 3H), 3.00-2.84 (m, 2H), 2.24-2.16 (m, 2H), 2.05-1.93 (m, 2H), 1.48 (s, 9H). |
| 2.9 | 3-(5-phenyl-1,2,4-oxadiazol-3-yl)-5-(1H-pyrazol-4-yl)pyridin-2-amine | 4-(4,4,5,5-tetramethyl-1,3,2-dioxaborolan-2-yl)-1H-pyrazole and 5-bromo-3-(5-phenyl-1,2,4-oxadiazol-3-yl)pyridin-2-amine; 5% | $^1$H NMR (400 MHz, CD$_3$OD): δ 8.60 (d, J = 2.4 Hz, 1H), 8.38 (d, J = 2.4 Hz, 1H), 8.27-8.22 (m, 2H), 7.96 (br s, 2H), 7.71-7.65 (m, 1H), 7.64-7.59 (m, 2H); MS (ES+): m/z 305.3 (M + 1). |
| 2.10 | 3-(3-phenyl-1,2,4-oxadiazol-5-yl)-5-(1H-pyrazol-4-yl)pyridin-2-amine | 4-(4,4,5,5-tetramethyl-1,3,2-dioxaborolan-2-yl)-1H-pyrazole and 5-bromo-3-(3-phenyl-1,2,4-oxadiazol-5-yl)pyridin-2-amine; 5% | $^1$H NMR (400 MHz, 15% CD$_3$OD in CDCl$_3$): δ 8.42 (d, J = 2.0 Hz, 1H), 8.35 (d, J = 2.4 Hz, 1H), 8.15-8.09 (m, 2H), 7.81 (s, 2H), 7.54-7.46 (m, 3H). MS (ES+): m/z 305.3 (M + H). |
| 2.11 | tert-butyl 4-(4-(6-amino-5-(5-cyclohexyl-1,3,4-oxadiazol-2-yl)pyridin-3-yl)-1H-pyrazol-1-yl)piperidine-1-carboxylate | tert-butyl 4-(4-(4,4,5,5-tetramethyl-1,3,2-dioxaborolan-2-yl)-1H-pyrazol-1-yl)piperidine-1-carboxylate and 5-bromo-3-(5-cyclohexyl-1,3,4-oxadiazol-2-yl)pyridin-2-amine; 33% | $^1$H NMR (400 MHz, CDCl$_3$): δ 8.35 (d, J = 2.0 Hz, 1H), 8.03 (d, J = 2.0 Hz, 1H), 7.75 (s, 1H), 7.65 (s, 1H), 6.59 (br s, 2H), 4.38-4.34 (m, 3H),' 3.05-2.97 (m, 1H), 2.97-2.85 (m, 2H), 2.23-2.12 (m, 4H), 2.05-1.98 (m, 2H), 1.95-1.86 (m, 2H), 1.81-1.63 (m, 4H), 1.49 (s, 9H), 1.46-1.38 (m, 2H). |
| 2.12 | 5-(1-cyclohexyl-1H-pyrazol-4-yl)-3-(3-phenyl-1,2,4-oxadiazol-5-yl)pyridin-2-amine | 5-bromo-3-(3-phenyl-1,2,4-oxadiazol-5-yl)pyridin-2-amine and 1-cyclohexyl-4-(4,4,5,5-tetramethyl-1,3,2-dioxaborolan-2-yl)-1H-pyrazole; 15% | $^1$H NMR (400 MHz, CDCl$_3$): δ 8.47 (d, J = 2.4 Hz, 1H), 8.34 (d, J = 2.4 Hz, 1H), 8.19-1.14 (m, 2H), 7.78 (s, 1H), 7.69 (s, 1H), 7.57-7.51 (m, 3H), 6.65 (br s, 2H), 4.23-4.13 (m, 1H), 2.28-2.20 (m, 2H), 1.98-1.91 (m,' 2H), 1.85-1.74 (m, 3H), 1.54-1.40 (m, 2H), 1.37-1.29 (m, 1H); MS (ES+) m/z 387.4 (M + 1). |

| Ex. No. | Chemical Name | Starting Material and Yield | Characterization Data |
| --- | --- | --- | --- |
| 2.13 | 3-(5-(2,6-dichlorophenyl)-1,3,4-oxadiazol-2-yl)-5-(1-(tetrahydro-2H-pyran-4-yl)-1H-pyrazol-4-yl)pyridin-2-amine | 5-bromo-3-(5-(2,6-dichlorophenyl)-1,3,4-oxadiazol-2-yl)pyridin-2-amine and 1-(tetrahydro-2H-pyran-4-yl)-4-(4,4,5,5-tetramethyl-1,3,2-dioxaborolan-2-yl)-1H-pyrazole; 35% | $^1$H NMR (400 MHz, CDCl$_3$): δ 8.44 (d, J = 2.4 Hz, 1H), 8.12 (d, J = 2.4 Hz, 1H), 7.74 (s, 1H), 7.66 (s, 1H), 7.52-7.49 (m, 3H), 6.70-6.55 (br s, 2H), 4.42-4.36 (m, 1H), 4.16-4.10 (m, 2H), 3.60-3.50 (m, 2H), 2.16-2.06 (m, 4H). MS (ES+): m/z 457.2 and 459.2 (M + 1). |
| 2.14 | 5-(1-(tetrahydro-2H-pyran-4-yl)-1H-pyrazol-4-yl)-3-(5-phenyl-1,3,4-oxadiazol-2-yl)pyridin-2-amine | 1-(tetrahydro-2H-pyran-4-yl)-4-(4,4,5,5-tetramethyl-1,3,2-dioxaborolan-2-yl)-1H-pyrazole and 5-bromo-3-(5-phenyl-1,3,4-oxadiazol-2-yl)pyridin-2-amine; 50% | $^1$H NMR (400 MHz, CDCl$_3$): δ 8.41 (d, J = 2.4 Hz, 1H), 8.20-8.14 (m, 3H), 7.79 (s, 1H), 7.70 (s, 1H), 7.63-7.54 (m, 3H), 6.75-6.50 (br s, 2H), 4.47-4.38 (m, 1H), 4.19-4.14 (m, 2H), 3.63-3.54 (m, 2H), 2.23-2.10 (m, 4H). MS (ES+): m/z 389.4 (M + 1), 411.4 (M + Na). |
| 2.15 | 5-(1-cyclohexyl-1H-pyrazol-4-yl)-3-(5-phenyl-1,3,4-oxadiazol-2-yl)pyridin-2-amine | 1-cyclohexyl-4-(4,4,5,5-tetramethyl-1,3,2-dioxaborolan-2-yl)-1H-pyrazole and 5-bromo-3-(5-phenyl-1,3,4-oxadiazol-2-yl)pyridin-2-amine; 8% | $^1$H NMR (400 MHz, CDCl$_3$): δ 8.40 (d, J = 2.4 Hz, 1H), 8.20-8.14 (m, 3H), 7.76 (s, 1H), 7.68 (s, 1H), 7.63-7.54 (m, 3H), 6.70-6.50 (br s, 2H), 4.20-4.13 (m, 1H), 2.38-2.30 (m, 2H), 2.00-1.90 (m, 2H), 1.85-1.75 (m, 3H), 1.54-1.40 (m, 2H), 1.37-1.25 (m, 1H). MS (ES+): m/z 387.4 (M + 1), 409.4 (M + Na). |
| 2.16 | tert-butyl 4-(4-(6-amino-5-(3-(2,6-dichlorophenyl)-1,2,4-oxadiazol-5-yl)pyridin-3-yl)-1H-pyrazol-1-yl)piperidine-1-carboxylate | 5-bromo-3-(3-(2,6-dichlorophenyl)-1,2,4-oxadiazol-5-yl)pyridin-2- and tert-butyl 4-(4-(4,4,5,5-tetramethyl-1,3,2-dioxaborolan-2-yl)-1H-pyrazol-1-yl)piperidine-1-carboxylate; 20% | $^1$H NMR (400 MHz, CDCl$_3$): δ 8.46 (m, 1H), 8.37 (m, 1H), 7.78 (m, 1H), 7.69 (s, 1H), 7.50-7.40 (m, 3H), 6.70-6.50 (br s, 2H), 4.37-4.14 (m, 3H), 3.00-2.82 (m, 2H), 2.22-2.10 (m, 2H), 2.07-1.88 (m, 2H), 1.48 (s, 9H). |
| 2.17 | 3-(3-(2,6-dichlorophenyl)-1,2,4-oxadiazol-5-yl)-5-(1-(tetrahydro-2H-pyran-4-yl)-1H-pyrazol-4-yl)pyridin-2-amine | 5-bromo-3-(3-(2,6-dichlorophenyl)-1,2,4-oxadiazol-5-yl)pyridin-2-amine and 1-(tetrahydro-2H-pyran-4-yl)-4-(4,4,5,5-tetramethyl-1,3,2-dioxaborolan-2-yl)-1H-pyrazole; 6% | $^1$H NMR (400 MHz, CDCl$_3$): δ 8.48 (d, J = 2.0 Hz, 1H), 8.38 (d, J = 2.4 Hz, 1H), 7.79 (s, 1H), 7.71 (s, 1H), 7.50-7.41 (m, 3H), 6.54 (br s, 2H), 4.48-4.37 (m, 1H), 4.19-4.13 (m, 2H), 3.62-3.55 (m, 2H), 2.22-2.12 (m, 4H); MS (ES+): m/z 457.2, 458.2 and 459.2 (M + 1). |
| 2.18 | 3-(3-(2,6-dichlorophenyl)-1,2,4-oxadiazol-5-yl)-5-(1-cyclohexyl-1H-pyrazol-4-yl)pyridin-2-amine | 5-bromo-3-(3-(2,6-dichlorophenyl)-1,2,4-oxadiazol-5-yl)pyridin-2-amine and 1-cyclohexyl-4-(4,4,5,5-tetramethyl-1,3,2-dioxaborolan-2-yl)-1H-pyrazole; 20% | $^1$H NMR (400 MHz, CDCl$_3$): δ 8.48 (d, J = 2.4 Hz, 1H), 8.38 (d, J = 2.4 Hz, 1H), 7.77 (s, 1H), 7.69 (s, 1H), 7.49-7.41 (m, 3H), 6.54 (br s, 2H), 4.22-4.13 (m, 1H), 2.28-2.22 (m, 2H), 1.96-1.93 (m, 2H), 1.81-1.75 (m, 3H), 1.53-1.49 (m, 2H), 1.48-1.46 (m, 1H); MS (ES+): m/z 455.3, 456.3 and 457.3 (M + 1). |
| 2.19 | tert-butyl 4-(3-(6-amino-5-(5-(2,6-dichlorophenyl)-1,3,4-oxadiazol-2-yl)pyridin-3-yl)-1H-pyrrol-1-yl)piperidine-1-carboxylate | 5-bromo-3-(5-(2,6-dichlorophenyl)-1,3,4-oxadiazol-2-yl)pyridin-2-amine and tert-butyl 4-(3-(4,4,5,5-tetramethyl-1,3,2-dioxaborolan-2-yl)-1H-pyrrol-1-yl)piperidine-1-carboxylate; 46% | $^1$H NMR (400 MHz, CDCl$_3$): δ 8.45 (d, J = 2.4 Hz, 1H), 8.13 (J = 2.4 Hz, 1H), 7.53-7.48 (m, 3H), 6.99-6.97 (m, 1H), 6.78-6.75 (m, 1H), 6.55 (br s, 2H), 6.43-6.40 (m, 1H), 4.35-4.22 (m, 2H), 4.02-3.92 (m, 1H), 2.80-2.78 (m, 2H), 2.12-2.05 (m, 2H), 1.92-1.80 (m, 2H), 1.48 (s, 9H). |

Example 3

Synthesis of chloro-3-fluorophenyl)-1,3,4-oxadiazol-2-yl)-5-(1-piperidin-4-yl)-1H-pyrazol-4-yl)pyridin-2-amine

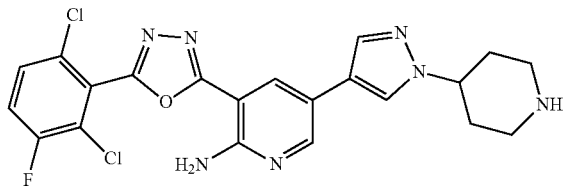 [SMILES: Nc1ncc(-c2cnn(C3CCNCC3)c2)cc1-c1nnc(-c2c(Cl)ccc(F)c2Cl)o1]

To a solution of tert-butyl 4-(4-(6-amino-5-(5-(2,6-dichloro-3-fluorophenyl)-1,3,4-oxadiazol-2-yl)pyridin-3-yl)-1H-pyrazol-1-yl)piperidine-1-carboxylate (30.0 mg, 0.052 mmol) in dichloromethane (3 mL) was added a solution of 2 N hydrochloric acid in diethyl ether (1.00 mL, 2.00 mmol). The mixture was stirred at ambient temperature overnight, diluted with saturated sodium bicarbonate (5 mL), and extracted with dichloromethane (3×20 mL). The combined extracts were washed with brine (10 mL), dried and evaporated to afford the title compound as a pale brown solid in 92% yield (23 mg). $^1$H NMR (400 Hz, CDCl$_3$): δ 8.43 (d, J=2.4 Hz, 1H), 8.11 (d, J=2.4 Hz, 1H), 7.74 (d, J=0.8 Hz, 1H), 7.66 (d, J=0.8 Hz, 1H), 7.53-7.48 (m, 1H), 7.41-7.36 (m, 1H), 6.61 (br s, 2H), 4.30-4.21 (m, 1H), 3.30-3.23 (m, 2H), 2.83-2.75 (m, 2H), 2.23-2.17 (m, 2H), 1.98-1.87 (m, 2H); MS (ES+): m/z 474.2, 475.2 and 476.3 (M+1).

The table below shows additional examples of compounds of Formula (IA4) that were prepared according to the above process.

| Ex. No. | Chemical Name | Starting Material and Yield | Characterization Data |
|---|---|---|---|
| 3.1 | 3-(5-phenyl-1,3,4-oxadiazol-2-yl)-5-(1-(piperidin-4-yl)-1H-pyrazol-4-yl)pyridin-2-amine | tert-butyl 4-(4-(6-amino-5-(5-phenyl-1,3,4-oxadiazol-2-yl)pyridin-3-yl)-1H-pyrazol-1-yl)piperidine-1-carboxylate; 76% | $^1$H NMR (400 MHz, CDCl$_3$): δ 8.40 (d, J = 2.4 Hz, 1H), 8.19-8.15 (m, 3H), 7.77 (d, J = 0.8 Hz, 1H), 7.70 (d, J = 0.8 Hz, 1H), 7.61-7.55 (m, 3H), 6.59 (br s, 2H), 4.34-4.25 (m, 1H), 3.32-3.25 (m, 2H), 2.85-2.77 (m, 2H), 2.26-2.19 (m, 2H), 2.03-1.91 (m, 2H); MS (ES+): m/z 388.3 (M + 1). |
| 3.2 | 3-(5-(4-(tert-butyl)phenyl)-1,3,4-oxadiazol-2-yl)-5-(1-(piperidin-4-yl)-1H-pyrazol-4-yl)pyridin-2-amine | tert-butyl 4-(4-(5-(5-(4-tert-butylphenyl)-1,3,4-oxadiazol-2-yl)-6-aminopyridin-3-yl)-1H-pyrazol-1-yl)piperidine-1-carboxylate; 100% | $^1$H NMR (300 Hz, CDCl$_3$): δ 8.39 (d, J = 2.4 Hz, 1H), 8.16 (d, J = 2.4 Hz, 1H), 8.11-8.06 (m, 2H), 7.77 (s, 1H), 7.70 (s, 1H), 7.61-7.56 (m, 2H), 6.60 (br s, 2H), 4.35-4.27 (m, 1H), 3.36-3.28 (m, 2H), 2.88-2.78 (m, 2H), 2.28-2.23 (m, 2H), 2.07-1.95 (m, 2H), 1.38 (s, 9H); MS (ES+): m/z 444.4 (M + 1). |
| 3.3 | 3-(5-(2,5-difluorophenyl)-1,3,4-oxadiazol-2-yl)-5-(1-piperidin-4-yl)-1H-pyrazol-4-yl)pyridin-2-amine | tert-butyl 4-(4-(6-amino-5-(5-(2,5-difluorophenyl)-1,3,4-oxadiazol-2-yl)pyridin-3-yl)-1H-pyrazol-1-yl)piperidine-1-carboxylate; 88% | $^1$H NMR (300 Hz, CDCl$_3$) δ 8.42 (d, J = 2.4 Hz, 1H), 8.16 (d, J = 2.4 Hz, 1H), 7.90-7.84 (m, 1H), 7.76 (s, 1H), 7.68 (s, 1H), 7.30-7.26 (m, 2H), 6.58 (br s, 2H), 4.33-4.24 (m, 1H), 3.31-3.24 (m, 2H), 2.85-2.75 (m, 2H), 2.26-2.17 (m, 2H), 2.02-1.90 (m, 2H); MS (ES+): m/z 424.3 (M + 1). |
| 3.4 | 3-(5-(2,6-dichlorophenyl)-1,3,4-oxadiazol-2-yl)-5-(1-piperidin-4-yl)-1H-pyrazol-4-yl)pyridin-2-amine | tert-butyl 4-(4-(6-amino-5-(5-(2,6-dichlorophenyl)-1,3,4-oxadiazol-2-yl)pyridin-3-yl)-1H-pyrazol-1-yl)piperidine-1-carboxylate; 90% | $^1$H NMR (300 Hz, CDCl$_3$) δ 8.42 (d, J = 2.4 Hz, 1H), 8.12 (d, J = 2.4 Hz, 1H), 7.73 (s, 1H), 7.66 (s, 1H), 7.54-7.47 (m, 3H), 6.62 (br s, 2H), 4.31-4.20 (m, 1H), 3.31-3.22 (m, 2H), 2.84-2.73 (m, 2H), 2.24-2.16 (m, 2H), 1.98-1.76 (m, 2H); MS (ES+): m/z 456.2, 457.3 and 458.3 (M + 1). |
| 3.5 | 3-(5-(4-fluorophenyl)-1,3,4-oxadiazol-2-yl)-5-(1-piperidin-4-yl)-1H-pyrazol-4-yl)pyridin-2-amine | tert-butyl 4-(4-(6-amino-5-(5-(4-fluorophenyl)-1,3,4-oxadiazol-2-yl)pyridin-3-yl)-1H-pyrazol-1-yl)piperidine-1-carboxylate; 87% | $^1$H NMR (300 Hz, CDCl$_3$): δ 8.40 (d, J = 2.4 Hz, 1H), 8.21-8.15 (m, 2H), 8.14 (d, J = 2.4 Hz, 1H), 7.77 (d, J = 0.8 Hz, 1H), 7.70 (d, J = 0.8 Hz, 1H), 7.30-7.24 (m, 2H), 6.60 (br s, 2H), 4.33-4.25 (m, 1H), 3.32-3.25 (m, 2H), 2.85-2.76 (m, 2H), 2.26-2.18 (m, 2H), 2.02-1.90 (m, 2H); MS (ES+): m/z 406.4 (M + 1). |
| 3.6 | 3-(3-phenyl-1,2,4-oxadiazol-5-yl)-5-(1-(piperidin-4-yl)-1H-pyrazol-4-yl)pyridin-2-amine | tert-butyl 4-(4-(6-amino-5-(3-phenyl-1,2,4-oxadiazol-5-yl)pyridin-3-yl)-1H-pyrazol-1-yl)-piperidine-1-carboxylate; 77% | $^1$H NMR (400 MHz, CDCl$_3$): δ 8.46 (d, J = 2.4 Hz, 1H), 8.34 (d, J = 2.4 Hz, 1H), 8.18-8.12 (m, 2H), 7.77 (s, 1H), 7.70 (s, 1H), 7.58-7.50 (m, 3H), 6.66 (br s, 2H), 4.32-4.22 (m, 1H), 3.32-3.22 (m, 2H), 2.85-2.74 (m, 2H), 2.26-2.17 (m, 2H), 2.00-1.88 (m, 2H); MS (ES+): m/z 388.4 (M + 1). |
| 3.7 | 3-(5-(cyclopropylmethyl)-1,3,4-oxadiazol-2-yl)-5-(1-(piperidin-4-yl)-1H-pyrazol-4-yl)pyridin-2-amine | tert-butyl 4-(4-(6-amino-5-(5-(cyclopropylmethyl)-1,3,4-oxadiazol-2-yl)pyridin-3-yl)-1H-pyrazol-1-yl)piperidine-1-carboxylate; 77% | $^1$H NMR (400 MHz, CD$_3$OD): δ 8.36 (d, J = 2.4 Hz, 1H), 8.20 (d, J = 2.4 Hz, 1H), 8.06 (s, 1H), 7.82 (s, 1H), 4.45-4.35 (m, 1H), 3.38-3.30 (m, 2H), 2.98-2.88 (m, 2H), 2.87 (d, J = 8.0 Hz, 2H), 2.24-2.16 (m, 2H), 2.14-2.02 |

| Ex. No. | Chemical Name | Starting Material and Yield | Characterization Data |
| --- | --- | --- | --- |
| | | | (m, 2H), 1.28-1.17 (m, 1H), 0.67-0.61 (m, 2H), 0.38-0.32 (m, 2H); MS (ES+): m/z 366.4 (M + 1). |
| 3.8 | 5-(1-(piperidin-4-yl)-1H-pyrazol-4-yl)-3-(5-(pyridin-2-yl)-1,3,4-oxadiazol-2-yl)pyridin-2-amine | tert-butyl 4-(4-(6-amino-5-(5-(pyridin-2-yl)-1,3,4-oxadiazol-2-yl)pyridin-3-yl)-1H-pyrazol-1-yl)piperidine-1-carboxylate; 61% | $^1$H NMR (400 MHz, CD$_3$OD): δ 8.79 (d, J = 4.4 Hz, 1H), 8.73 (d, J = 2.4 Hz, 1H), 8.42 (d, J = 2.4 Hz, 1H), 8.38 (d, J = 12.0 Hz, 1H), 8.19 (s, 1H), 8.13-8.06 (m, 1H), 7.97 (s, 1H), 7.69-7.64 (m, 1H), 4.65-4.56 (m, 1H), 3.63-3.55 (m, 2H), 3.30-3.20 (m, 2H), 2.42-2.26 (m, 4H); MS (ES+): m/z 389.3 (M + 1). |
| 3.9 | 5-(1-(piperidin-4-yl)-1H-pyrazol-4-yl)-3-(5-(pyridin-3-yl)-1,3,4-oxadiazol-2-yl)pyridin-2-amine | tert-butyl 4-(4-(6-amino-5-(5-(pyridin-3-yl)-1,3,4-oxadiazol-2-yl)pyridin-3-yl)-1H-pyrazol-1-yl)piperidine-1-carboxylate; 68% | $^1$H NMR (400 MHz, CD$_3$OD): δ 9.36 (d, J = 1.6 Hz, 1H), 8.81-8.76 (m, 1H), 8.65-8.60 (m, 1H), 8.46 (d, J = 2.4 Hz, 1H), 8.40 (d, J = 2.4 Hz, 1H), 8.17 (d, J = 0.4 Hz, 1H), 7.96 (d, J = 0.8 Hz, 1H), 7.70-7.75 (m, 1H), 4.62-4.53 (m, 1H), 3.50-3.42 (m, 2H), 3.26-3.17 (m, 2H), 2.40-2.24 (m, 4H); MS (ES+): m/z 389.4 (M + 1). |
| 3.10 | 5-(1-(piperidin-4-yl)-1H-pyrazol-4-yl)-3-(5-(pyrazin-2-yl)-1,3,4-oxadiazol-2-yl)pyridin-2-amine | tert-butyl 4-(4-(6-amino-5-(5-(pyrazin-2-yl)-1,3,4-oxadiazol-2-yl)pyridin-3-yl)-1H-pyrazol-1-yl)piperidine-1-carboxylate; 100% | $^1$H NMR (400 MHz, CD$_3$OD): δ 9.54 (d, J = 1.6 Hz, 1H), 8.87-8.82 (m, 2H), 8.80 (d, J = 2.4 Hz, 1H), 8.45 (d, J = 2.4 Hz, 1H), 8.28 (d, J = 0.40 Hz, 1H), 7.99 (d, J = 0.80 Hz, 1H), 4.66-4.57 (m, 1H), 3.62-3.54 (m, 2H), 3.30-3.20 (m, 2H), 2.42-2.26 (m, 4H); MS (ES+): m/z 390.4 (M + 1). |
| 3.11 | 3-(5-benzyl-1,3,4-oxadiazol-2-yl)-5-(1-(piperidin-4-yl)-1H-pyrazol-4-yl)pyridin-2-amine | tert-butyl 4-(4-(6-amino-5-(5-benzyl-1,3,4-oxadiazol-2-yl)pyridin-3-yl)-1H-pyrazol-1-yl)piperidine-1-carboxylate; 57% | $^1$H NMR (400 MHz, CD$_3$OD): δ 8.34 (d, J = 2.4 Hz, 1H), 8.14 (d, J = 2.4 Hz, 1H), 8.05 (d, J = 0.80 Hz, 1H), 7.82 (d, J = 0.80 Hz, 1H), 7.39-7.25 (m, 5H), 4.56-4.46 (m, 1H), 4.33 (s, 2H), 3.54-3.46 (m, 2H), 3.19-3.10 (m, 2H), 2.34-2.16 (m, 4H); MS (ES+): m/z 402.4 (M + 1). |
| 3.12 | 5-(1-(piperidin-4-yl)-1H-pyrazol-4-yl)-3-(5-(thiazol-2-yl)-1,3,4-oxadiazol-2-yl)pyridin-2-amine | tert-butyl 4-(4-(6-amino-5-(5-(thiazol-2-yl)-1,3,4-oxadiazol-2-yl)pyridin-3-yl)-1H-pyrazol-1-yl)piperidine-1-carboxylate; 80% | $^1$H NMR (400 MHz, CD$_3$OD): δ 8.80 (d, J = 2.0 Hz, 1H), 8.45 (d, J = 2.0 Hz, 1H), 8.28 (s, 1H), 8.18 (d, J = 2.8 Hz, 1H), 8.05 (d, J = 3.2 Hz, 1H), 7.99 (s, 1H), 4.65-4.57 (m, 1H), 3.62-3.54 (m, 2H), 3.30-3.20 (m, 2H), 2.42-2.25 (m, 4H); MS (ES+): m/z 395.3 (M + 1). |
| 3.13 | 5-(1-(piperidin-4-yl)-1H-pyrazol-4-yl)-3-(5-(4-(trifluoromethyl)thiazol-2-yl)-1,3,4-oxadiazol-2-yl)pyridin-2-amine | tert-butyl 4-(4-(6-amino-5-(5-(4-(trifluoromethyl)thiazol-2-yl)-1,3,4-oxadiazol-2-yl)pyridin-3-yl)-1H-pyrazol-1-yl)piperidine-1-carboxylate; 96% | $^1$H NMR (400 MHz, CD$_3$OD): δ 8.71 (d, J = 2.0 Hz, 1H), 8.61 (s, 1H), 8.47 (d, J = 2.0 Hz, 1H), 8.26 (s, 1H), 7.98 (s, 1H), 4.65-4.55 (m, 1H), 3.51-3.42 (m, 2H), 3.28-3.18 (m, 2H), 2.40-2.24 (m, 4H). MS (ES+): m/z 463.3 (M + 1). |
| 3.14 | 3-(5-cyclohexyl-1,3,4-oxadiazol-2-yl)-5-(1-(piperidin-4-yl)-1H-pyrazol-4-yl)pyridin-2-amine | tert-butyl 4-(4-(6-amino-5-(5-cyclohexyl-1,3,4-oxadiazol-2-yl)pyridin-3-yl)-1H-pyrazol-1-yl)piperidine-1-carboxylate; 95% | $^1$H NMR (400 MHz, DMSO-d$_6$): δ 8.45 (d, J = 2.4 Hz, 1H), 8.22 (s, 1H), 8.12 (d, J = 2.4 Hz, 1H), 7.87 (s, 1H), 7.19 (br s, 2H), 4.28-4.19 (m, 1H), 3.15-3.08 (m, 2H), 3.05-2.95 (m, 1H), 2.75-2.65 (m, 2H), 2.13-1.97 (m, 4H), 1.95-1.80 (m, 2H), 1.80-1.70 (m, 2H), 1.68-1.53 (m, 3H), 1.45-1.32 (m, 2H), 1.32-1.24 (m, 1H); (ES+): m/z 394.4 (M + 1). |
| 3.15 | 3-(3-(2,6-dichlorophenyl)-1,2,4-oxadiazol-5-yl)-5-(1-(piperidin-4-yl)-1H-pyrazol-4-yl)pyridin-2-amine | tert-butyl 4-(4-(6-amino-5-(3-(2,6-dichlorophenyl)-1,2,4-oxadiazol-5-yl)pyridin-3-yl)-1H-pyrazol-1-yl)piperidine-1-carboxylate; 98% | $^1$H NMR (400 M Hz, CD$_3$OD): δ 8.49 (d, J = 2.4 Hz, 1H), 8.47 (d, J = 2.4 Hz, 1H), 8.11 (s, 1H), 7.86 (s, 1H), 7.60-7.52 (m, 3H), 4.37-4.27 (m, 1H), 3.24-3.16 (m, 2H), 2.82-2.73 (m, 2H), 2.17-2.09 (m, 2H), 2.03-1.91 (m, 2H). MS (ES+): m/z 457.3. 458.3 and 459.3 (M + 1). |
| 3.16 | 3-(5-(2,6-dichlorophenyl)-1,3,4-oxadiazol-2-yl)-5-(1-(piperidin-4-yl)-1H-pyrrol-3-yl)pyridin-2-amine | tert-butyl 4-(3-(6-amino-5-(5-(2,6-dichlorophenyl)-1,3,4-oxadiazol-2-yl)pyridin-3-yl)-1H-pyrrol-1-yl)piperidine-1-carboxylate; 69% | $^1$H NMR (400 MHz, CDCl$_3$): δ 8.45 (d, J = 2.4 Hz, 1H), 8.13 (d, J = 2.4 Hz, 1H), 7.53-7.46 (m, 3H), 7.01-6.98 (m, 1H), 6.79-6.76 (m, 1H), 6.52 (br s, 2H), 6.41-6.38 (m, 1H), 3.95-3.87 (m, 1H), 3.26-3.20 (m, 2H), 2.78-2.70 (m, 2H), 2.13-2.06 (m, 2H), 1.92-1.82 (m, |

| Ex. No. | Chemical Name | Starting Material and Yield | Characterization Data |
|---|---|---|---|
| | | | 2H); MS (ES+): m/z 455.1, 456.1 and 457.1 (M + 1). |

Example 4

Synthesis of 1-(4-(4-(6-amino-5-(5-(2,6-dichlorophenyl)-1,3,4-oxadiazol-2-yl)pyridin-3-yl)-1H-pyrazol-1-yl)piperidin-1-yl)ethanone

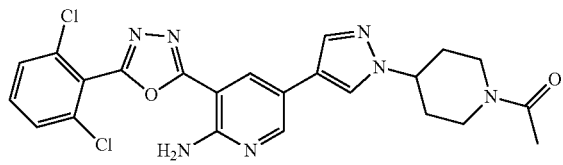 [SMILES: CC(=O)N1CCC(n2cc(-c3cnc(N)c(-c4nnc(-c5c(Cl)cccc5Cl)o4)c3)cn2)CC1]

To a solution of 3-(5-(2,6-dichlorophenyl)-1,3,4-oxadiazol-2-yl)-5-(1-piperidin-4-yl)-1H-pyrazol-4-yl)pyridin-2-amine (62.0 mg, 0.136 mmol) in dichloromethane (3 mL) was added acetic anhydride (0.013 mL, 0.136 mmol), followed by the addition of triethylamine (0.098 mL, 0.700 mmol) at 0° C. The mixture was stirred at ambient temperature for 3 h, diluted with dichloromethane (20 mL), washed with saturated sodium bicarbonate (10 mL) and brine (10 mL). The volatiles were removed in vacuo and the residue was purified by flash chromatography eluted with 5% methanol in dichloromethane to afford the title compound as a pale brown solid in 81% yield (55 mg). $^1$H NMR (400 Hz, CDCl$_3$): δ 8.35 (d, J=2.4 Hz, 1H), 8.19 (d, J=2.4 Hz, 1H), 7.41 (s, 1H), 7.65 (s, 1H), 7.53-7.50 (m, 3H), 7.10 (br s, 2H), 4.79-4.72 (m, 1H), 4.43-4.33 (m, 1H), 4.02-3.94 (m, 1H), 3.30-3.21 (m, 1H), 2.82-2.73 (m, 1H), 2.30-2.16 (m, 2H), 2.14 (s, 3H), 2.04-1.90 (m, 2H); MS (ES+): m/z 498.3, 499.3 and 500.3 (M+1).

Example 4.1

Synthesis of 1-(4-(4-(6-amino-5-(3-phenyl-1,2,4-oxadiazol-5-yl)pyridin-3-yl)-1H-pyrazol-1-yl)piperidin-1-yl)ethanone

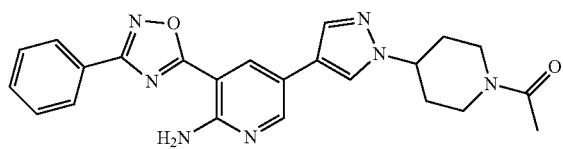 [SMILES: CC(=O)N1CCC(n2cc(-c3cnc(N)c(-c4nc(-c5ccccc5)no4)c3)cn2)CC1]

Following the procedure as described in Example 4, making variations using 3-(3-phenyl-1,2,4-oxadiazol-5-yl)-5-(1-(piperidin-4-yl)-1H-pyrazol-4-yl)pyridin-2-amine to replace 3-(5-(2,6-dichlorophenyl)-1,3,4-oxadiazol-2-yl)-5-(1-piperidin-4-yl)-1H-pyrazol-4-yl)pyridin-2-amine to react with acetic anhydride, the title compound was obtained as a pale yellow solid in 60% yield. $^1$H NMR (400 MHz, CDCl$_3$): δ8.46 (d, J=2.4 Hz, 1H), 8.33 (d, J=2.4 Hz, 1H), 8.18-8.13 (m, 2H), 7.78 (s, 1H), 7.68 (s, 1H), 7.57-7.50 (m, 3H), 6.67 (br s, 2H), 4.82-4.74 (m, 1H), 4.44-4.35 (m, 1H), 4.04-3.96 (m, 1H), 3.32-3.22 (m, 1H), 2.85-2.76 (m, 1H), 2.32-2.19 (m, 2H), 2.16 (s, 3H), 1.90-1.74 (m, 2H); MS (ES+): m/z 430.5 (M+1).

Example 5

Synthesis of 3-(5-(2,6-dichlorophenyl)-1,3,4-oxadiazol-2-yl)-5-(1-(1-methylpiperidin-4-yl)-1H-pyrazol-4-yl)pyridine-2-amine

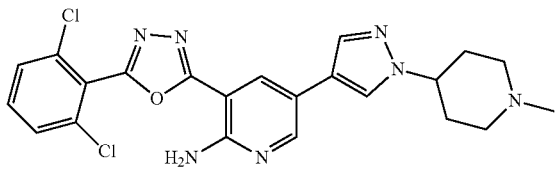 [SMILES: CN1CCC(n2cc(-c3cnc(N)c(-c4nnc(-c5c(Cl)cccc5Cl)o4)c3)cn2)CC1]

To a cooled (0° C.) solution of 3-(5-(2,6-dichlorophenyl)-1,3,4-oxadiazol-2-yl)-5-(1-piperidin-4-yl)-1H-pyrazol-4-yl)pyridin-2-amine (62.0 mg, 0.136 mmol) in dichloromethane/methanol (2 mL/2 mL) was added 37% formaldehyde in water (0.0110 mL, 0.148 mmol). Sodium cyanoborohydride (11.0 mg, 0.148 mmol) was added 10 minutes later. The mixture was stirred at 0° C. for 1 h, then at ambient temperature for 1 h, and evaporated. The residue was purified by flash chromatography eluted with 3-5% methanol in dichloromethane containing 0.1% ammonium hydroxide to afford the title compound as a yellow solid in 81% yield (52 mg). $^1$H NMR (400 Hz, CDCl$_3$): δ 8.41 (d, J=2.4 Hz, 1H), 8.11 (d, J=2.4 Hz, 1H), 7.22 (s, 1H), 7.66 (s, 1H), 7.53-7.48 (m, 3H), 6.62 (br s, 2H), 4.25-4.15 (m, 1H), 3.22-3.03 (m, 2H), 2.40 (s, 3H), 2.34-2.20 (m, 4H), 2.20-2.08 (m, 2H); MS (ES+): m/z 470.3, 471.3 and 472.4 (M+1).

The table below shows additional examples of compounds of Formula (IA4) that were prepared according to the above process.

| Ex. No. | Chemical Name | Starting Material and Yield | Characterization Data |
|---|---|---|---|
| 5.1 | 5-(1-(1-methylpiperidin-4-yl)-1H-pyrazol-4-yl)-3-(5-phenyl-1,2,4-oxadiazol-3-yl)pyridin-2-amine | 3-(5-phenyl-1,2,4-oxadiazol-3-yl)-5-(1-(piperidin-4-yl)-1H-pyrazol-4-yl)pyridin-2-amine and formaldehyde; 58% | $^1$H NMR (400 MHz, CDCl$_3$) δ 8.51 (d, J = 2.4 Hz, 1H), 8.39 (d, J = 2.4 Hz, 1H), 8.27-8.23 (m, 2H), 7.79 (s, 1H), 7.71 (s, 1H), 7.67-7.62 (m, 1H), 7.61-7.56 (m, 2H), 6.19 (br s, 2H), 4.23-4.14 (m, 1H), 3.06-2.98 (m, 2H), 2.36 (s, 3H), 2.26-2.09 (m, 6H); |

-continued

| Ex. No. | Chemical Name | Starting Material and Yield | Characterization Data |
|---|---|---|---|
| 5.2 | 5-(1-(1-methylpiperidin-4-yl)-1H-pyrazol-4-yl)-3-(3-phenyl-1,2,4-oxadiazol-5-yl)pyridin-2-amine | 3-(3-phenyl-1,2,4-oxadiazol-5-yl)-5-(1-(piperidin-4-yl)-1H-pyrazol-4-yl)pyridin-2-amine and formaldehyde; 39% | (ES+): m/z 402.4 (M + 1). <br> $^1$H NMR (400 MHz, DMSO-d$_6$): δ 8.60 (d, J = 2.4 Hz, 1H), 8.39 (d, J = 2.4 Hz, 1H), 8.33 (s, 1H), 8.17-8.13 (m, 2H), 7.96 (s, 1H), 7.63-7.54 (m, 3H), 7.48 (br s, 2H), 4.33-4.22 (m, 1H), 3.24-3.12 (m, 2H), 2.73-2.60 (m, 2H), 2.52 (s, 3H), 2.20-2.00 (m, 4H); MS (ES+): m/z 402.4 (M + 1). |
| 5.3 | 3-(3-(2,6-dichlorophenyl)-1,2,4-oxadiazol-5-yl)-5-(1-(1-methylpiperidin-4-yl)-1H-pyrazol-4-yl)pyridin-2-amine | 3-(3-(2,6-dichlorophenyl)-1,2,4-oxadiazol-5-yl)-5-(1-(piperidin-4-yl)-1H-pyrazol-4-yl)pyridin-2-amine and formaldehyde; 28% | $^1$H NMR (400 MHz, CDCl$_3$): δ 8.47 (d, J = 2.4 Hz, 1H), 8.37 (d, J = 2.4 Hz, 1H), 7.76 (s, 1H), 7.69 (s, 1H), 7.50-7.40 (m, 3H), 6.52 (br s, 2H), 4.25-4.15 (m, 1H), 3.08-2.98 (m, 2H), 2.37 (s, 3H), 2.28-2.10 (m, 6H); MS (ES+): m/z 470.3, 471.3 and 472.3 (M + 1). |
| 5.4 | 3-(3-phenyl-1,2,4-oxadiazol-5-yl)-5-(1-(1-ethylpiperidin-4-yl)-1H-pyrazol-4-yl)pyridin-2-amine | 3-(3-phenyl-1,2,4-oxadiazol-5-yl)-5-(1-(piperidin-4-yl)-1H-pyrazol-4-yl)pyridin-2-amine and acetaldehyde; 43% | $^1$H NMR (400 MHz, CDCl$_3$): δ 8.46 (d, J = 2.4 Hz, 1H), 8.33 (d, J = 2.4 Hz, 1H), 8.19-8.14 (m, 2H), 7.77 (s, 1H), 7.68 (s, 1H), 7.57-7.50 (m, 3H), 6.52 (br s, 2H), 4.25-4.16 (m, 1H), 3.15-3.08 (m, 2H), 2.50 (q, J = 7.2 Hz, 2H), 2.30-2.03 (m, 2H), 2.18-2.08 (m, 4H), 1.14 (t, J = 7.2 Hz, 3H); (ES+): m/z 416.4 (M + 1). |
| 5.5 | 3-(3-(2,6-dichlorophenyl)-1,2,4-oxadiazol-5-yl)-5-(1-(1-dodecylpiperidin-4-yl)-1H-pyrazol-4-yl)pyridin-2-amine | 3-(3-(2,6-dichlorophenyl)-1,2,4-oxadiazol-5-yl)-5-(1-(piperidin-4-yl)-1H-pyrazol-4-yl)pyridin-2-amine and dodecyl aldehyde; 20% | $^1$H NMR (400 MHz, CDCl$_3$) δ 8.47 (d, J = 2.4 Hz, 1H), 8.37 (d, J = 2.0 Hz, 1H), 7.77 (s, 1H), 7.70 (s, 1H), 7.51-7.41 (m, 3H), 6.52 (br s, 2H), 4.23-4.16 (m, 1H), 3.13-3.06 (m, 2H), 2.43-2.35 (m, 2H), 2.25-2.18 (m, 2H), 2.16-2.06 (m, 4H), 1.55-1.47 (m, 2H), 1.35-1.24 (m, 18H), 0.89 (t, J = 6.8 Hz, 3H); MS (ES+): m/z 624.5, 625.5 and 626.5 (M + 1). |
| 5.6 | 3-(3-(2,6-dichlorophenyl)-1,2,4-oxadiazol-5-yl)-5-(1-(1-ethylpiperidin-4-yl)-1H-pyrazol-4-yl)pyridin-2-amine | 3-(3-(2,6-dichlorophenyl)-1,2,4-oxadiazol-5-yl)-5-(1-(piperidin-4-yl)-1H-pyrazol-4-yl)pyridin-2-amine and acetaldehyde; 25% | $^1$H NMR (400 MHz, CDCl$_3$): δ 8.46 (s, 1H), 8.36 (s, 1H), 7.76 (s, 1H), 7.69 (s, 1H), 7.50-7.38 (m, 3H), 6.70-6.40 (br s, 2H), 4.27-4.15 (m, 1H), 3.60-3.50 (m, 2H), 2.60-2.45 (m, 2H), 2.30-2.00 (m, 6H), 1.14 (t, J = 6.8 Hz, 3H); MS (ES+): m/z 484.3, 485.3 and 486.4 (M + 1). |
| 5.7 | 3-(5-(2,6-dichlorophenyl)-1,3,4-oxadiazol-2-yl)-5-(1-(1-ethylpiperidin-4-yl)-1H-pyrazol-4-yl)pyridin-2-amine | acetaldehyde and 3-(5-(2,6-dichlorophenyl)-1,3,4-oxadiazol-2-yl)-5-(1-piperidin-4-yl)-1H-pyrazol-4-yl)pyridin-2-amine; 61% | $^1$H NMR (400 MHz, CDCl$_3$): δ 8.41 (d, J = 2.4 Hz, 1H), 8.11 (d, J = 2.4 Hz, 1H), 7.72 (s, 1H), 7.66 (s, 1H), 7.53-7.46 (m, 3H), 6.72-6.54 (br s, 2H), 4.24-4.14 (m, 1H), 3.07-2.98 (m, 2H), 2.55-2.45 (m, 2H), 2.28-2.04 (m, 6H), 1.33 (t, J = 7.2 Hz, 3H); MS (ES+): m/z 484.3, 485.3 and 486.3 (M + 1). |
| 5.8 | 3-(5-(2,6-dichlorophenyl)-1,3,4-oxadiazol-2-yl)-5-(1-(1-dodecylpiperidin-4-yl)-1H-pyrazol-4-yl)pyridin-2-amine | dodecyl aldehyde and 3-(5-(2,6-dichlorophenyl)-1,3,4-oxadiazol-2-yl)-5-(1-piperidin-4-yl)-1H-pyrazol-4-yl)pyridin-2-amine; 51% | $^1$H NMR (400 MHz, CDCl$_3$): δ 8.41 (d, J = 2.4 Hz, 1H), 8.11 (d, J = 2.4 Hz, 1H), 7.72 (s, 1H), 7.66 (s, 1H), 7.54-7.46 (m, 3H), 6.76-6.50 (br s, 2H), 4.23-4.13 (m, 1H), 3.13-3.05 (m, 2H), 2.39 (t, J = 7.2 Hz, 2H), 2.25-2.00 (m, 6H), 1.55-1.45 (m, 2H), 1.35-1.20 (m, 18H), 0.88 (t, J = 7.2 Hz, 3H). MS (ES+): m/z 624.4, 625.4 and 626.4 (M + 1). |

Example 6

Synthesis of 1-(4-(4-(6-amino-5-(5-(2,6-dichlorophenyl)-1,3,4-oxadiazol-2-yl)pyridin-3-yl)-1H-pyrazol-1-yl)piperidin-1-yl)-4-methylpentan-1-one

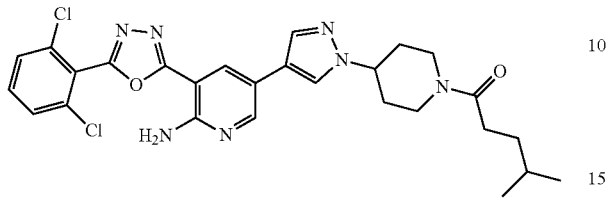

To a mixture of 3-(5-(2,6-dichlorophenyl)-1,3,4-oxadiazol-2-yl)-5-(1-(piperidin-4-yl)-1H-pyrazol-4-yl)pyridin-2-amine (63.0 mg, 0.138 mmol), 4-methylpentanoic acid (0.021 mL, 0.166 mmol) and 1-[bis(dimethylamino)methylene]-1H-1,2,3-triazolo[4,5-b]pyridinium 3-oxid hexafluorophosphate (78.7 mg, 99%, 0.20 mmol) dissolved in N,N-dimethylformamide (1.0 mL) was added triethylamine (0.039 mL, 0.276 mmol). The resulting mixture was stirred at ambient temperature overnight, and diluted with ethyl acetate (30 mL), washed with brine (2×30 mL), and dried over sodium sulfate. After filtration and removal of the solvent, the residue was purified by column chromatography eluted with dichloromethane:methanol:NH$_4$OH (from 200:6:1 to 200:8:1) to afford the title compound as a yellow solid in 39% yield (30.0 mg). $^1$H NMR (400 MHz, CDCl$_3$): δ 8.38 (d, J=2.4 Hz, 1H), 8.12 (d, J=2.4 Hz, 1H), 7.73 (s, 1H), 7.64 (s, 1H), 7.51-7.49 (m, 3H), 6.86-6.60 (br s, 2H), 4.80-4073 (m, 1H), 4.40-4.35 (m, 1H), 4.04-3.98 (m, 1H), 3.25-3.18 (m, 1H), 2.80-2.71 (m, 1H), 2.38-2.32 (m, 2H), 2.30-2.14 (m, 2H), 2.03-1.88 (m, 2H), 1.67-1.49 (m, 3H), 0.91 (d, J=6.4 Hz, 6H). MS: (ES+): m/z 554.4, 555.3, and 556.3 (M+1), 576.3, 577.3 and 578.3 (M+Na).

Example 7

Synthesis of (4-(4-(6-amino-5-(3-phenyl-1,2,4-oxadiazol-5-yl)pyridin-3-yl)-1H-pyrazol-1-yl)piperidin-1-yl)(cyclopropyl)methanone

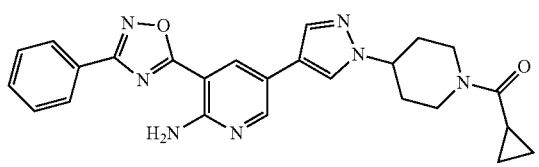 [SMILES: Nc1ncc(-c2cnn(C3CCN(C(=O)C4CC4)CC3)c2)cc1-c1nc(-c2ccccc2)no1]

To a solution of 3-(3-phenyl-1,2,4-oxadiazol-5-yl)-5-(1-(piperidin-4-yl)-1H-pyrazol-4-yl)pyridin-2-amine (60 mg, 0.15 mmol) in 1 mL of pyridine was added cyclopropanecarbonyl chloride (28 μL, 0.30 mmol). The resulting mixture was stirred at ambient temperature for 2 hours, followed by the addition of 20 mL of water to yield yellow precipitates. The precipitates were collected by filtration, washed with water and purified by column chromatography eluted with 5% methanol in dichloromethane to afford the title compound as a yellow solid in 66% yield (45 mg). $^1$H NMR (400 MHz, CDCl$_3$): δ 8.46 (d, J=2.4 Hz, 1H), 8.33 (d, J=2.4 Hz, 1H), 8.18-8.13 (m, 2H), 7.79 (s, 1H), 7.70 (s, 1H), 7.57-7.50 (m, 3H), 6.69 (br s, 2H), 4.85-4.73 (m, 1H), 4.48-4.35 (m, 2H), 3.39-3.25 (m, 1H), 2.90-2.76 (m, 1H), 2.38-2.20 (m, 2H), 2.15-1.95 (m, 2H), 1.84-1.76 (m, 1H), 1.05-0.98 (m, 2H), 0.84-0.78 (m, 2H); MS (ES+): m/z 456.5 (M+1).

Example 7.1

Synthesis of (4-(4-(6-amino-5-(5-(2,6-dichlorophenyl)-1,3,4-oxadiazol-2-yl)pyridin-3-yl)-1H-pyrazol-1-yl)piperidin-1-yl)(cyclopropyl)methanone

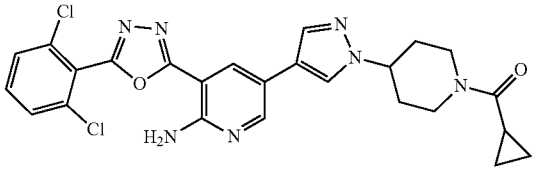 [SMILES: Nc1ncc(-c2cnn(C3CCN(C(=O)C4CC4)CC3)c2)cc1-c1nnc(-c2c(Cl)cccc2Cl)o1]

Following the procedure as described in Example 7, making variations using 3-(5-(2,6-dichlorophenyl)-1,3,4-oxadiazol-2-yl)-5-(1-(piperidin-4-yl)-1H-pyrazol-4-yl)-pyridin-2-amine to replace 3-(3-phenyl-1,2,4-oxadiazol-5-yl)-5-(1-(piperidin-4-yl)-1H-pyrazol-4-yl)pyridin-2-amine to react with cyclopropanecarbonyl chloride, the title compound was obtained as a yellowish solid in 41% yield. $^1$H NMR (400 MHz, CDCl$_3$): δ 8.40 (d, J=2.0 Hz, 1H), 8.14 (d, J=2.0 Hz, 1H), 7.74 (s, 1H), 7.65 (s, 1H), 7.54-7.47 (m, 3H), 6.82 (br s, 2H), 4.82-4.69 (m, 1H), 4.46-4.32 (m, 2H), 3.38-3.22 (m, 1H), 2.88-2.74 (m, 1H), 2.36-2.14 (m, 2H), 2.10-1.90 (m, 2H), 1.82-1.74 (m, 1H), 1.04-0.96 (m, 2H), 0.82-0.75 (m, 2H); MS (ES+): m/z 524.3, 525.3 and 526.3 (M+1).

Example 7.2

Synthesis of (4-(4-(6-amino-5-(5-(2,6-dichlorophenyl)-1,3,4-oxadiazol-2-yl)pyridin-3-yl)-1H-pyrazol-1-yl)piperidin-1-yl)(phenyl)methanone

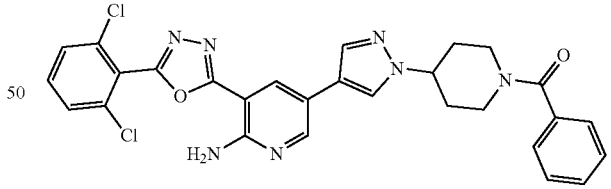

Following the procedure as described in Example 7, making variations using 3-(5-(2,6-dichlorophenyl)-1,3,4-oxadiazol-2-yl)-5-(1-(piperidin-4-yl)-1H-pyrazol-4-yl)-pyridin-2-amine to replace 3-(3-phenyl-1,2,4-oxadiazol-5-yl)-5-(1-(piperidin-4-yl)-1H-pyrazol-4-yl)pyridin-2-amine to react with benzoyl chloride, the title compound was obtained as a yellowish solid in 83% yield. $^1$H NMR (400 MHz, CDCl$_3$): δ 8.42 (s, 1H), 8.12 (s, 1H), 7.75 (s, 1H), 7.67 (s, 1H), 7.53-7.49 (m, 3H), 7.46-7.39 (m, 5H), 6.74 (br s, 2H), 4.95-4.75 (m, 1H), 4.47-4.37 (m, 1H), 4.05-3.78 (m, 1H), 3.25-1.95 (m, 2H), 2.35-2.18 (m, 2H), 2.18-1.98 (m, 2H); MS (ES+): m/z 560.3, 561.3 and 562.3 (M+1).

Example 8

Synthesis of 5-(1-cyclohexyl-1H-pyrazol-4-yl)-3-(5-phenyl-1,2,4-oxadiazol-3-yl)pyridin-2-amine

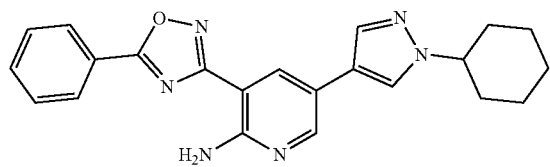 [SMILES: Nc1ncc(-c2cnn(C3CCCCC3)c2)cc1-c1noc(-c2ccccc2)n1]

In a sealed tube, a mixture of 5-bromo-3-(5-phenyl-1,2,4-oxadiazol-3-yl)pyridin-2-amine (70.0 mg, 0.221 mmol), 1-cyclohexyl-4-(4,4,5,5-tetramethyl-1,3,2-dioxaborolan-2-yl)-1H-pyrazole (61.0 mg, 0.221 mmol) and cesium carbonate (145 mg, 0.442 mmol) in 1,4-dioxane/water (2.0 mL, 4:1) was degassed with nitrogen gas for 10 minutes, followed by the addition of tetrakis(triphenylphosphine)palladium (26.0 mg, 22.1 µmol). The mixture was degassed for another 10 minutes. The resulting mixture was sealed and heated at 100° C. overnight. After cooled to ambient temperature, the reaction mixture was filtered through a celite cake, and washed with dichloromethane and methanol. The filtrate was concentrated and the residue was treated with dichloromethane/methanol, and filtered. The filtrate was concentrated and the residue was purified by column chromatography eluted with dichloromethane:methanol from 100:1 to 50:1 to afford the title compound as a white solid in 41% yield (35 mg). $^1$H NMR (400 MHz, CDCl$_3$): δ 8.52 (d, J=2.4 Hz, 1H), 8.40 (d, J=2.4 Hz, 1H), 8.28-8.23 (m, 2H), 7.79 (s, 1H), 7.70 (s, 1H), 7.68-7.63 (m, 1H), 7.62-7.56 (m, 2H), 6.25-6.10 (br s, 2H), 4.21-4.12 (m, 1H), 2.27-2.20 (m, 2H), 2.00-1.90 (m, 2H), 1.85-1.74 (m, 3H), 1.54-1.40 (m, 2H), 1.37-1.25 (m, 1H). MS (ES+): m/z 387.3 (M+1), 409.4 (M+Na).

Example 9

Synthesis of 3-(5-(2,5-dichlorophenyl)-1,2,4-oxadiazol-3-yl)-5-(1-(piperidin-4-yl)-1H-pyrazol-4-yl)pyridin-2-amine

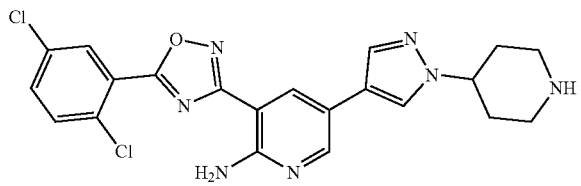 [SMILES: Nc1ncc(-c2cnn(C3CCNCC3)c2)cc1-c1noc(-c2cc(Cl)ccc2Cl)n1]

A. A mixture of 5-bromo-3-(5-cyclohexyl-1,3,4-oxadiazol-2-yl)pyridin-2-amine (80 mg, 0.208 mmol), tert-butyl 4-(4-(4,4,5,5-tetramethyl-1,3,2-dioxaborolan-2-yl)-1H-pyrazol-1-yl)piperidine-1-carboxylate (94 mg, 0.249 mmol) and cesium carbonate (338 mg, 1.04 mmol) in a sealed tube with 5 mL of 10:1 dioxane:water was degassed with nitrogen for 10 minutes, followed by the addition of tetrakis(triphenylphosphine)-palladium(0) (24 mg, 0.021 mmol). The mixture was degassed for another 10 minutes and then sealed and heated at 110° C. overnight. After removal of the solvents, the residue was purified by column chromatography and preparative thin layer chromatography eluted with 40% ethyl acetate in hexane to afford tert-butyl 4-(4-(6-amino-5-(5-(2,5-dichlorophenyl)-1,2,4-oxadiazol-3-yl)pyridin-3-yl)-1H-pyrazol-1-yl)piperidine-1-carboxylate as a yellowish solid in 30% yield (33 mg). $^1$H NMR (400 MHz, CDCl$_3$): δ8.48 (d, J=2.4 Hz, 1H), 8.40 (d, J=2.4 Hz, 1H), 8.19 (d, J=2.4 Hz, 1H), 7.80 (s, 1H), 7.69 (s, 1H), 7.57 (d, J=8.8 Hz, 1H), 7.53 (dd, J=8.8, 2.4 Hz, 1H), 6.19 (br s, 2H), 4.38-4.20 (m, 1H), 3.30-3.27 (m, 2H), 2.95-2.80 (m, 2H), 2.23-2.18 (m, 2H), 2.05-1.95 (m, 2H), 1.48 (s, 9H).

B. To a suspension of tert-butyl 4-(4-(6-amino-5-(5-(2,5-dichlorophenyl)-1,2,4-oxadiazol-3-yl)pyridin-3-yl)-1H-pyrazol-1-yl)piperidine-1-carboxylate (20 mg, 0.15 mmol) in 5 mL of dichloromethane was added 3 mL of 2M HCl in ether. The resulting mixture was stirred at room temperature overnight. After removal of the solvents in vacuo, the residue was purified by preparative thin layer chromatography eluted with 1:10:89 ammonium hydroxide:methanol:dichloromethane to afford the title compound as a white solid in 68% yield (11 mg). $^1$H NMR (400 MHz, CDCl$_3$): δ8.49 (d, J=2.4 Hz, 1H), 8.41 (d, J=2.4 Hz, 1H), 8.19 (d, J=2.4 Hz, 1H), 7.79 (s, 1H), 7.71 (s, 1H), 7.57 (d, J=8.8 Hz, 1H), 7.52 (dd, J=8.8, 2.4 Hz, 1H), 6.19 (br s, 2H), 4.28 (m, 1H), 3.30-3.27 (m, 2H), 2.85-2.75 (m, 2H), 2.26-2.20 (m, 2H), 2.02-1.91 (m, 2H); MS (ES+): m/z 456.3 and 458.3 (M+1).

Example 10

Synthesis of 3-(5-phenyl-1,2,4-oxadiazol-3-yl)-5-(1-(tetrahydro-2H-pyran-4-yl)-1H-pyrazol-4-yl)pyridin-2-amine

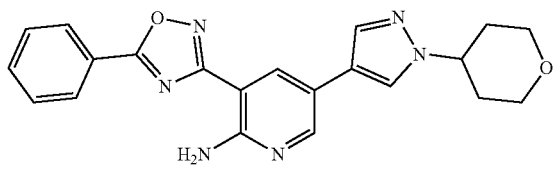 [SMILES: Nc1ncc(-c2cnn(C3CCOCC3)c2)cc1-c1noc(-c2ccccc2)n1]

A mixture of 5-bromo-3-(5-phenyl-1,2,4-oxadiazol-3-yl)pyridin-2-amine (50 mg, 0.16 mmol), 1-(tetrahydro-2H-pyran-4-yl)-4-(4,4,5,5-tetramethyl-1,3,2-dioxaborolan-2-yl)-1H-pyrazole (55 mg, 0.20 mmol), and cesium carbonate (0.22 g, 0.82 mmol) in 3 mL of 10:1 dioxane:water in a sealed tube was purged with nitrogen gas for 10 minutes, followed by the addition of tetrakis(triphenylphosphine)-palladium(0) (10 mg, 0.008 mmol). The mixture was purged for another 10 minutes and heated at 110° C. overnight. After removal of the solvents, the residue was purified by column chromatography and preparative thin layer chromatography eluted with 2% methanol in dichloromethane to afford the title compound as a white solid in 39% yield (25 mg). $^1$H NMR (400 MHz, CDCl$_3$): δ8.52 (d, J=2.4 Hz, 1H), 8.40 (d, J=2.0 Hz, 1H), 8.28-8.23 (m, 2H), 7.81 (s, 1H), 7.72 (s, 1H), 7.68-7.63 (m, 1H), 7.62-7.56 (m, 2H), 6.20 (br s, 2H), 4.47-4.37 (m, 1H), 4.20-4.10 (m, 2H), 3.63-3.54 (m, 2H), 2.23-2.10 (m, 4H); MS (ES+): m/z 389.2 (M+1).

Example 11

Synthesis of 3-(5-phenyl-1,2,4-oxadiazol-3-yl)-5-(1-(piperidin-4-yl)-1H-pyrazol-4-yl)pyridin-2-amine

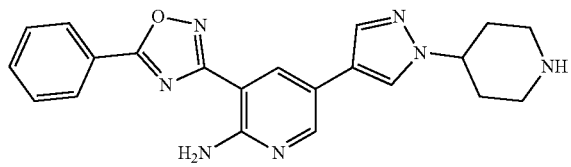 [SMILES: Nc1ncc(-c2cnn(C3CCNCC3)c2)cc1-c1noc(-c2ccccc2)n1]

A. A mixture of 5-bromo-3-(5-phenyl-1,2,4-oxadiazol-3-yl)pyridin-2-amine (100 mg, 0.33 mmol), tert-butyl 4-(4-(4,4,5,5-tetramethyl-1,3,2-dioxaborolan-2-yl)-1H-pyrazol-1-yl)piperidine-1-carboxylate (0.15 mg, 0.40 mmol), and cesium carbonate (0.54 g, 1.65 mmol) in 5 mL of 10:1 dioxane:water in a sealed tube was purged with nitrogen gas for 10 min, followed by the addition of tetrakis(triphenylphosphine)palladium(0) (19 mg, 0.05 mmol). The mixture was purged for another 10 minutes and then heated at 110° C. overnight. After removal of the solvents, the residue was purified by column chromatography eluted with 2% methanol in dichloromethane to afford tert-butyl 4-(4-(6-amino-5-(5-phenyl-1,2,4-oxadiazol-3-yl)pyridin-3-yl)-1H-pyrazol-1-yl)piperidine-1-carboxylate as a yellowish solid in 63% yield (100 mg). $^1$H NMR (400 MHz, CDCl$_3$): δ8.51 (d, J=2.4 Hz, 1H), 8.39 (d, J=2.4 Hz, 1H), 8.28-8.23 (m, 2H), 7.81 (s, 1H), 7.70 (s, 1H), 7.68-7.63 (m, 1H), 7.62-7.57 (m, 2H), 6.19 (br s, 2H), 4.47-4.20 (m, 3H), 3.00-2.85 (m, 2H), 2.24-2.10 (m, 2H), 2.05-1.92 (m, 2H), 1.48 (s, 9H).

B. To a suspension of tert-butyl 4-(4-(6-amino-5-(5-phenyl-1,2,4-oxadiazol-3-yl)pyridin-3-yl)-1H-pyrazol-1-yl)piperidine-1-carboxylate (100 mg, 0.20 mmol) in 5 mL of dichloromethane was added 3 mL of 2M HCl in ether. The resulting mixture was stirred at room temperature for 2 hours, then diluted with 20 mL of dichloromethane, and washed with saturated sodium bicarbonate solution. The organic solution was collected and dried over anhydrous sodium sulfate. After filtration and removal of the solvent in vacuo, the residue was purified by column chromatography eluted with 1:10:89 ammonium hydroxide:methanol:dichloromethane to afford the title compound as a yellow solid in 50% yield (40 mg). $^1$H NMR (400 MHz, CDCl$_3$): δ8.52 (d, J=2.4 Hz, 1H), 8.39 (d, J=2.4 Hz, 1H), 8.28-8.23 (m, 2H), 7.80 (s, 1H), 7.72 (s, 1H), 7.68-7.63 (m, 1H), 7.62-7.57 (m, 2H), 6.19 (br s, 2H), 4.33-4.24 (m, 1H), 3.33-3.24 (m, 2H), 2.86-2.76 (m, 2H), 2.26-2.18 (m, 2H), 2.02-1.90 (m, 2H); MS (ES+): m/z 388.4 (M+1).

Example 12

Synthesis of 1-(4-(4-(6-amino-5-(5-(2,6-dichlorophenyl)-1,3,4-oxadiazol-2-yl)pyridin-3-yl)-1H-pyrazol-1-yl)piperidin-1-yl)-2-phenylethanone

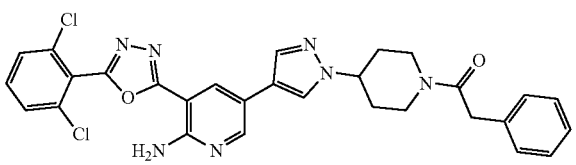 [SMILES: Nc1ncc(-c2cnn(C3CCN(C(=O)Cc4ccccc4)CC3)c2)cc1-c1nnc(-c2c(Cl)cccc2Cl)o1]

To a suspension of 3-(5-(2,6-dichlorophenyl)-1,3,4-oxadiazol-2-yl)-5-(1-(piperidin-4-yl)-1H-pyrazol-4-yl)pyridin-2-amine (50 mg, 0.11 mmol) in 5 mL of dichloromethane at room temperature was added triethylamine (77 μL, 0.55 mmol), followed by the addition of phenylacetyl chloride (18 μL, 0.13 mmol). The resulting mixture was stirred at room temperature for 1 hour. After removal of the solvent in vacuo, the residue was purified by column chromatography and preparative thin layer chromatography eluted with neat ethyl acetate to afford the title compound as a yellow solid in 34% yield (21 mg). $^1$H NMR (400 MHz, CDCl$_3$): δ 8.40 (d, J=2.4 Hz, 1H), 8.10 (d, J=2.4 Hz, 1H), 7.72 (s, 1H), 7.56 (s, 1H), 7.53-7.49 (m, 3H), 7.36-7.32 (m, 2H), 7.29-7.24 (m, 3H), 6.64 (br s, 2H), 4.83-4.73 (m, 1H), 4.48-4.38 (m, 1H), 4.07-3.97 (m, 1H), 3.78 (s, 2H), 3.22-3.11 (m, 1H), 2.86-2.75 (m, 1H), 2.25-2.15 (m, 1H), 2.15-2.05 (m, 1H), 2.00-1.86 (m, 1H), 1.76-1.60 (m, 1H); MS (ES+): m/z 596.2, 597.2 and 598.2 (M+Na).

Example 12.1

Synthesis of (4-(4-(6-amino-5-(3-phenyl-1,2,4-oxadiazol-5-yl)pyridin-3-yl)-1H-pyrazol-1-yl)piperidin-1-yl)(phenyl)methanone

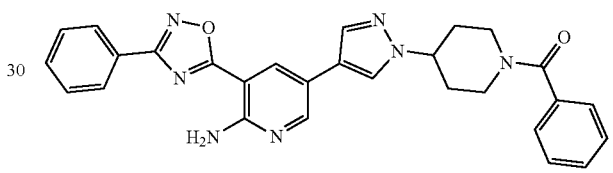

Following the procedure as described in Example 12, making variations using 3-(3-phenyl-1,2,4-oxadiazol-5-yl)-5-(1-(piperidin-4-yl)-1H-pyrazol-4-yl)pyridin-2-amine to replace 3-(5-(2,6-dichlorophenyl)-1,3,4-oxadiazol-2-yl)-5-(1-piperidin-4-yl)-1H-pyrazol-4-yl)pyridin-2-amine to react with benzoyl chloride, the title compound was obtained as a pale yellowish solid in 45% yield. $^1$H NMR (400 MHz, CDCl$_3$): δ 8.47 (d, J=2.4 Hz, 1H), 8.35 (d, J=2.4 Hz, 1H), 8.19-8.15 (m, 2H), 7.80 (s, 1H), 7.71 (s, 1H), 7.57-7.53 (m, 3H), 7.47-7.43 (m, 5H), 6.68 (br s, 2H), 4.98-4.82 (m, 1H), 4.50-4.41 (m, 1H), 4.10-3.95 (m, 1H), 3.25-3.00 (m, 2H), 2.38-2.20 (m, 2H), 2.20-2.03 (m, 2H); MS (ES+): m/z 492.4 (M+1).

Example 12.2

Synthesis of 1-(4-(6-amino-5-(3-phenyl-1,2,4-oxadiazol-5-yl)pyridin-3-yl)-1H-pyrazol-1-yl)piperidin-1-yl)-2-phenylethanone

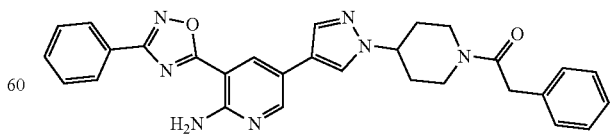

Following the procedure as described in Example 12, making variations using 3-(3-phenyl-1,2,4-oxadiazol-5-yl)-5-(1-(piperidin-4-yl)-1H-pyrazol-4-yl)pyridin-2-amine to replace 3-(5-(2,6-dichlorophenyl)-1,3,4-oxadiazol-2-yl)-5-

(1-piperidin-4-yl)-1H-pyrazol-4-yl)pyridin-2-amine to react with phenylacetyl chloride, the title compound was obtained as a pale yellowish solid in 49% yield. $^1$H NMR (400 MHz, CDCl$^3$): δ 8.43 (d, J=2.4 Hz, 1H), 8.31 (d, J=2.4 Hz, 1H), 8.19-8.13 (m, 2H), 7.75 (s, 1H), 7.59 (s, 1H), 7.56-7.49 (m, 3H), 7.39-7.24 (m, 5H), 6.68 (br s, 2H), 4.85-4.75 (m, 1H), 4.40-4.28 (m, 1H), 4.08-3.98 (m, 1H), 3.80 (s, 2H), 3.25-3.12 (m, 1H), 2.88-2.78 (m, 1H), 2.28-2.17 (m, 1H), 2.17-2.06 (m, 1H), 2.02-1.89 (m, 1H), 1.78-1.65 (m, 1H); MS (ES+): m/z 506.4 (M+1).

Example 13

Synthesis of 3-(5-phenyloxazol-2-yl)-5-(1-(tetrahydro-2H-pyran-4-yl)-1H-pyrazol-4-yl)pyridin-2-amine

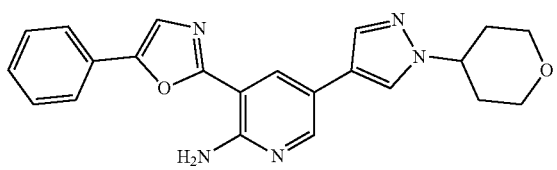 [SMILES: Nc1ncc(-c2cnn(C3CCOCC3)c2)cc1-c1ncc(-c2ccccc2)o1]

A mixture of 5-bromo-3-(5-phenyloxazol-2-yl)pyridin-2-amine (60 mg, 0.20 mmol), 1-(tetrahydro-2H-pyran-4-yl)-4-(4,4,5,5-tetramethyl-1,3,2-dioxaborolan-2-yl)-1H-pyrazole (56 mg, 0.20 mmol) and cesium carbonate (0.32 g, 1.00 mmol) in a sealed tube with 5 mL of 10:1 dioxane:water was degassed for 10 min. After the addition of tetrakis(triphenylphosphine)palladium(0) (23 mg, 0.02 mmol), the mixture was degassed for another 10 minutes. The resulting mixture was sealed and heated at 100° C. overnight. After removal of the solvent in vacuo, the residue was purified by column chromatography eluted with ethyl acetate to afford the title compound as a yellow solid in 18% yield (14 mg). $^1$H NMR (400 MHz, CDCl$_3$): δ 8.32 (d, J=2.4 Hz, 1H), 8.24 (d, J=2.4 Hz, 1H), 7.79 (s, 1H), 7.77-7.72 (m, 2H), 7.69 (s, 1H), 7.50-7.44 (m, 3H), 7.42-7.36 (m, 1H), 6.68 (br s, 2H), 4.50-4.38 (m, 1H), 4.20-4.13 (m, 2H), 3.63-3.53 (m, 2H), 2.22-2.15 (m, 4H); MS (ES+): m/z 388.3 (M+1).

The table below shows additional examples of compounds of Formula (IA1) that were prepared according to the above process.

| Ex. No. | Chemical Name | Starting Material and Yield | Characterization Data |
|---|---|---|---|
| 13.1 | tert-butyl 4-(4-(6-amino-5-(5-phenyloxazol-2-yl)pyridin-3-yl)-1H-pyrazol-1-yl)piperidine-1-carboxylate | tert-butyl 4-(4-(4,4,5,5-tetramethyl-1,3,2-dioxaborolan-2-yl)-1H-pyrazol-1-yl)piperidine-1-carboxylate and 5-bromo-3-(5-phenyloxazol-2-yl)pyridin-2-amine; 75% | $^1$H NMR (400 MHz, CDCl$_3$): δ 8.30 (d, J = 2.4 Hz, 1H), 8.22 (d, J = 2.4 Hz, 1H), 7.78 (s, 1H), 7.75-7.71 (m, 2H), 7.66 (s, 1H), 7.50-7.44 (m, 3H), 7.40-7.34 (m, 1H), 6.68 (br s, 2H), 4.38-4.22 (m, 3H), 3.00-2.86 (m, 2H), 2.24-2.14 (m, 2H), 2.06-1.92 (m, 2H), 1.47 (s, 9H). |
| 13.2 | 3-(5-(4-chlorophenyl)oxazol-2-yl)-5-(1-(tetrahydro-2H-pyran-4-yl)-1H-pyrazol-4-yl)pyridin-2-amine | 5-bromo-3-(5-(4-chlorophenyl)oxazol-2-yl)pyridin-2-amine and 1-(tetrahydro-2H-pyran-4-yl)-4-(4,4,5,5-tetramethyl-1,3,2-dioxaborolan-2-yl)-1H-pyrazole; 12% | $^1$H NMR (400 MHz, DMSO-d$_6$): δ 8.40 (d, J = 2.4 Hz, 1H), 8.37 (d, J = 2.4 Hz, 1H), 8.28 (s, 1H), 7.97-7.91 (m, 4H), 7.55 (d, J = 8.4 Hz, 2H), 7.34 (br s, 2H), 4.44-4.34 (m, 1H), 3.98-3.90 (m, 2H), 3.50-3.41 (m, 2H), 2.04-1.90 (m, 4H); MS (ES+): m/z 422.3 (M + 1). |
| 13.3 | tert-butyl 4-(4-(6-amino-5-(5-(4-chlorophenyl)oxazol-2-yl)pyridin-3-yl)-1H-pyrazol-1-yl)piperidine-1-carboxylate | tert-butyl 4-(4-(4,4,5,5-tetramethyl-1,3,2-dioxaborolan-2-yl)-1H-pyrazol-1-yl)piperidine-1-carboxylate and 5-bromo-3-(5-(4-chlorophenyl)oxazol-2-yl)pyridin-2-amine; 90% | $^1$H NMR (400 MHz, CDCl$_3$): δ 8.31 (d, J = 2.4 Hz, 1H), 8.20 (d, J = 2.4 Hz, 1H), 7.77 (s, 1H), 7.68-7.64 (m, 3H), 7.47-7.42 (m, 3H), 6.68 (br s, 2H), 4.38-4.22 (m, 3H), 3.00-2.84 (m, 2H), 2.24-2.14 (m, 2H), 2.06-1.92 (m, 2H), 1.48 (s, 9H). |
| 13.4 | tert-butyl 4-(4-(6-amino-5-(5-(4-chlorophenyl)oxazol-2-yl)pyridin-3-yl)-1H-pyrazol-1-yl)piperidine-1-carboxylate | tert-butyl 4-(4-(4,4,5,5-tetramethyl-1,3,2-dioxaborolan-2-yl)-1H-pyrazol-1-yl)piperidine-1-carboxylate and 5-bromo-3-(5-(3-chlorophenyl)oxazol-2-yl)pyridin-2-amine; 43% | $^1$H NMR (400 MHz, CDCl$_3$): δ 8.40 (d, J = 2.4 Hz, 1H), 8.22 (d, J = 2.4 Hz, 1H), 7.79 (s, 1H), 7.73-7.70 (m, 1H), 7.68 (s, 1H), 7.63-7.59 (m, 1H), 7.49 (s, 1H), 7.44-7.38 (m, 1H), 7.36-7.32 (m, 1H), 6.68 (br s, 2H), 4.40-4.25 (m, 3H), 3.00-2.87 (m, 2H), 2.24-2.16 (m, 2H), 2.06-1.94 (m, 2H), 1.49 (s, 9H). |
| 13.5 | 3-(5-(3-chlorophenyl)oxazol-2-yl)-5-(1-cyclohexyl-1H-pyrazol-4-yl)pyridin-2-amine | 1-cyclohexyl-4-(4,4,5,5-tetramethyl-1,3,2-dioxaborolan-2-yl)-1H-pyrazole and 5-bromo-3-(5-(3-chlorophenyl)oxazol-2-yl)pyridin-2-amine; 19% | $^1$H NMR (400 MHz, CDCl$_3$): δ 8.33 (d, J = 2.0 Hz, 1H), 8.22 (d, J = 2.4 Hz, 1H), 7.77 (s, 1H), 7.74-7.71 (m, 1H), 7.68 (s, 1H), 7.63-7.60 (m, 1H), 7.49 (s, 1H), 7.43-7.39 (m, 1H), 7.36-7.33 (m, 1H), 6.66 (br s, 2H), 4.23-4.13 (m, 1H), 2.28-2.20 (m, 2H), 1.98-1.91 (m, 2H), 1.87-1.74 (m, 3H), 1.54-1.40 (m, 2H), 1.37-1.29 (m, 1H); MS (ES+): m/z 420.3 and 422.3 (M + 1). |
| 13.6 | 3-(5-(4-Chlorophenyl)oxazol-2-yl)-5-(1- | 1-cyclohexyl-4-(4,4,5,5-tetramethyl-1,3,2-dioxaborolan-2-yl)-1H- | $^1$H NMR (400 MHz, CDCl$_3$): δ 8.34-8.30 (m, 1H), 8.22 (d, J = 2.4 Hz, 1H), 7.56 (s, 1H), 7.69-7.64 (m, 3H), 7.47- |

| Ex. No. | Chemical Name | Starting Material and Yield | Characterization Data |
|---|---|---|---|
| | cyclohexyl-1H-pyrazol-4-yl)pyridine-2-amine | pyrazole and 5-bromo-3-(5-(4-chlorophenyl)oxazol-2-yl)pyridin-2-amine; 4% | 7.43 (m, 3H), 6.65 (s, 2H), 4.22-4.12 (m, 1H), 2.26-2.19 (m, 2H), 1.99-1.80 (m, 2H), 1.85-1.74 (m, 3H), 1.53-1.40 (m, 2H), 1.36-1.25 (m, 1H); (ES+): m/z 420.4, and 422.4 (M + 1). |
| 13.7 | 5-(1-cyclohexyl-1H-pyrazol-4-yl)-3-(5-phenyloxazol-2-yl)pyridin-2-amine | 1-cyclohexyl-4-(4,4,5,5-tetramethyl-1,3,2-dioxaborolan-2-yl)-1H-pyrazole and 5-bromo-3-(5-phenyloxazol-2-yl)pyridin-2-amine; 24% | $^1$H NMR (400 MHz, CDCl$_3$): δ 8.32 (d, J = 2.4 Hz, 1H), 8.24 (d, J = 2.4 Hz, 1H), 7.77-7.72 (m, 3H), 7.66 (s, 1H), 7.52-7.44 (m, 3H), 7.41-7.35 (m, 1H), 6.64 (br s, 2H), 4.22-4.10 (m, 1H), 2.28-2.20 (m, 2H), 1.98-1.92 (m, 2H), 1.86-1.73 (m, 3H), 1.53-1.40 (m, 2H), 1.36-1.25 (m, 1H); MS (ES+): m/z 386.4 (M + 1). |
| 13.8 | 5-(1-cyclohexyl-1H-pyrazol-4-yl)-3-(5-phenylisoxazol-3-yl)pyridin-2-amine | 1-cyclohexyl-4-(4,4,5,5-tetramethyl-1,3,2-dioxaborolan-2-yl)-1H-pyrazole and 5-bromo-3-(5-phenylisoxazol-3-yl)pyridin-2-amine; 35% | $^1$H NMR (400 MHz, CDCl$_3$): δ 8.31 (d, J = 2.0 Hz, 1H), 7.89-7.84 (m, 3H), 7.74 (s, 1H), 7.65 (s, 1H), 7.55-7.45 (m, 3H), 6.95 (s, 1H), 6.28-6.18 (br s, 2H), 4.20-4.12 (m, 1H), 2.27-2.18 (m, 2H), 1.98-1.90 (m, 2H), 1.84-1.72 (m, 3H), 1.53-1.40 (m, 2H), 1.36-1.23 (m, 1H). MS (ES+): m/z 386.2 (M + 1). |
| 13.9 | 5-(1-(tetrahydro-2H-pyran-4-yl)-1H-pyrazol-4-yl)-3-(5-phenylisoxazol-3-yl)pyridin-2-amine | 1-(tetrahydro-2H-pyran-4-yl)-4-(4,4,5,5-tetramethyl-1,3,2-dioxaborolan-2-yl)-1H-pyrazole and 5-bromo-3-(5-phenylisoxazol-3-yl)pyridin-2-amine; 24% | $^1$H NMR (400 MHz, CDCl$_3$): δ 8.31 (d, J = 2.0 Hz, 1H), 7.89-7.84 (m, 3H), 7.76 (s, 1H), 7.67 (s, 1H), 7.55-7.45 (m, 3H), 6.95 (s, 1H), 6.38-6.28 (br s, 2H), 4.45-4.35 (m, 1H), 4.18-4.12 (m, 2H), 3.62-3.54 (m, 2H), 2.21-2.08 (m, 4H). MS (ES+): m/z 386.2 (M + 1). |
| 13.10 | tert-butyl 4-(4-(6-amino-5-(5-phenylisoxazol-3-yl)pyridin-3-yl)-1H-pyrazol-1-yl)piperidine-1-carboxylate | tert-butyl 4-(4-(4,4,5,5-tetramethyl-1,3,2-dioxaborolan-2-yl)-1H-pyrazol-1-yl)piperidine-1-carboxylate and 5-bromo-3-(5-phenylisoxazol-3-yl)pyridin-2-amine; 44% | $^1$H NMR (400 MHz, CDCl$_3$): δ 8.32 (d, J = 2.4 Hz, 1H), 7.90-7.85 (m, 3H), 7.75 (s, 1H), 7.66 (s, 1H), 7.55-7.48 (m, 3H), 6.93 (s, 1H), 6.32-6.24 (br s, 2H), ), 4.37-4.16 (m, 3H), 3.00-2.82 (m, 2H), 2.22-2.10 (m, 2H), 2.10-1.88 (m, 2H), 1.50 (s, 9H). |
| 13.11 | tert-butyl 4-(4-(6-amino-5-(5-phenylfuran-2-yl)pyridin-3-yl)-1H-pyrazol-1-yl)piperidine-1-carboxylate | tert-butyl 4-(4-(4,4,5,5-tetramethyl-1,3,2-dioxaborolan-2-yl)-1H-pyrazol-1-yl)piperidine-1-carboxylate and 5-bromo-3-(5-phenylfuran-2-yl)pyridin-2-amine; 64% | $^1$H NMR (400 MHz, CDCl$_3$): δ 8.20 (d, J = 2.4 Hz, 1H), 7.86 (d, J = 2.4 Hz, 1H), 7.76-7.68 (m, 3H), 7.64 (s, 1H), 7.45-7.39 (m, 2H), 7.33-7.28 (m, 1H), 6.82-6.77 (m, 2H), 5.22 (br s, 2H), 4.36-4.20 (m, 3H), 2.95-2.70 (m, 2H), 2.22-2.15 (m, 2H), 2.05-1.92 (m, 2H), 1.48 (s, 9H). |
| 13.12 | 5-(1-cyclohexyl-1H-pyrazol-4-yl)-3-(5-phenylfuran-2-yl)pyridin-2-amine | 1-cyclohexyl-4-(4,4,5,5-tetramethyl-1,3,2-dioxaborolan-2-yl)-1H-pyrazole and 5-bromo-3-(5-phenylfuran-2-yl)pyridin-2-amine; 24% | $^1$H NMR (400 MHz, CDCl$_3$): δ 8.20 (d, J = 2.4 Hz, 1H), 7.86 (d, J = 2.4 Hz, 1H), 7.73 (s, 1H), 7.72-7.68 (m, 2H), 7.64 (s, 1H), 7.45-7.40 (m, 2H), 7.33-7.28 (m, 1H), 6.80 (d, J = 3.6 Hz, 1H), 6.77 (d, J = 3.6 Hz, 1H), 5.23 (br s, 2H), 4.20-4.10 (m, 1H), 2.26-2.18 (m, 2H), 1.97-1.89 (m, 2H), 1.84-1.72 (m, 2H), 1.52-1.39 (m, 2H), 1.35-1.20 (m, 2H). MS (ES+): m/z 385.3 (M + 1), 407.3 (M + Na). |
| 13.13 | 5-(1-(tetrahydro-2H-pyran-4-yl)-1H-pyrazol-4-yl)-3-(5-phenylfuran-2-yl)pyridin-2-amine | 5-bromo-3-(5-phenylfuran-2-yl)pyridin-2-amine and 1-(tetrahydro-2H-pyran-4-yl)-4-(4,4,5,5-tetramethyl-1,3,2-dioxaborolan-2-yl)-1H-pyrazole; 29% | $^1$H NMR (400 MHz, CDCl$_3$): δ 8.20 (d, J = 2.4 Hz, 1H), 7.86 (d, J = 2.4 Hz, 1H), 7.76 (s, 1H), 7.74-7.71 (m, 1H), 7.71-7.69 (m, 1H), 7.66 (s, 1H), 7.45-7.40 (m, 2H), 7.33-7.28 (m, 1H), 6.80 (d, J = 3.6 Hz, 1H), 6.77 (d, J = 3.6 Hz, 1H), 5.22 (br s, 2H), 4.44-4.35 (m, 1H), 4.18-4.10 (m, 2H), 3.61-3.53 (m, 2H), 2.20-2.08 (m, 4H). MS (ES+): m/z 387.4 (M + 1). |
| 13.14 | tert-butyl 4-(4-(6-amino-5-(5-(pyridin-3-yl)oxazol-2-yl)pyridin-3-yl)-1H-pyrazol-1-yl)piperidine-1-carboxylate | 5-bromo-3-(5-(pyridin-3-yl)oxazol-2-yl)pyridin-2-amine and tert-butyl 4-(4-(4,4,5,5-tetramethyl-1,3,2-dioxaborolan-2-yl)-1H-pyrazol-1-yl)piperidine-1-carboxylate; 59% | $^1$H NMR (400 MHz, CDCl$_3$): δ 9.04-9.01 (m, 1H), 8.64-8.60 (m, 1H), 8.34 (d, J = 2.4 Hz, 1H), 8.24 (d, J = 2.4 Hz, 1H), 8.05-7.99 (m, 1H), 7.78 (s, 1H), 7.68 (s, 1H), 7.57 (s, 1H), 7.46-7.40 (m, 1H), 6.72 (br s, 2H), 4.40-4.20 (m, 3H), 3.00-2.85 (m, 2H), 2.24-2.17 (m, 2H), 2.05-1.94 (m, 2H), 1.49 (s, 9H). |

Example 14

Synthesis of 3-(5-phenyloxazol-2-yl)-5-(piperidin-4-yl)-1H-pyrazol-4-yl)pyridin-2-amine

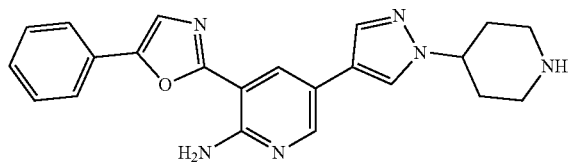 [SMILES: Nc1ncc(-c2cnn(C3CCNCC3)c2)cc1-c1ncc(-c2ccccc2)o1]

To a solution of tert-butyl 4-(4-(6-amino-5-(5-phenyloxazol-2-yl)pyridin-3-yl)-1H-pyrazol-1-yl)piperidine-1-carboxylate (60 mg, 0.12 mmol) in 4 mL of dichloromethane was added 1.0 mL of 2 M hydrochloric acid in ethyl ether. The resulting mixture was stirred at ambient temperature overnight, washed with saturated sodium bicarbonate (3×20 mL) and the organic layer was separated from the aqueous layer. The aqueous solution was extracted with dichloromethane (2×20 mL). The combined organic solution was dried over sodium sulfate and filtered. After removal of the solvent of the organic layer in vacuo, the residue was purified by preparative thin layer chromatography eluted with 1:10:89 ammonium hydroxide:methanol:dichloromethane to afford the title compound as a yellow solid in 56% yield (26 mg). $^1$H NMR (400 MHz, CD$_3$OD): δ 8.38 (d, J=2.4 Hz, 1H), 8.27 (d, J=2.4 Hz, 1H), 8.10 (s, 1H), 7.86 (s, 1H), 7.85-7.80 (m, 2H), 7.63 (s, 1H), 7.49-7.43 (m, 2H), 7.39-7.33 (m, 1H), 4.42-4.32 (m, 1H), 3.30-3.25 (m, 2H), 2.90-2.80 (m, 2H), 2.22-2.14 (m, 2H), 2.10-1.95 (m, 2H); MS (ES+): m/z 387.4 (M+1).

The table below shows additional examples of compounds of Formula (IA1) that were prepared according to the above process.

| Ex. No. | Chemical Name | Starting Material and Yield | Characterization Data |
|---|---|---|---|
| 14.1 | 3-(5-(4-chlorophenyl)oxazol-2-yl)-5-(1-(piperidin-4-yl)-1H-pyrazol-4-yl)pyridin-2-amine | tert-butyl 4-(4-(6-amino-5-(5-(4-chlorophenyl)oxazol-2-yl)pyridin-3-yl)-1H-pyrazol-1-yl)piperidine-1-carboxylate; 53% | $^1$H NMR (400 MHz, DMSO-d$_6$): δ 8.40 (d, J = 2.0 Hz, 1H), 8.38 (d, J = 2.4 Hz, 1H), 8.24 (s, 1H), 7.97-7.90 (m, 4H), 7.58-7.54 (m, 2H), 7.34 (br s, 2H), 4.24-4.14 (m, 1H), 3.10-3.00 (m, 2H), 2.66-2.55 (m, 2H), 2.02-1.93 (m, 2H), 1.88-1.74 (m, 2H); MS (ES+): m/z 421.3 (M + 1). |
| 14.2 | 3-(5-(3-chlorophenyl)oxazol-2-yl)-5-(1-(piperidin-4-yl)-1H-pyrazol-4-yl)pyridin-2-amine | tert-butyl 4-(4-(6-amino-5-(5-(3-chlorophenyl)oxazol-2-yl)pyridin-3-yl)-1H-pyrazol-1-yl)piperidine-1-carboxylate; 98% | $^1$H NMR (400 MHz, DMSO-d$_6$): δ 9.32 (br s, 1H), 9.10 (br s, 1H), 8.85 (d, J = 2.0 Hz, 1H), 8.54 (d, J = 2.0 Hz, 1H), 8.46 (s, 1H), 8.14 (s, 1H), 8.13 (s, 1H), 8.11-8.09 (m, 1H), 7.99-7.95 (m, 1H), 7.57-7.52 (m, 1H), 7.49-7.45 (m, 1H), 4.57-4.48 (m, 1H), 3.42-3.33 (m, 2H), 3.14-3.02 (m, 2H), 2.28-2.15 (m, 4H); MS (ES+): m/z 421.3 and 423.3 (M + 1). |
| 14.3 | 3-(5-phenylisoxazol-3-yl)-5-(1-(piperidin-4-yl)-1H-pyrazol-4-yl)pyridin-2-amine | tert-butyl 4-(4-(6-amino-5-(5-phenylisoxazol-3-yl)pyridin-3-yl)-1H-pyrazol-1-yl)piperidine-1-carboxylate; 31% | $^1$H NMR (400 MHz, CDCl$_3$): δ 8.32 (d, J = 2.4 Hz, 1H), 7.90-7.85 (m, 3H), 7.75 (s, 1H), 7.67 (s, 1H), 7.55-7.47 (m, 3H), 6.95 (s, 1H), 6.35-6.20 (br s, 2H), 4.32-4.23 (m, 1H), 3.31-3.24 (m, 2H), 2.85-2.75 (m, 2H), 2.26-2.18 (m, 2H), 2.02-1.90 (m, 2H). MS (ES+): m/z 387.4 (M + 1). |
| 14.4 | 3-(5-phenylfuran-2-yl)-5-(1-(piperidin-4-yl)-1H-pyrazol-4-yl)pyridin-2-amine | tert-butyl 4-(4-(6-amino-5-(5-phenylfuran-2-yl)pyridin-3-yl)-1H-pyrazol-1-yl)piperidine-1-carboxylate; 65% | $^1$H NMR (400 MHz, CD$_3$OD): δ 8.13 (d, J = 2.4 Hz, 1H), 7.84 (d, J = 2.0 Hz, 1H), 7.72-7.66 (m, 4H), 7.43-7.37 (m, 2H), 7.31-7.25 (m, 1H), 6.78 (d, J = 3.6 Hz, 1H), 6.76 (d, 7 = 3.6 Hz, 1H), 4.30-4.20 (m, 1H), 3.28-3.20 (m, 2H), 2.82-2.74 (m, 2H), 2.23-2.15 (m, 2H), 2.00-1.88 (m, 2H). MS (ES+): m/z 386.4 (M + 1). |
| 14.5 | 5-(1-(piperidin-4-yl)-1H-pyrazol-4-yl)-3-(5-(pyridin-3-yl)oxazol-2-yl)pyridin-2-amine | tert-butyl 4-(4-(6-amino-5-(5-(pyridin-3-yl)oxazol-2-yl)pyridin-3-yl)-1H-pyrazol-1-yl)piperidine-1-carboxylate; 69% | $^1$H NMR (400 MHz, DMSO-d$_6$): δ 9.41-9.37 (m, 1H), 9.27-9.18 (m, 1H), 9.10-8.98 (m, 1H), 8.95 (d, J = 2.4 Hz, 1H), 8.73-8.68 (m, 1H), 8.65-8.61 (m, 1H), 8.56 (d, J = 2.4 Hz, 1H), 8.49 (s, 1H), 8.26 (s, 1H), 8.15 (s, 1H), 7.79-7.73 (m, 1H), 4.57-4.48 (m, 1H), 3.43-3.33 (m, 2H), 3.14-3.02 (m, 2H), 2.28-2.12 (m, 4H); MS (ES+): m/z 388.2 (M + 1). |

Example 15

Synthesis of 1-(4-(6-amino-5-(5-(4-chlorophenyl)oxazol-2-yl)pyridin-3-yl)-1H-pyrazol-1-yl)piperidin-1-yl)ethanone

To a solution of 3-(5-(4-chlorophenyl)oxazol-2-yl)-5-(1-(piperidin-4-yl)-1H-pyrazol-4-yl)pyridin-2-amine (60 mg, 0.14 mmol) in 5 mL of dichloromethane at 0° C. was added acetic anhydride (13 µL, 0.14 mmol), followed by the addition of triethylamine (99 µL, 0.71 mmol). The resulting mixture was stirred at 0° C. for 30 min, then warmed up to ambient temperature and stirred for 3 hours. The solvent was removed in vacuo, and the residue was purified by column chromatography eluted with 5% methanol in dichloromethane followed by recrystallization from methanol to afford the title compound as a yellowish solid in 51% yield (33 mg). $^1$H NMR (400 MHz, DMSO-$d_6$): δ 8.40 (d, J=2.4 Hz, 1H), 8.37 (d, J=2.4 Hz, 1H), 8.27 (s, 1H), 7.96-7.92 (m, 4H), 7.57-7.54 (m, 2H), 7.34 (br s, 2H), 4.49-4.37 (m, 2H), 3.95-3.87 (m, 1H), 3.25-3.16 (m, 1H), 2.75-2.67 (m, 1H), 2.12-2.03 (m, 2H), 2.02 (s, 3H), 1.94-1.85 (m, 1H), 1.81-1.70 (m, 1H); MS (ES+): m/z 463.4 and 465.4 (M+1).

Example 15.1

Synthesis of 1-(4-(6-amino-5-(5-(3-chlorophenyl)oxazol-2-yl)pyridin-3-yl)-1H-pyrazol-1-yl)piperidin-1-yl)ethanone

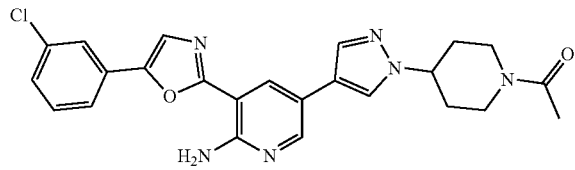 [SMILES: CC(=O)N1CCC(n2cc(-c3cnc(N)c(-c4ncc(-c5cccc(Cl)c5)o4)c3)cn2)CC1]

Following the procedure as described in Example 15, making variations using 3-(5-(3-chlorophenyl)oxazol-2-yl)-5-(1-(piperidin-4-yl)-1H-pyrazol-4-yl)pyridin-2-amine to replace 3-(5-(4-chlorophenyl)oxazol-2-yl)-5-(1-(piperidin-4-yl)-1H-pyrazol-4-yl)pyridin-2-amine to react with acetic anhydride, the title compound was obtained as a yellow solid in 65% yield. $^1$H NMR (400 MHz, CDCl$_3$): δ 8.32 (d, J=2.4 Hz, 1H), 8.22 (d, J=2.4 Hz, 1H), 7.80 (s, 1H), 7.74-7.71 (m, 1H), 7.69 (s, 1H), 7.64-7.60 (m, 1H), 7.50 (s, 1H), 7.45-7.39 (m, 1H), 7.37-7.33 (m, 1H), 6.70 (br s, 2H), 4.84-4.76 (m, 1H), 4.47-4.37 (m, 1H), 4.06-3.97 (m, 1H), 3.32-3.22 (m, 1H), 2.85-2.76 (m, 1H), 2.35-2.20 (m, 2H), 2.17 (s, 3H), 2.10-1.98 (m, 2H); MS (ES+): m/z 485.3 and 487.3 (M+Na).

Example 16

Synthesis of (4-(4-(6-amino-5-(5-(4-chlorophenyl)oxazol-2-yl)pyridin-3-yl)-1H-pyrazol-1-yl)piperidin-1-yl)(cyclopropyl)methanone

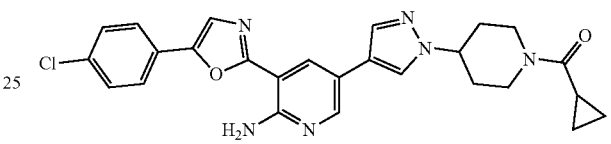

To a solution of 3-(5-(4-chlorophenyl)oxazol-2-yl)-5-(1-(piperidin-4-yl)-1H-pyrazol-4-yl)pyridin-2-amine (60 mg, 0.14 mmol) in 1 mL of pyridine was added cyclopropanecarbonyl chloride (15 µL, 0.17 mmol). The resulting mixture was stirred at ambient temperature for 2 hours. The solvent was removed in vacuo, and the residue was purified by column chromatography eluted with 5% methanol in dichloromethane followed by recrystallization from a mixed solvent of methanol and water to afford the title compound as an orange solid in 63% yield (43 mg). $^1$H NMR (400 MHz, CDCl$_3$): δ 8.31 (s, 1H), 8.21 (s, 1H), 7.78 (s, 1H), 7.70-7.63 (m, 3H), 7.48-7.40 (m, 3H), 6.72 (br s, 2H), 4.85-4.70 (m, 1H), 4.50-4.35 (m, 2H), 3.40-3.22 (m, 1H), 2.91-2.75 (m, 1H), 2.40-2.20 (m, 2H), 2.15-1.90 (m, 2H), 1.85-1.75 (m, 1H), 1.05-0.95 (m, 2H), 0.85-0.74 (m, 2H); MS (ES+): m/z 511.4 and 513.4 (M+Na).

The table below shows additional examples of compounds of Formula (IA1) that were prepared according to the above process.

| Ex. No. | Chemical Name | Starting Material and Yield | Characterization Data |
| --- | --- | --- | --- |
| 16.1 | (4-(4-(6-amino-5-(5-(3-chlorophenyl)oxazol-2-yl)pyridin-3-yl)-1H-pyrazol-1-yl)piperidin-1-yl)(cyclopropyl)methanone | 3-(5-(3-chlorophenyl)oxazol-2-yl)-5-(1-(piperidin-4-yl)-1H-pyrazol-4-yl)pyridin-2-amine and cyclopropane-carbonyl chloride; 36% | $^1$H NMR (400 MHz, CDCl$_3$): δ 8.32 (d, J = 2.4 Hz, 1H), 8.22 (d, J = 2.4 Hz, 1H), 7.79 (s, 1H), 7.73-7.71 (m, 1H), 7.68 (s, 1H), 7.63-7.59 (m, 1H), 7.49 (s, 1H), 7.43-7.39 (m, 1H), 7.36-7.32 (m, 1H), 6.67 (br s, 2H), 4.85-4.70 (m, 1H), 4.50-4.35 (m, 2H), 3.40-3.25 (m, 1H), 2.90-2.75 (m, 1H), 2.37-2.17 (m, 2H), 2.17-1.95 (m, 2H), 1.84-1.78 (m, 1H), 1.05-0.98 (m, 2H), 0.82-0.76 (m, 2H); MS (ES+): m/z 489.3 and 491.3 (M + 1). |
| 16.2 | (4-(4-(6-amino-5-(5-(3-chlorophenyl)oxazol-2-yl)pyridin-3-yl)-1H-pyrazol-1-yl)piperidin-1-yl)(phenyl)methanone | 3-(5-(3-chlorophenyl)oxazol-2-yl)-5-(1-(piperidin-4-yl)-1H-pyrazol-4-yl)pyridin-2-amine and benzoyl chloride; 30% | $^1$H NMR (400 MHz, CDCl$_3$): δ 8.33 (d, J = 2.4 Hz, 1H), 8.22 (d, J = 2.4 Hz, 1H), 7.80 (s, 1H), 7.74-7.72 (m, 1H), 7.70 (s, 1H), 7.64-7.60 (m, 1H), 7.50 (s, 1H), 7.48-7.44 (m, 5H), 7.43-7.40 (m, 1H), 7.37-7.33 (m, 1H), 6.69 (br s, 2H), 5.00-4.80 (m, 1H), 4.50-4.41 (m, 1H), 4.08-3.93 (m, 1H), 3.25-3.00 (m, 2H), 2.38-2.20 (m, 2H), 2.20-2.00 |

| Ex. No. | Chemical Name | Starting Material and Yield | Characterization Data |
|---|---|---|---|
| | | | (m, 2H); MS (ES+): m/z 525.3 and 527.3 (M + 1). |
| 16.3 | 1-(4-(4-(6-amino-5-(5-(3-chlorophenyl)oxazol-2-yl)pyridin-3-yl)-1H-pyrazol-1-yl)piperidin-1-yl)-2-phenylethanone | 3-(5-(3-chlorophenyl)oxazol-2-yl)-5-(1-(piperidin-4-yl)-1H-pyrazol-4-yl)pyridin-2-amine and phenylacetyl chloride; 37% | $^1$H NMR (400 MHz, CDCl$_3$): δ 8.30 (d, J = 2.4 Hz, 1H), 8.20 (d, J = 2.4 Hz, 1H), 7.77 (s, 1H), 7.73-7.71 (m, 1H), 7.63-7.59 (m, 2H), 7.50 (s, 1H), 7.46-7.39 (m, 1H), 7.38-7.33 (m, 3H), 7.31-7.26 (m, 3H), 6.70 (br s, 2H), 4.85-4.76 (m, 1H), 4.42-4.32 (m, 1H), 4.10-4.01 (m, 1H), 3.80 (s, 2H), 3.24-3.15 (m, 1H), 2.88-2.78 (m, 1H), 2.37-2.20 (m, 1H), 2.18-2.08 (m, 1H), 2.05-1.92 (m, 1H), 1.81-1.68 (m, 1H); MS (ES+): m/z 539.3 and 541.3 (M + 1). |
| 16.4 | (4-(4-(6-amino-5-(5-(4-chlorophenyl)oxazol-2-yl)pyridin-3-yl)-1H-pyrazol-1-yl)piperidin-1-yl)(phenyl)methanone | benzoyl chloride and 3-(5-(4-chlorophenyl)oxazol-2-yl)-5-(1-(piperidin-4-yl)-1H-pyrazol-4-yl)pyridin-2-amine; 54% | $^1$H NMR (400 MHz, CDCl$_3$): δ 8.32 (d, J = 2.4 Hz, 1H), 8.21 (d, J = 2.4 Hz, 1H), 7.79 (s, 1H), 7.69-7.65 (m, 3H), 7.48-7.42 (m, 8H), 6.69 (br s, 2H), 4.95-4.80 (m, 1H), 4.50-4.41 (m, 1H), 4.08-3.93 (m, 1H), 3.25-3.00 (m, 2H), 2.38-2.20 (m, 2H), 2.20-2.00 (m, 2H); MS (ES+): m/z 525.3 and 527.3 (M + 1). |
| 16.5 | 1-(4-(4-(6-amino-5-(5-(4-chlorophenyl)oxazol-2-yl)pyridin-3-yl)-1H-pyrazol-1-yl)piperidin-1-yl)-2-phenylethanone | phenylacetyl chloride and 3-(5-(4-chlorophenyl)oxazol-2-yl)-5-(1-(piperidin-4-yl)-1H-pyrazol-4-yl)pyridin-2-amine; 36% | $^1$H NMR (400 MHz, CDCl$_3$): δ 8.29 (d, J = 2.4 Hz, 1H), 8.19 (d, J = 2.4 Hz, 1H), 7.76 (s, 1H), 7.69-7.64 (m, 2H), 7.58 (s, 1H), 7.48-7.42 (m, 3H), 7.38-7.32 (m, 2H), 7.31-7.25 (m, 3H), 6.68 (br s, 2H), 4.85-4.76 (m, 1H), 4.41-4.32 (m, 1H), 4.10-4.01 (m, 1H), 3.80 (s, 2H), 3.24-3.13 (m, 1H), 2.89-2.78 (m, 1H), 2.28-2.19 (m, 1H), 2.17-2.08 (m, 1H), 2.04-1.92 (m, 1H), 1.79-1.68 (m, 1H); MS (ES+): m/z 539.3 and 541.3 (M + 1). |
| 16.6 | 1-(4-(4-(6-amino-5-(5-(3-chlorophenyl)oxazol-2-yl)pyridin-3-yl)-1H-pyrazol-1-yl)piperidin-1-yl)-2,2-dimethylpropan-1-one | pivaloyl chloride and 3-(5-(3-chlorophenyl)oxazol-2-yl)-5-(1-(piperidin-4-yl)-1H-pyrazol-4-yl)pyridin-2-amine; 10% | $^1$H NMR (400 MHz, CDCl$_3$): δ 8.32 (d, J = 2.4 Hz, 1H), 8.22 (d, J = 2.4 Hz, 1H), 7.79 (s, 1H), 7.74-7.72 (m, 1H), 7.69 (s, 1H), 7.64-7.60 (m, 1H), 7.50 (s, 1H), 7.44-7.40 (m, 1H), 7.37-7.33 (m, 1H), 6.67 (br s, 2H), 4.65-4.55 (m, 2H), 4.48-4.35 (m, 1H), 3.08-2.95 (m, 2H), 2.30-2.23 (m, 2H), 2.10-1.97 (m, 2H), 1.33 (s, 9H); MS (ES+): m/z 505.5 and 507.5 (M + 1). |
| 16.7 | (4-(4-(6-amino-5-(5-(3-chlorophenyl)oxazol-2-yl)pyridin-3-yl)-1H-pyrazol-1-yl)piperidin-1-yl)(4-fluorophenyl)methanone | 4-fluorobenzoyl chloride and 3-(5-(3-chlorophenyl)oxazol-2-yl)-5-(1-(piperidin-4-yl)-1H-pyrazol-4-yl)pyridin-2-amine; 12% | $^1$H NMR (400 MHz, CDCl$_3$): δ 8.32 (d, J = 2.4 Hz, 1H), 8.22 (d, J = 2.4 Hz, 1H), 7.80 (s, 1H), 7.74-7.72 (m, 1H), 7.70 (s, 1H), 7.64-7.60 (m, 1H), 7.51-7.46 (m, 3H), 7.44-7.39 (m, 1H), 7.37-7.33 (m, 1H), 7.16-7.09 (m, 2H), 6.70 (br s, 2H), 4.48-4.35 (m, 1H), 4.51-4.42 (m, 1H), 3.22-3.04 (m, 2H), 2.34-2.20 (m, 2H), 2.19-2.05 (m, 2H); MS (ES+): m/z 543.3 and 545.3 (M + 1). |

Example 17

Synthesis of 3-(5-(3-chlorophenyl)oxazol-2-yl)-5-(1-(1-methylpiperidin-4-yl)-1H-pyrazol-4-yl)pyridin-2-amine

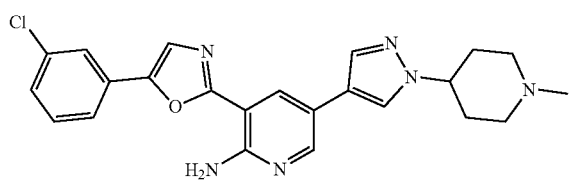 [SMILES: CN1CCC(n2cc(-c3cnc(N)c(-c4ncc(-c5cccc(Cl)c5)o4)c3)cn2)CC1]

To a solution of 3-(5-(3-chlorophenyl)oxazol-2-yl)-5-(1-(piperidin-4-yl)-1H-pyrazol-4-yl)pyridin-2-amine (50 mg, 0.12 mmol) in 4 mL of dichloromethane and methanol (1:1) at 0° C. was added formaldehyde (10 μL, 0.14 mmol), followed by the addition of sodium cyanoborohydride (9 mg, 0.14 mmol). The resulting mixture was warmed up to ambient temperature and stirred for another hour. The solvent was removed in vacuo and the residue was purified by column chromatography eluted with 1:10:89 ammonium hydroxide:methanol:dichloromethane to afford the title compound as a yellow solid in 83% yield (43.2 mg). $^1$H NMR (400 MHz, CDCl$_3$): δ8.32 (d, J=2.4 Hz, 1H), 8.21 (d, J=2.4 Hz, 1H), 7.78 (s, 1H), 7.73-7.68 (m, 2H), 7.63-7.58 (m, 1H), 7.49 (s, 1H), 7.43-7.38 (m, 1H), 7.38-7.32 (m, 1H), 6.67 (br s, 2H), 4.26-4.16 (m, 1H), 3.09-3.00 (m, 2H), 2.38 (s, 3H), 2.30-2.10 (m, 6H); MS (ES+): m/z 435.3 and 437.3 (M+1).

The table below shows additional examples of compounds of Formula (IA4) that were prepared according to the above process.

| Ex. No. | Chemical Name | Starting Material and Yield | Characterization Data |
|---|---|---|---|
| 17.1 | 3-(5-(4-Chlorophenyl)-oxazol-2-yl)-5-(1-(1-methylpiperidin-4-yl)-1H-pyrazol-4-yl)pyridin-2-amine | 3-(5-(4-chlorophenyl)oxazol-2-yl)-5-(1-(piperidin-4-yl)-1H-pyrazol-4-yl)pyridin-2-amine and formaldehyde; 75% | $^1$H NMR (400 MHz, CDCl$_3$ δ 8.32 (d, J = 2.4 Hz, 1H), 8.22 (d, J = 2.4 Hz, 1H), 7.77 (s, 1H), 7.70-7.66 (m, 3H), 7.48-7.44 (m, 3H), 6.63 (br s, 2H), 4.24-4.15 (m, 1H), 3.06-2.99 (m, 2H), 2.36 (s, 3H), 2.26-2.09 (m, 6H); (ES+): m/z 435.4 and 437.4 (M + 1). |
| 17.2 | 5-(1-(1-ethylpiperidin-4-yl)-1H-pyrazol-4-yl)-3-(5-phenyloxazol-2-yl)pyridin-2-amine | 3-(5-phenyloxazol-2-yl)-5-(1-(piperidin-4-yl)-1H-pyrazol-4-yl)pyridin-2-amine and acetaldehyde; 13% | $^1$H NMR (400 MHz, CDCl$_3$) δ 8.32 (d, J = 2.4 Hz, 1H), 8.23 (d, J = 2.4 Hz, 1H), 7.78-7.73 (m, 3H), 7.70 (s, 1H), 7.51-7.45 (m, 3H), 7.41-7.35 (m, 1H), 6.66 (br s, 2H), 4.27-4.18 (m, 1H), 3.17-3.10 (m, 2H), 2.50 (q, J = 7.2 Hz, 2H), 2.30-2.23 (m, 2H), 2.18-2.08 (m, 4H), 1.15 (t, J = 7.2 Hz, 3H); MS (ES+): m/z 415.4 (M + 1). |
| 17.3 | 5-(1-(1-dodecylpiperidin-4-yl)-1H-pyrazol-4-yl)-3-(5-phenyloxazol-2-yl)pyridin-2-amine | 3-(5-phenyloxazol-2-yl)-5-(1-(piperidin-4-yl)-1H-pyrazol-4-yl)pyridin-2-amine and dodecyl aldehyde; 23% | $^1$H NMR (400 MHz, CDCl$_3$) δ 8.31 (d, J = 2.4 Hz, 1H), 8.23 (d, J = 2.4 Hz, 1H), 7.77-7.72 (m, 3H), 7.69 (s, 1H), 7.51-7.45 (m, 3H), 7.40-7.35 (m, 1H), 6.65 (br s, 2H), 4.25-4.15 (m, 1H), 3.13-3.06 (m, 2H), 2.43-2.35 (m, 2H), 2.25-2.18 (m, 2H), 2.16-2.06 (m, 4H), 1.57-1.47 (m, 2H), 1.35-1.24 (m, 18H), 0.89 (t, J = 6.8 Hz, 3H); MS (ES+): m/z 555.5 (M + 1). |
| 17.4 | 5-(1-(1-methylpiperidin-4-yl)-1H-pyrazol-4-yl)-3-(5-phenylisoxazol-3-yl)pyridin-2-amine | 3-(5-phenylisoxazol-3-yl)-5-(1-(piperidin-4-yl)-1H-pyrazol-4-yl)pyridin-2-amine and formaldehyde; 61% | $^1$H NMR (400 MHz, CDCl$_3$): δ 8.30 (d, J = 2.4 Hz, 1H), 7.88-7.83 (m, 3H), 7.74 (s, 1H), 7.66 (s, 1H), 7.54-7.44 (m, 3H), 6.94 (s, 1H), 6.32-6.22 (br s, 2H), 4.23-4.13 (m, 1H), 3.07-2.98 (m, 2H), 2.37 (s, 3H), 2.28-2.06 (m, 6H); MS (ES+): m/z 401.4 (M + 1). |
| 17.5 | 5-(1-(1-methylpiperidin-4-yl)-1H-pyrazol-4-yl)-3-(5-phenylfuran-2-yl)pyridin-2-amine | 3-(5-phenylfuran-2-yl)-5-(1-(piperidin-4-yl)-1H-pyrazol-4-yl)pyridin-2-amine and formaldehyde; 30% | $^1$H NMR (400 MHz, CDCl$_3$): δ 8.21 (d, J = 2.0 Hz, 1H), 7.86 (d, J = 2.0 Hz, 1H), 7.76-7.70 (m, 3H), 7.66 (s, 1H), 7.46-7.41 (m, 2H), 7.33-7.29 (m, 1H), 6.81 (d, J = 3.6 Hz, 1H), 6.77 (d, J = 3.6 Hz, 1H), 5.20 (s, 2H), 4.25-4.16 (m, 1H), 3.10-3.00 (m, 2H), 2.25 (s, 3H), 2.32-2.10 (m, 6H); MS (ES+): m/z 400.4 (M + 1). |

BIOLOGICAL EXAMPLES

Example 18

Kinase Enzymatic Activity Assays

Preparation of Active Recombinant Kinase Proteins:

Recombinant human Tyro3 (455-end, the gene accession number NM_006293), human Axl (473-end, the gene accession number NM_021913) and human Mer (578-872, the gene accession number NM_006343) were independently expressed by baculovirus in Sf9 insect cells using an N-terminal GST tag. The recombinant proteins were stored at −70° C. in a medium containing 50 mM Tris-HCl, pH 7.5, 150 mM NaCl, 10 mM glutathione, 0.1 mM EDTA, 0.25 mM DTT, 0.1 mM PMSF and 25% glycerol. The recombinant proteins were aliquoted into smaller quantities after centrifugation to avoid repeated handling and multiple freeze/thaw cycles for the most favorable performance.

Preparation of Assay Reagents:

Kinase Assay Buffer: This buffer solution consisted of the following components: 25 mM MOPS, pH 7.2, 12.5 mM β-glycerol-phosphate, 25 mM MgCl$_2$, 5 mM EGTA, 2 mM EDTA and DTT 0.25 mM which was added prior to use.

Kinase Dilution Buffer: Kinase Assay Buffer was diluted at a 1:4 ratio (5× dilution) with distilled water.

[$^{33}$P]-ATP assay cocktail: In a designated radioactive working area, a 250 μM [$^{33}$P]-ATP assay cocktail was prepared by the addition of the following components: 150 μL of 10 mM ATP stock solution, 100 μL [$^{33}$P]-ATP (1 mci/100 μL), 5.75 mL of kinase assay buffer. This solution was stored in 1 mL aliquots at −20° C.

ATP stock solution (10 mM): The ATP stock solution was prepared by dissolving 55 mg of ATP in 10 mL of kinase assay buffer. It was stored in 200 μL aliquots at −20° C.

Active Kinase Stock Solution: The active recombinant kinase protein (0.1 μg/μL) was diluted with Kinase Dilution Buffer and the activity was assayed using a serial dilution method. The specific activity is expressed in nmoL/min/mg.

Substrates: poly(4:1 glu:tyr) is the substrate used for each kinase Tyro3, Axl and Mer: The peptide substrate was dissolved in water to give the final concentration of 1 mg/mL.

Test compound solution: Test compound was dissolved in DMSO to obtain a 10 mM solution. The assay solution was prepared by adding 5 μL of this solution to 955 μL of 10% DMSO/water to obtain the final concentration of 50 μM.

Assay Procedure:

The enzymatic activity of all three kinases was determined as follows. Using a 96-well plate, the wells were divided into three categories: Blank wells, Background wells and Test wells. In Test wells, 5 μL of the test compound solution and 5 μL of the substrate solution were added. In Control wells, 5 μL of 10% DMSO/water and 5 μL of the substrate solution were added. In Blank wells, 10 μL of 10% DMSO/water was added. To each well was added 10

μL of Active Kinase Stock Solution to make up the volume in each well to 20 μL. All test samples, controls and blanks were run in duplicate. The reaction was initiated by the addition of 5 μL of [$^{33}$P]-ATP assay cocktail, bringing the final volume up to 25 μL in every well. The mixture was incubated at room temperature for 30 minutes. The reaction was terminated by transferring 10 μL of the reaction mixture into a Millipore MultiScreen filter plate (cat. number MSPHN6B50). The filter plate was washed in a 1% phosphoric acid solution with constant gentle shaking for 15 minutes and this step was repeated once. After the plate was dried in air, scintillation fluid was added to each well and the radioactivity in each well in CPM was counted by a Microbeta TriLux. The corrected CPM in each test well was determined by subtracting the average value of Blank well values. Percentage of inhibition of the kinase enzymatic activity by the test compound was determined using the following formula:

$$\% \text{ Inhibition} = \left(1 - \frac{\text{Average of corrected } CPM \text{ in Test wells}}{\text{Average of corrected } CPM \text{ in Control wells}}\right) \times 100$$

The IC$_{50}$ values were determined in a similar way following a serial dilution of the test compound. The percentage of inhibition at each concentration was calculated following the above formula. The IC$_{50}$ was estimated from the curve of % Inhibition against Concentration in log unit using Prism 5, version 5.01.

The following table summarizes the inhibitory activity on Tyro3, Axl and Mer of the compounds of the disclosure. "+" represents the IC$_{50}$ is >10 μM; "++" represents the 1 μM<IC$_{50}$<10 μM; "+++" represents the 0.5 μM<IC$_{50}$<1 μM and "++++" represents the IC$_{50}$<0.5 μM.

| Chemical Name | IC$_{50}$ (nM) | | |
| --- | --- | --- | --- |
| | Tyro3 | Axl | Mer |
| tert-butyl 4-(4-(6-amino-5-(5-phenyl-1,3,4-oxadiazol-2-yl)pyridin-3-yl)-1H-pyrazol-1-yl)piperidine-1-carboxylate | ++ | ++ | ++ |
| tert-butyl 4-(4-(6-amino-5-(5-(4-(tert-butyl)phenyl)-1,3,4-oxadiazol-2-yl)pyridin-3-yl)-1H-pyrazol-1-yl)piperidine-1-carboxylate | ++ | +++ | ++++ |
| tert-butyl 4-(4-(6-amino-5-(5-(2,6-dichlorophenyl)-1,3,4-oxadiazol-2-yl)pyridin-3-yl)-1H-pyrazol-1-yl)piperidine-1-carboxylate | ++ | +++ | ND |
| tert-butyl 4-(4-(6-amino-5-(5-(4-fluorophenyl)-1,3,4-oxadiazol-2-yl)pyridin-3-yl)-1H-pyrazol-1-yl)piperidine-1-carboxylate | ++ | ++ | ++ |
| 3-(5-(2,6-dichlorophenyl)-1,3,4-oxadiazol-2-yl)-5-(1H-pyrazol-4-yl)pyridin-2-amine | ++++ | ++++ | ++++ |
| 3-(5-phenyl-1,3,4-oxadiazol-2-yl)-5-(1H-pyrazol-4-yl)pyridin-2-amine | ++++ | ++++ | +++ |
| 3-(5-(4-(tert-butyl)phenyl)-1,3,4-oxadiazol-2-yl)-5-(1H-pyrazol-4-yl)pyridin-2-amine | + | ++ | + |
| 3-(5-(2,5-difluorophenyl)-1,3,4-oxadiazol-2-yl)-5-(1H-pyrazol-4-yl)pyridin-2-amine | ++++ | ++++ | ++ |
| 3-(5-(4-fluorophenyl)-1,3,4-oxadiazol-2-yl)-5-(1H-pyrazol-4-yl)pyridin-2-amine | ++++ | ++++ | +++ |
| 5-(1-cyclohexyl-1H-pyrazol-4-yl)-3-(5-(2,6-dichlorophenyl)-1,3,4-oxadiazol-2-yl)pyridin-2-amine | + | + | + |
| 3-(3-phenyl-1,2,4-oxadiazol-5-yl)-5-(1-(tetrahydro-2H-pyran-4-yl)-1H-pyrazol-4-yl)pyridin-2-amine | + | + | + |
| tert-butyl 4-(4-(6-amino-5-(5-(pyridin-2-yl)-1,3,4-oxadiazol-2-yl)pyridin-3-yl)-1H-pyrazol-1-yl)piperidine-1-carboxylate | ++ | ++++ | ++ |
| tert-butyl 4-(4-(6-amino-5-(5-(pyridin-3-yl)-1,3,4-oxadiazol-2-yl)pyridin-3-yl)-1H-pyrazol-1-yl)piperidine-1-carboxylate | ++ | +++ | ++ |
| tert-butyl 4-(4-(6-amino-5-(5-(pyrazin-2-yl)-1,3,4-oxadiazol-2-yl)pyridin-3-yl)-1H-pyrazol-1-yl)piperidine-1-carboxylate | ++ | ++++ | ++ |
| tert-butyl 4-(4-(6-amino-5-(5-(cyclopropylmethyl)-1,3,4-oxadiazol-2-yl)pyridin-3-yl)-1H-pyrazol-1-yl)piperidine-1-carboxylate | ++ | ++++ | +++ |
| tert-butyl 4-(4-(6-amino-5-(5-benzyl-1,3,4-oxadiazol-2-yl)pyridin-3-yl)-1H-pyrazol-1-yl)piperidine-1-carboxylate | ++ | ++++ | ++ |
| tert-butyl 4-(4-(6-amino-5-(5-(thiazol-2-yl)-1,3,4-oxadiazol-2-yl)pyridin-3-yl)-1H-pyrazol-1-yl)piperidine-1-carboxylate | ++ | +++ | ++ |
| tert-butyl 4-(4-(6-amino-5-(5-(4-(trifluoromethyl)-thiazol-2-yl)-1,3,4-oxadiazol-2-yl)pyridin-3-yl)-1H-pyrazol-1-yl)piperidine-1-carboxylate | ++ | ++++ | + |
| 3-(5-phenyl-1,2,4-oxadiazol-3-yl)-5-(1H-pyrazol-4-yl)pyridin-2-amine | ++++ | ++++ | ++ |
| 3-(3-phenyl-1,2,4-oxadiazol-5-yl)-5-(1H-pyrazol-4-yl)pyridin-2-amine | ++ | +++ | ++ |
| 5-(1-cyclohexyl-1H-pyrazol-4-yl)-3-(3-phenyl-1,2,4-oxadiazol-5-yl)pyridin-2-amine | ++ | ++ | + |
| 3-(5-(2,6-dichlorophenyl)-1,3,4-oxadiazol-2-yl)-5-(1-(tetrahydro-2H-pyran-4-yl)-1H-pyrazol-4-yl)pyridin-2-amine | ++++ | ++++ | ++++ |
| 3-(5-phenyl-1,3,4-oxadiazol-2-yl)-5-(1-(tetrahydro-2H-pyran-4-yl)-1H-pyrazol-4-yl)pyridin-2-amine | ++++ | ++++ | ++++ |
| 5-(1-cyclohexyl-1H-pyrazol-4-yl)-3-(5-phenyl-1,3,4-oxadiazol-2-yl)pyridin-2-amine | ++ | ++ | + |

|  | IC$_{50}$ (nM) | | |
|---|---|---|---|
| Chemical Name | Tyro3 | Axl | Mer |
| 3-(3-(2,6-dichlorophenyl)-1,2,4-oxadiazol-5-yl)-5-(1-(tetrahydro-2H-pyran-4-yl)-1H-pyrazol-4-yl)pyridin-2-amine | ++++ | ++ | ++ |
| 5-(1-cyclohexyl-1H-pyrazol-4-yl)-3-(3-(2,6-dichlorophenyl)-1,2,4-oxadiazol-5-yl)pyridin-2-amine | ++++ | ++ | ++ |
| 3-(5-(2,6-dichloro-3-fluorophenyl)-1,3,4-oxadiazol-2-yl)-5-(1-(piperidin-4-yl)-1H-pyrazol-4-yl)pyridin-2-amine | ++++ | ++++ | ++++ |
| 3-(5-phenyl-1,3,4-oxadiazol-2-yl)-5-(1-(piperidin-4-yl)-1H-pyrazol-4-yl)pyridin-2-amine | ++++ | ++++ | ++++ |
| 3-(5-(4-(tert-butyl)phenyl)-1,3,4-oxadiazol-2-yl)-5-(1-(piperidin-4-yl)-1H-pyrazol-4-yl)pyridin-2-amine | ++++ | ++++ | ++++ |
| 3-(5-(2,5-difluorophenyl)-1,3,4-oxadiazol-2-yl)-5-(1-(piperidin-4-yl)-1H-pyrazol-4-yl)pyridin-2-amine | ++++ | ++++ | ND |
| 3-(5-(2,6-dichlorophenyl)-1,3,4-oxadiazol-2-yl)-5-(1-(piperidin-4-yl)-1H-pyrazol-4-yl)pyridin-2-amine | ++++ | ++++ | ND |
| 3-(5-(4-fluorophenyl)-1,3,4-oxadiazol-2-yl)-5-(1-(piperidin-4-yl)-1H-pyrazol-4-yl)pyridin-2-amine | ++++ | ++++ | ++++ |
| 3-(3-phenyl-1,2,4-oxadiazol-5-yl)-5-(1-(piperidin-4-yl)-1H-pyrazol-4-yl)pyridin-2-amine | ++++ | ++++ | ++++ |
| 3-(5-(cyclopropylmethyl)-1,3,4-oxadiazol-2-yl)-5-(1-(piperidin-4-yl)-1H-pyrazol-4-yl)pyridin-2-amine | ++++ | ++++ | ++++ |
| 5-(1-(piperidin-4-yl)-1H-pyrazol-4-yl)-3-(5-(pyridin-2-yl)-1,3,4-oxadiazol-2-yl)pyridin-2-amine | ++++ | ++++ | ++++ |
| 5-(1-(piperidin-4-yl)-1H-pyrazol-4-yl)-3-(5-(pyridin-3-yl)-1,3,4-oxadiazol-2-yl)pyridin-2-amine | ++++ | ++++ | ++++ |
| 5-(1-(piperidin-4-yl)-1H-pyrazol-4-yl)-3-(5-(pyrazin-2-yl)-1,3,4-oxadiazol-2-yl)pyridin-2-amine | ++++ | ++++ | +++ |
| 3-(5-benzyl-1,3,4-oxadiazol-2-yl)-5-(1-(piperidin-4-yl)-1H-pyrazol-4-yl)pyridin-2-amine | ++++ | ++++ | ++++ |
| 5-(1-(piperidin-4-yl)-1H-pyrazol-4-yl)-3-(5-(thiazol-2-yl)-1,3,4-oxadiazol-2-yl)pyridin-2-amine | ++++ | ++++ | ++++ |
| 5-(1-(piperidin-4-yl)-1H-pyrazol-4-yl)-3-(5-(4-(trifluoromethyl)thiazol-2-yl)-1,3,4-oxadiazol-2-yl)pyridin-2-amine | ++++ | ++++ | ++++ |
| 3-(5-cyclohexyl-1,3,4-oxadiazol-2-yl)-5-(1-(piperidin-4-yl)-1H-pyrazol-4-yl)pyridin-2-amine | ++++ | ++++ | ++++ |
| 3-(3-(2,6-dichlorophenyl)-1,2,4-oxadiazol-5-yl)-5-(1-(piperidin-4-yl)-1H-pyrazol-4-yl)pyridin-2-amine | ++++ | ++++ | ++++ |
| 3-(5-(2,6-dichlorophenyl)-1,3,4-oxadiazol-2-yl)-5-(1-(piperidin-4-yl)-1H-pyrrol-3-yl)pyridin-2-amine | ++++ | ++++ | ++++ |
| 1-(4-(4-(6-amino-5-(5-(2,6-dichlorophenyl)-1,3,4-oxadiazol-2-yl)pyridin-3-yl)-1H-pyrazol-1-yl)piperidin-1-yl)ethanone | ++++ | ++++ | ++++ |
| 1-(4-(4-(6-amino-5-(3-phenyl-1,2,4-oxadiazol-5-yl)pyridin-3-yl)-1H-pyrazol-1-yl)piperidin-1-yl)ethanone | ++++ | ++++ | ++++ |
| 3-(5-(2,6-dichlorophenyl)-1,3,4-oxadiazol-2-yl)-5-(1-(1-methylpiperidin-4-yl)-1H-pyrazol-4-yl)pyridin-2-amine | ++++ | ++++ | ++++ |
| 5-(1-(1-methylpiperidin-4-yl)-1H-pyrazol-4-yl)-3-(5-phenyl-1,2,4-oxadiazol-3-yl)pyridin-2-amine | ++++ | ++++ | +++ |
| 5-(1-(1-methylpiperidin-4-yl)-1H-pyrazol-4-yl)-3-(3-phenyl-1,2,4-oxadiazol-5-yl)pyridin-2-amine | ++++ | ++++ | ++++ |
| 3-(3-(2,6-dichlorophenyl)-1,2,4-oxadiazol-5-yl)-5-(1-(1-methylpiperidin-4-yl)-1H-pyrazol-4-yl)pyridin-2-amine | ++++ | ++++ | ++++ |
| 5-(1-(1-ethylpiperidin-4-yl)-1H-pyrazol-4-yl)-3-(3-phenyl-1,2,4-oxadiazol-5-yl)pyridin-2-amine | ++++ | ++++ | ++++ |
| 3-(3-(2,6-dichlorophenyl)-1,2,4-oxadiazol-5-yl)-5-(1-(1-dodecylpiperidin-4-yl)-1H-pyrazol-4-yl)pyridin-2-amine | ++++ | ++ | ++++ |
| 3-(3-(2,6-dichlorophenyl)-1,2,4-oxadiazol-5-yl)-5-(1-(1-ethylpiperidin-4-yl)-1H-pyrazol-4-yl)pyridin-2-amine | ++++ | ++++ | ++++ |
| 3-(5-(2,6-dichlorophenyl)-1,3,4-oxadiazol-2-yl)-5-(1-(1-ethylpiperidin-4-yl)-1H-pyrazol-4-yl)pyridin-2-amine | ++++ | ++++ | ++++ |
| 3-(5-(2,6-dichlorophenyl)-1,3,4-oxadiazol-2-yl)-5-(1-(1-dodecylpiperidin-4-yl)-1H-pyrazol-4-yl)pyridin-2-amine | +++ | ++ | ++ |
| 1-(4-(4-(6-amino-5-(5-(2,6-dichlorophenyl)-1,3,4-oxadiazol-2-yl)pyridin-3-yl)-1H-pyrazol-1-yl)piperidin-1-yl)-4-methylpentan-1-one | +++ | ++++ | ++++ |
| (4-(4-(6-amino-5-(3-phenyl-1,2,4-oxadiazol-5-yl)pyridin-3-yl)-1H-pyrazol-1-yl)piperidin-1-yl)(cyclopropyl)methanone | ++ | ++ | ++ |
| (4-(4-(6-amino-5-(5-(2,6-dichlorophenyl)-1,3,4-oxadiazol-2-yl)pyridin-3-yl)-1H-pyrazol-1-yl)piperidin-1-yl)(cyclopropyl)methanone | ++++ | ++++ | ++ |
| (4-(4-(6-amino-5-(5-(2,6-dichlorophenyl)-1,3,4-oxadiazol-2-yl)pyridin-3-yl)-1H-pyrazol-1-yl)piperidin-1-yl)(phenyl)methanone | ++++ | ++++ | ++++ |
| 5-(1-cyclohexyl-1H-pyrazol-4-yl)-3-(5-phenyl-1,2,4-oxadiazol-3-yl)pyridin-2-amine | + | + | + |

| Chemical Name | IC$_{50}$ (nM) | | |
|---|---|---|---|
| | Tyro3 | Axl | Mer |
| 3-(5-(2,5-dichlorophenyl)-1,2,4-oxadiazol-3-yl)-5-(1-(piperidin-4-yl)-1H-pyrazol-4-yl)pyridin-2-amine | ++++ | ++++ | +++ |
| 3-(5-phenyl-1,2,4-oxadiazol-3-yl)-5-(1-(tetrahydro-2H-pyran-4-yl)-1H-pyrazol-4-yl)pyridin-2-amine | +++ | ++++ | ++ |
| 3-(5-phenyl-1,2,4-oxadiazol-3-yl)-5-(1-(piperidin-4-yl)-1H-pyrazol-4-yl)pyridin-2-amine | ++++ | ++++ | ++++ |
| 1-(4-(4-(6-amino-5-(5-(2,6-dichlorophenyl)-1,3,4-oxadiazol-2-yl)pyridin-3-yl)-1H-pyrazol-1-yl)piperidin-1-yl)-2-phenylethanone | ++ | ++ | ++ |
| (4-(4-(6-amino-5-(3-phenyl-1,2,4-oxadiazol-5-yl)pyridin-3-yl)-1H-pyrazol-1-yl)piperidin-1-yl)(phenyl)methanone | ++ | ++ | ++ |
| 1-(4-(4-(6-amino-5-(3-phenyl-1,2,4-oxadiazol-5-yl)pyridin-3-yl)-1H-pyrazol-1-yl)piperidin-1-yl)-2-phenylethanone | ++ | +++ | ++ |
| 3-(5-phenyloxazol-2-yl)-5-(1-(tetrahydro-2H-pyran-4-yl)-1H-pyrazol-4-yl)pyridin-2-amine | ++++ | ++++ | + |
| tert-butyl 4-(4-(6-amino-5-(5-phenyloxazol-2-yl)pyridin-3-yl)-1H-pyrazol-1-yl)piperidine-1-carboxylate | +++ | ++++ | ++ |
| 3-(5-(4-chlorophenyl)oxazol-2-yl)-5-(1-(tetrahydro-2H-pyran-4-yl)-1H-pyrazol-4-yl)pyridin-2-amine | + | + | + |
| tert-butyl 4-(4-(6-amino-5-(5-(4-chlorophenyl)oxazol-2-yl)pyridin-3-yl)-1H-pyrazol-1-yl)piperidine-1-carboxylate | ++ | +++ | ++ |
| 3-(5-(3-chlorophenyl)oxazol-2-yl)-5-(1-cyclohexyl-1H-pyrazol-4-yl)pyridin-2-amine | ++ | ++ | ++ |
| 3-(5-(4-chlorophenyl)oxazol-2-yl)-5-(1-cyclohexyl-1H-pyrazol-4-yl)pyridin-2-amine | + | + | + |
| 5-(1-cyclohexyl-1H-pyrazol-4-yl)-3-(5-phenyloxazol-2-yl)pyridin-2-amine | ++ | ++ | + |
| 5-(1-cyclohexyl-1H-pyrazol-4-yl)-3-(5-phenylisoxazol-3-yl)pyridin-2-amine | ++ | ++ | ++ |
| 3-(5-phenylisoxazol-3-yl)-5-(1-(tetrahydro-2H-pyran-4-yl)-1H-pyrazol-4-yl)pyridin-2-amine | ++++ | ++++ | ++ |
| 5-(1-cyclohexyl-1H-pyrazol-4-yl)-3-(5-phenylfuran-2-yl)pyridin-2-amine | ++ | ++ | ++ |
| 3-(5-phenylfuran-2-yl)-5-(1-(tetrahydro-2H-pyran-4-yl)-1H-pyrazol-4-yl)pyridin-2-amine | ++ | ++ | ++ |
| 3-(5-phenyloxazol-2-yl)-5-(1-(piperidin-4-yl)-1H-pyrazol-4-yl)pyridin-2-amine | ++++ | ++++ | ++++ |
| 3-(5-(4-chlorophenyl)oxazol-2-yl)-5-(1-(piperidin-4-yl)-1H-pyrazol-4-yl)pyridin-2-amine | ++++ | ++++ | ++++ |
| 3-(5-(3-chlorophenyl)oxazol-2-yl)-5-(1-(piperidin-4-yl)-1H-pyrazol-4-yl)pyridin-2-amine | ++++ | ++++ | ++++ |
| 3-(5-phenylisoxazol-3-yl)-5-(1-(piperidin-4-yl)-1H-pyrazol-4-yl)pyridin-2-amine | ++++ | ++++ | ++++ |
| 3-(5-phenylfuran-2-yl)-5-(1-(piperidin-4-yl)-1H-pyrazol-4-yl)pyridin-2-amine | ++++ | ++++ | +++ |
| 5-(1-(piperidin-4-yl)-1H-pyrazol-4-yl)-3-(5-(pyridin-3-yl)oxazol-2-yl)pyridin-2-amine | ++++ | ++++ | ++++ |
| 1-(4-(4-(6-amino-5-(5-(4-chlorophenyl)oxazol-2-yl)pyridin-3-yl)-1H-pyrazol-1-yl)piperidin-1-yl)ethanone | + | + | + |
| 1-(4-(4-(6-amino-5-(5-(3-chlorophenyl)oxazol-2-yl)pyridin-3-yl)-1H-pyrazol-1-yl)piperidin-1-yl)ethanone | ++++ | ++++ | ++++ |
| (4-(4-(6-amino-5-(5-(4-chlorophenyl)oxazol-2-yl)pyridin-3-yl)-1H-pyrazol-1-yl)piperidin-1-yl)(cyclopropyl)methanone | ++++ | ++++ | + |
| (4-(4-(6-amino-5-(5-(3-chlorophenyl)oxazol-2-yl)pyridin-3-yl)-1H-pyrazol-1-yl)piperidin-1-yl)(cyclopropyl)methanone | +++ | ++++ | ++ |
| (4-(4-(6-amino-5-(5-(3-chlorophenyl)oxazol-2-yl)pyridin-3-yl)-1H-pyrazol-1-yl)piperidin-1-yl)(phenyl)methanone | ++++ | ++++ | ++ |
| 1-(4-(4-(6-amino-5-(5-(3-chlorophenyl)oxazol-2-yl)pyridin-3-yl)-1H-pyrazol-1-yl)piperidin-1-yl)-2-phenylethanone | ++++ | ++++ | ++ |
| (4-(4-(6-amino-5-(5-(4-chlorophenyl)oxazol-2-yl)pyridin-3-yl)-1H-pyrazol-1-yl)piperidin-1-yl)(phenyl)methanone | ++++ | ++++ | ++ |
| 1-(4-(4-(6-amino-5-(5-(4-chlorophenyl)oxazol-2-yl)pyridin-3-yl)-1H-pyrazol-1-yl)piperidin-1-yl)-2-phenylethanone | ++++ | ++++ | ++ |
| 1-(4-(4-(6-amino-5-(5-(3-chlorophenyl)oxazol-2-yl)pyridin-3-yl)-1H-pyrazol-1-yl)piperidin-1-yl)-2,2-dimethylpropan-1-one | ++++ | ++++ | ++ |
| (4-(4-(6-amino-5-(5-(3-chlorophenyl)oxazol-2-yl)pyridin-3-yl)-1H-pyrazol-1-yl)piperidin-1-yl)(4-fluorophenyl)methanone | ++++ | ++++ | ++ |
| 3-(5-(3-chlorophenyl)oxazol-2-yl)-5-(1-(1-methylpiperidin-4-yl)-1H-pyrazol-4-yl)pyridin-2-amine | ++++ | ++++ | ++++ |
| 3-(5-(4-chlorophenyl)oxazol-2-yl)-5-(1-(1-methylpiperidin-4-yl)-1H-pyrazol-4-yl)pyridin-2-amine | ++++ | ++++ | ++++ |
| 5-(1-(1-ethylpiperidin-4-yl)-1H-pyrazol-4-yl)-3-(5-phenyloxazol-2-yl)pyridin-2-amine | ++++ | ++++ | ++++ |

-continued

| Chemical Name | IC$_{50}$ (nM) | | |
|---|---|---|---|
| | Tyro3 | Axl | Mer |
| 5-(1-(1-dodecylpiperidin-4-yl)-1H-pyrazol-4-yl)-3-(5-phenyloxazol-2-yl)pyridin-2-amine | ++++ | ++++ | +++ |
| 5-(1-(1-methylpiperidin-4-yl)-1H-pyrazol-4-yl)-3-(5-phenylisoxazol-3-yl)pyridin-2-amine | ++++ | ++++ | ++++ |
| 5-(1-(1-methylpiperidin-4-yl)-1H-pyrazol-4-yl)-3-(5-phenylfuran-2-yl)pyridin-2-amine | ++++ | ++++ | ++ |

Example 19

Cell Viability Assay

Cell lines and reagents: A549 cells were cultured in Dulbecco's Modified Eagle Medium (DMEM, HyClone) containing 10% fetal bovine serum (FBS, Life technologies) and maintained in a humidified incubator at 37° C. with 5% $CO_2$.

Cell viability assay protocol: $5 \times 10^3$ A549 cells in 180 μL of DMEM containing 0.5% FBS were seeded in 96-well flat bottom plates (Costar) and incubated in a humidified incubator at 37° C. with 5% $CO_2$ for 24 hours. The test compound (20 μL) in different concentrations after a serial dilution was added to the wells to a final volume of 200 μL per well. The wells with zero compound concentration were used as the Control wells and the Test wells contained different concentrations of the test compound. To the Blank wells were added medium only. After 48 hours incubation, 40 μL of MTS (Promega) was added to each well and the plates were incubated for 10 minutes to 1 hour at 37° C. The cell viability was estimated by measurement of optical density at 490 nm using a microplate spectrophotometer (Molecular Devices).

Example 20

Thymidine Incorporation Assay $1 \times 10^4$ A549 cells in 180 μL of DMEM containing 0.5% FBS were seeded in a 96-well white Isoplate (PerkinElmer) and incubated in a humidified incubator at 37° C. with 5% $CO_2$ for 24 hours. The test compound in different concentrations after a serial dilution was added to the wells to a final volume of 200 μL per well. The wells with zero compound concentration were used as the Control wells and the wells containing different concentrations of the test compound were used as the Test wells. To the Blank wells were added water only. After 24-hour incubation, each well was labeled with 1 μCi of [$^3$H]thymidine (specific activity, 26.8 Ci/mmol, PerkinElmer), and plates were again incubated at 37° C. overnight. After incubation, 50 μL of cold trichloroacetic acid was added into each well and the plates were incubated at 4° C. for 1-2 hours. Plates were subsequently washed with distilled water 5 times and air-dried at room temperature. Scintillation liquid was added to each well and radioactivity in CPM was counted using a MicroBeta TriLux (PerkinElmer) counter. The corrected CPM in each well was determined by subtracting the average value of the Blank well values. Percentage of inhibition of the thymidine incorporation at tested concentrations by the test compound was determined using the following formula:

$$\% \text{ Inhibition} = \left(1 - \frac{\text{Average of corrected } CPM \text{ in Test wells}}{\text{Average of corrected } CPM \text{ in Control wells}}\right) \times 100$$

The IC$_{50}$ was then estimated from the curve of % Inhibition against concentration in log unit using Prism 5, version 5.01.

Example 21

Colony Formation Assay (Method #1)

A549 cells were treated with the test compound at different concentrations (5, 1 and 0.2 μM) in DMEM containing 0.5% FBS at 37° C. for 1 hour. After treatment, cells were seeded in the agar containing the test compound at different concentrations as outlined above in 6-well plates and the plates were incubated at 37° C. for 2 weeks. DMEM containing the various concentrations of the test compound was added on the top of agar and changed every 2-3 days. The viable colonies were stained with crystal violet and counted. This example is to demonstrate the capability of test compounds to prevent the formation of colonies.

Example 22

Colony Formation Assay (Method #2)

17,500 A549 cells were seeded in agar in each well of 6-well plates and cultured in DMEM containing 10% FBS at 37° C. for six days and the colonies were formed. The test compound dissolved in DMEM with different concentrations was added to the test wells of the plates and DMEM with no test compound or with diluted DMSO was added to the control wells. The plates were incubated at 37° C. for 18-20 days during which period the DMEM containing 10% FBS and the various concentrations of test compounds was changed every 2 to 3 days. The viable colonies were stained with crystal violet and counted. This example is to demonstrate the capability of teat compounds to inhibit the colony growth after they are established and/or to eliminate the established colonies.

Example 23

Western Blot Assay $5 \times 10^5$ A549 cells were starved in DMEM contains no FBS in 6-well plate overnight, and treated with different concentrations of test compounds in serum-free medium for 30 minutes at 37° C. Cells were subsequently stimulated with or without Gas6 (400 ng/mL) for 30 min at 37° C. Total proteins were extracted from the test compound treated cells using ice-cold RIPA buffer (50 mM Tris-HCl, pH 7.5, 150 mM NaCl, 1 mM EDTA, 1% (v/v) Triton-X 100, 0.1 (w/v) SDS) supplemented with protease inhibitor cocktail and phosphatase inhibitors. Protein concentrations were determined using Bradford assay. Twenty micrograms of total proteins were fractionated on 10% SDS-PAGE gels and transferred onto nitrocellulose membrane (Bio-rad). Transfer efficiency and loading were confirmed by reversible staining of the membrane with Ponseau S solution (MP Biomedicals) following protein transfer. Membranes were blocked at ambient temperature with 5% non-fat dry milk in Tris-buffered saline (TBS) containing 0.1% Tween-20 (TBST) for 1 hour and incubated with primary antibodies against Axl, Tyro3, phospho-AKT (Ser$^{473}$), total AKT or β-actin at 4° C. After overnight incubation, membranes were washed with TBST and incubated with a secondary horseradish peroxidase (HRP)-labeled antibody (Jackson ImmunoResearch Laboratories, Inc.) for 1 hour at ambient temperature. Membranes were washed in TBST following incubation with secondary antibodies. Bound antibody complexes were detected and visualized using Luminata Classico Western HRP Substrate (Millipore).

All of the U.S. patents, U.S. patent application publications, U.S. patent applications, foreign patents, foreign patent applications and non-patent publications referred to in this specification and/or listed in the Application Data Sheet are incorporated herein by reference, in their entirety.

From the foregoing it will be appreciated that, although specific embodiments of the disclosure have been described herein for purposes of illustration, various modifications may be made without deviating from the spirit and scope of the disclosure. Accordingly, the disclosure is not limited except as by the appended claims.

What is claimed is:

1. A compound represented by Formula (IA6):

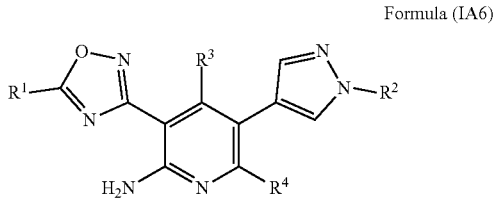

Formula (IA6)

wherein,
R$^1$ is phenyl or phenyl substituted by one or more halo;
R$^2$ is hydrogen, piperidinyl, or piperidinyl substituted by one or more alkyl; and
each of R$^3$ and R$^4$ is hydrogen.

2. A compound being:
5-(1-cyclohexyl-1H-pyrazol-4-yl)-3-(5-phenyl-1,2,4-oxadiazol-3-yl)pyridin-2-amine;
3-(5-phenyl-1,2,4-oxadiazol-3-yl)-5-(1-(tetrahydro-2H-pyran-4-yl)-1H-pyrazol-4-yl)pyridin-2-amine;
3-(5-phenyl-1,2,4-oxadiazol-3-yl)-5-(1-(piperidin-4-yl)-1H-pyrazol-4-yl)pyridin-2-amine;
5-(1-(1-methylpiperidin-4-yl)-1H-pyrazol-4-yl)-3-(5-phenyl-1,2,4-oxadiazol-3-yl)pyridin-2-amine;
3-(5-(2,5-dichlorophenyl)-1,2,4-oxadiazol-3-yl)-5-(1-(piperidin-4-yl)-1H-pyrazol-4-yl)pyridin-2-amine;
3-(5-phenyl-1,2,4-oxadiazol-3-yl)-5-(1H-pyrazol-4-yl) pyridin-2-amine.

3. A pharmaceutical composition comprising a compound of claim 1 and a pharmaceutically acceptable excipient.

4. A pharmaceutical composition comprising a compound of claim 2 and a pharmaceutically acceptable excipient.

* * * * *